US008012734B2

(12) United States Patent
Lavigne et al.

(10) Patent No.: US 8,012,734 B2
(45) Date of Patent: Sep. 6, 2011

(54) CELLULASE VARIANTS WITH REDUCED INHIBITION BY GLUCOSE

(75) Inventors: James A. Lavigne, Ontario (CA); Christopher M. D. Hill, Ontario (CA); Annie Tremblay, Ontario (CA); Patrick St-Pierre, Ontario (CA); John J. Tomashek, Ontario (CA)

(73) Assignee: Iogen Energy Corporation, Ontario (CA)

( * ) Notice: Subject to any disclaimer, the term of this patent is extended or adjusted under 35 U.S.C. 154(b) by 136 days.

(21) Appl. No.: 12/355,373

(22) Filed: Jan. 16, 2009

(65) Prior Publication Data

US 2009/0186381 A1 Jul. 23, 2009

Related U.S. Application Data

(60) Provisional application No. 61/022,101, filed on Jan. 18, 2008.

(51) Int. Cl.
*C12P 21/06* (2006.01)
*C12N 9/02* (2006.01)
*C12N 9/42* (2006.01)
*C12N 1/20* (2006.01)
*C07H 21/04* (2006.01)

(52) U.S. Cl. ..... 435/209; 435/69.1; 435/189; 435/252.3; 435/320.1; 536/23.2

(58) Field of Classification Search .................... None
See application file for complete search history.

(56) References Cited

U.S. PATENT DOCUMENTS

| | | | |
|---|---|---|---|
| 6,015,703 | A | 1/2000 | White et al. |
| 7,198,925 | B2 | 4/2007 | Foody |
| 2003/0054535 | A1 | 3/2003 | Himmel et al. |
| 2004/0152872 | A1 | 8/2004 | Wohlfahrt et al. |
| 2006/0205042 | A1 | 9/2006 | Aehle et al. |
| 2008/0076152 | A1 | 3/2008 | St-Pierre et al. |
| 2008/0289006 | A1 | 11/2008 | Hock et al. |

FOREIGN PATENT DOCUMENTS

WO 99/01544 A1 1/1999

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Igarashi, et al., "Cellobiose dehydrogenase enhances Phanerochaete chrysosporium cellobiohydrolase I activity by relieving product inhibition", Eur. J. Biochem., vol. 253 (1998) 101-6.
Tolan, Iogen's Process for Producing Ethanol from Cellulosic Biomass, Clean Techn. and Enviro. Policy, vol. 3 (2002) 339-45.
Barr et al., Identification of Two Functionally Different Classes of Exocellulases, Biochemistry, vol. 35 (1996) 586-92.
Bulter et al., Preparing Libraries in *Saccharomyces cerevisiae*, Methods of Molecular Biology (F.H. Arnold and G. Georgiou, eds.) Humana Press Inc., vol. 231 (2003) 17-22.

Zhang et al., Site-directed mutation of noncatalytic residues of Thermobifida fusca exocellulase Cel6B, Eur. J. Biochem., vol. 267 (2000) 3101-15.
Perlack, et al., Biomass as Feedstock for a Bioenergy and Bioproducts Industry: The Technical Feasibility of a Billion-Ton Annual Supply, USDA/USDE (Apr. 2005) 1-78.
Vallejo, et al., In vitro synthesis of novel genes: mutagenesis and recombination by PCR, Genome Res., vol. 4 (1994) 123-30.
Teleman, et al., Progress-curve analysis shows that glucose Inhibits the cellotriose hydrolysis catalysed by cellobihydrolase II from *Trichoderma reesei*, Eur. J. Biochem., vol. 231 (1995) 250-58.
Eriksson, et al., A Model Explaining Declining Rate in Hydrolysis of Lignocellulose Substrates with Cellobiohydrolase I (Cel7A) and Endoglucanase I (Cel7B) of *Trichoderma reesei*, Applied Biochemistry and Biotechnology, vol. 101 (2002) 41-60.
Gruno, et al., Inhibition of the *Trichoderma reesei* Cellulases by Cellobiose is Strongly Dependent on the Nature of the Substrate, Biotechnology and Bioengineering, vol. 86, No. 5 (2004) 503-11.
Caminal et al., Kinetic Modeling of the Enzymatic Hydrolysis of Pretreated Cellulose, Biotechnology and Bioengineering, vol. 27 (1985) 1282-90.
Claeyssens et al., Specificity mapping of cellulolytic enzymes: Classification into families of structurally related proteins confirmed by biochemical analysis, Protein Science, vol. 1 (1992) 1293-97.
Converse et al., A Model of Enzyme Adsorption and Hydrolysis of Microcrystalline Cellulose with Slow Deactivation of the Absorbed Enzyme, Biotechnology and Bioengineering, vol. 32 (1988) 38-45.
Holtzapple et al., Inhibition of *Trichoderma reesei* Cellulase by Sugars and Solvents, Biotechnology and Bioengineering, vol. 36 (1990) 275-87. Lee et al., Kinetic Studies of Enzymatic Hydrolysis of Insoluble Cellulose: (II), Analysis of Extended Hydrolysis Times, Biotechnology and Bioengineering, vol. 25 (1983) 939-66.
Meinke et al., Enhancement of the Endo-Beta-1,4-glucanase Activity of an Exocellobiohydrolase by Deletion of a Surface Loop, Journal of Biological Chemistry, vol. 270, No. 9 (1995) 4383-86.
Nidetzky et al., A New Approach for Modeling Cellulase—Cellulose Adsorption and the Kinetics of the Enzymatic Hydrolysis of Microcrystalline Cellulose, Biotechnology and Bioengineering, vol. 42, No. 4 (1993) 469-79.
Farrell et al., Ethanol Can Contribute to Energy and Environmental Goals, Science, vol. 311 (2006) 506-08.

(Continued)

*Primary Examiner* — Christian Fronda
(74) *Attorney, Agent, or Firm* — Fitzpatrick, Cella, Harper & Scinto

(57) ABSTRACT

A Family 6 cellulase variant enzyme comprising one or more than one amino acid substitution selected from a basic, polar or non-polar amino acid at position 103, a valine or isoleucine at position 136, a tyrosine at position 186, a glutamic acid or glutamine at position 365 and a glutamine at position 410 is provided (said position determined form alignment of the parental Family 6 with SEQ ID NO: 1). Genetic constructs and genetically modified microbes comprising DNA sequences encoding the Family 6 cellulase variant are also provided. Family 6 cellulases of the invention display reduced inhibition by glucose relative to the parent Family 6 cellulases. Such cellulases find use in a variety of applications in industry, e.g., in the hydrolysis of pretreated lignocellulosic feedstock, that require cellulose activity in the presence glucose concentrations that would otherwise inhibit the activity of the parental enzyme.

19 Claims, 18 Drawing Sheets

OTHER PUBLICATIONS

Gusakov et al., A Theoretical Analysis of Cellulase Product Inhibition: Effect of Cellulase Binding Constant, Enzyme/Substrate Ratio, and Beta-Glucosidase Activity on the Inhibition Pattern, Biotechnology and Bioengineering, vol. 40, No. 6 (1992) 663-72.

Zhang et al., Substrate Heterogeneity Causes the Nonlinear Kinetics of Insoluble Cellulose Hydrolysis, Biotechnology and Bioengineering, vol. 66, No. 1 (1999) 35-41.

Steipe, Consensus-Based Engineering of Protein Stability: From Intrabodies to Thermostable Enzymes, Methods in Enzymology, vol. 388 (2004) 176-86.

Gietz et al., Transformation of Yeast by Lithium Acetate/Single-Stranded Carrier DNA/Polyethylene Glycol Method, Methods in Enzymology, vol. 350, No. 3 (2002) 87-96.

Hoffman et al., A ten-minute DNA preparation from yeast efficiently releases autonomous plasmids for transformation of *Escherichia coli*, Gene, vol. 57 (1987) 267-72.

* cited by examiner

CELLULASE VARIANTS WITH REDUCED INHIBITION BY GLUCOSE

This application claims benefit of prior provisional application No. 61/022,101 filed Jan. 18, 2008.

TECHNICAL FIELD

The present invention relates to cellulase variants. More specifically, the invention relates to Family 6 cellulase variants with reduced inhibition by glucose. The present invention also relates to genetic constructs comprising nucleotide sequences encoding for Family 6 cellulase variants, methods for the production of Family 6 cellulase variants from host strains and the use of Family 6 cellulase variants in the hydrolysis of cellulose.

BACKGROUND OF THE INVENTION

Cellulose is an unbranched polymer of glucose linked by $\beta(1\rightarrow 4)$-glycosidic bonds. Cellulose chains can interact with each other via hydrogen bonding to form a crystalline solid of high mechanical strength and chemical stability. The cellulose chains must be depolymerized into glucose and short oligosaccharides before organisms, such as the fermenting microbes used in ethanol production, can use them as metabolic fuel. Cellulase enzymes catalyze the hydrolysis of the cellulose (hydrolysis of $\beta$-1,4-D-glucan linkages) in the feedstock into products such as glucose, cellobiose, and other cellooligosaccharides. Cellulase is a generic term denoting a multienzyme mixture comprising exo-acting cellobiohydrolases (CBHs), endoglucanases (EGs) and $\beta$-glucosidases ($\beta$G) that can be produced by a number of plants and microorganisms. Enzymes in the cellulase of *Trichoderma reesei* include CBH1 (more generally, Cel7A), CBH2 (Cel6A), EG1 (Cel7B), EG2 (Cel5), EG3 (Cel12), EG4 (Cel61A), EG5 (Cel45A), EG6 (Cel74A), Cip1, Cip2, $\beta$-glucosidases (including, e.g., Cel3A), acetyl xylan esterase, $\beta$-mannanase, and swollenin.

Cellulase enzymes work synergistically to hydrolyze cellulose to glucose. CBH1 and CBH2 act on opposing ends of cellulose chains (Barr et al., 1996), while the endoglucanases act at internal locations in the cellulose. The primary product of these enzymes is cellobiose, which is further hydrolyzed to glucose by one or more $\beta$-glucosidases.

The kinetics of the enzymatic hydrolysis of insoluble cellulosic substrates by cellulases do not follow simple Michaelis-Menten behaviour (Zhang et al., 1999). Specifically, increasing the dosage of cellulase in a hydrolysis reaction does not provide a linearly dependent increase in the amount of glucose produced in a given time. There is also a significant decrease in the rate of reaction as cellulose hydrolysis proceeds (Tolan, 2002). Several explanations have been proposed to explain the decline in the reaction rate; the major hypotheses include substrate heterogeneity (Nidetsky and Steiner, 1993; Zhang et al., 1999), enzyme inactivation (Caminal et al., 1985; Converse et al., 1988; Gusakov and Sinitsyn, 1992; Eriksson et al., 2002), and product inhibition (Lee and Fan, 1983; Caminal et al., 1985; Holtzapple et al., 1990; Gusakov and Sinitsyn, 1992; Eriksson et al., 2002; Gruno et al., 2004).

Inhibition of enzymes by the products of the reactions they catalyze has long been recognized; the phenomenon was known to Henri, Michaelis, and Menten, all pioneers in the field of enzymology (Frieden and Walter, 1963). The nature of product inhibition may be competitive, as product competes with substrate to form the same interactions with the enzyme, but other forms of inhibition are possible. Indeed, due to the insoluble nature of cellulose and the challenges it poses as a substrate in kinetic studies, there have been many conflicting reports as to the nature of inhibition in the cellulase system (Holtzapple et al., 1990, and references therein). The cellobiohydrolases are subject to inhibition by their direct product, cellobiose, and to a lesser degree by the glucose produced by the further hydrolysis of the cellobiose by $\beta$-glucosidase. One technique for reducing cellulase inhibition is to increase the amount of $\beta$-glucosidase in the system (U.S. Pat. No. 6,015,703), as cellobiose is more inhibitory to cellulases than glucose (Holtzapple et al., 1990; Teleman et al., 1995). Inhibition can be mitigated by altering the primary sequence of the protein using DNA mutagenesis guided by rational design or applied randomly. For example, rational design was used to target the Y245 residue in Cel5A, an endoglucanase, for mutagenesis, which resulted in an increase in its cellobiose inhibition constant (U.S. Publication No. 2003/0054535).

There are relatively few reports of engineering Cel6A (also known as cellobiohydrolase II or CBH2), a major cellobiohydrolase of the *T. reesei* (also known as *Hypocrea jecorina*) cellulase system, for desirable properties. St-Pierre et al. (U.S. Publication No. 2008/0076152) have shown that substitution of the naturally occurring amino acids at the equivalent of positions 231, 305, 410 and 413 in the *T. reesei* Cel6A sequence to serine or threonine (positions 231 and 305), glutamine or asparagines (position 410) or proline (position 413) increase thermostability, thermophilicity and/or alkalophilicity of a Family 6 cellulase. Wohlfahrt et al. have enhanced the stability of the protein by forming amide-carboxylate pairs through mutagenesis at residues E107, D170 and D366 (U.S. Publication No. 2004/0152872). Rational design was also applied to a related cellobiohydrolase, Cel6B from *Thermobifida fusca*, to relieve inhibition by cellobiose (Zhang et al., 2000). Mutations at Cel6B residues equivalent to W269, H266, and E399 in the Cel6A sequence were shown to reduce cellobiose inhibition, but at a significant cost to activity on crystalline cellulose. Another approach, based on the consensus sequence derived from an alignment of Cel6A sequences from several species (U.S. Publication No. 2006/0205042), identified 38 amino acids associated with improved thermostability (specifically: V94, P98, G118, M120, M134, T142, M145, T148, T154, L179, Q204, V206, I212, L215, G231, T232, V250, Q276, N285, S291, G308, T312, S316, V323, N325, I333, G334, S343, T349, G360, S380, A381, S390, F411, S413, A416, Q426 and A429). The authors speculate that these mutations may also affect product inhibition and/or enzyme processivity, but offer no data or specific hypotheses based on modeling to associate changes in these properties with the claimed residues. The consensus approach is designed to generate protein variants with improved thermodynamic stability (Steipe, 2004) and it does not provide predictive power for the improvement of any other biochemical property.

Although cellulase compositions have been described previously, there remains a need for new and improved compositions for use in the conversion of cellulose into fermentable sugars and for related fields of cellulosic material processing such as pulp and paper, textiles and animal feeds. Cellulases with improved performance decrease the cost of the processes and typically offer substantial environmental benefits when compared to the equivalent chemical and/or physical processes. For example, the production of fuel ethanol from cellulose delivers substantial environmental and economic benefits. When compared to gasoline, using ethanol as a fuel significantly reduces net carbon emissions by fixing the carbon dioxide released during combustion back into the biomass grown as feedstock for further ethanol production. Using agricultural biomass as feedstock can also stimulate rural economies and reduce dependence on foreign petroleum. Producing ethanol from cellulose rather than starch, as for corn ethanol, or sugar has the additional benefit of avoiding competition with the production of foodstuffs for humans and animals. The US Departments of Agriculture and Energy estimate that 30% of transportation fuel use in America, the largest petroleum market in the world, could be displaced by using cellulosic fuel without affecting food harvests (Perlack et al., 2005). Additionally, due to the low energy input required to generate cellulosic biomass, it has been estimated that the use of cellulose ethanol reduces net greenhouse gas production by 88% when compared to gasoline whereas using corn ethanol produces a decrease of only 18% (Farrell et al., 2006).

SUMMARY OF THE INVENTION

The present invention relates to Family 6 cellulase variants. More specifically, the invention relates to Family 6 cellulase variants that exhibit reduced inhibition by glucose. The present invention also relates to genetic constructs comprising nucleotide sequences encoding for Family 6 cellulase variants, methods for the production of Family 6 cellulase variants from host strains and the use of the Family 6 cellulase variants in the hydrolysis of cellulose.

It is an object of the invention to provide an improved cellulase with reduced inhibition by glucose.

This invention relates to a Family 6 cellulase variant comprising one or more of the amino acid substitutions selected from the group consisting of:

a basic, non-polar or proline residue at position 103 (X103H, K, R, A, V, L, P, M),
  a valine or isoleucine residue at position 136 (X136V, I),
  a tyrosine or lysine residues at position 186 (X186Y, K),
  an acidic, glutamine or serine residue at position 365 (X365D, E, Q, S), and
  an alanine, phenylalanine, leucine, glutamine or serine residue at position 410 (X410A, F, L, Q, S).

The positions of the amino acid substitution(s) are determined from sequence alignment of the Family 6 cellulase variant with a *Trichoderma reesei* Cel6A amino acid sequence as defined in SEQ ID NO: 1. The basic amino acid at position 103 may be a histidine, arginine or lysine or the non-polar amino acid at position 103 is an alanine, valine, methionine or leucine. The Family 6 cellulase variant of the present invention exhibits at least about 1.4-fold less inhibition by glucose than the parental Family 6 cellulase from which it is derived. For example, the Family 6 cellulase variant may exhibit from about 1.4-, 1.5-, 1.6-, 1.8-. 2.0-, 2.5-, 3.0-, 3.5, 4-, 5-, 6, 7-, 8-, 9-, 10-, 11-, 12-, 13-, 14-, 15-, 16-, 17-, 18-, 19- or 20-fold less inhibition by glucose than the parental Family 6 cellulase from which it is derived.

In one embodiment of the invention, the Family 6 cellulase variant of the present invention has an amino acid sequence that is at least about 45% to about 100% identical to the amino acids 83-447 of SEQ ID NO: 1. For example, the Family 6 cellulase variant may have an amino acid sequence that is at least about 55% to about 100% identical to the amino acids 83-447 of SEQ ID NO: 1, or at least about 63% to about 100% identical to the amino acids 83-447 of SEQ ID NO: 1

In still another embodiment, the Family 6 cellulase variant of the present invention has an amino acid sequence that is least about 95% identical to amino acids 83-447 of SEQ ID NO: 1

The Family 6 cellulase variant may be derived from a parental Family 6 cellulase that comprises one or more naturally-occurring amino acid(s) at the substituted positions corresponding to that of the Family 6 cellulase variant, but that is otherwise identical to the Family 6 cellulase variant, for example a native Family 6 cellulase from *Neocallimastix patriciarum, Orpinomyces*, or *Thermobifidia fusca*. The parental Family 6 cellulase may contain one or more amino acid substitutions at other positions, given that these substitutions are also present in the corresponding Family 6 cellulase variant.

This invention also includes a Family 6 cellulase variant as defined above and further comprising one or more of an isoleucine, valine, threonine, tyrosine or glutamine residue at position 134, an isoleucine residue at position 215 and a proline residue at position 413. The Family 6 cellulase variant comprising these mutations may be from a filamentous fungus, such as *Trichoderma reesei*.

The present invention also relates to Family 6 cellulase variants exhibiting at least 1.4-fold less inhibition by glucose than a parental Family 6 cellulase from which it is derived, said Family 6 cellulase variant being selected from the group consisting of:

TrCel6A-Y103A-S413P (SEQ ID NO: 37);
TrCel6A-Y103H-S413P (SEQ ID NO: 38);
TrCel6A-Y103K-S413P (SEQ ID NO: 39);
TrCel6A-Y103L-S413P (SEQ ID NO: 40);
TrCel6A-Y103M-S413P (SEQ ID NO: 41);
TrCel6A-Y103P-S413P (SEQ ID NO: 42);
TrCel6A-Y103R-S413P (SEQ ID NO: 43);
TrCel6A-Y103V-S413P (SEQ ID NO: 44);
TrCel6A-L136I-S413P (SEQ ID NO: 45);
TrCel6A-L136V-S413P (SEQ ID NO: 46);
TrCel6A-S186K-S413P (SEQ ID NO: 47);
TrCel6A-S186Y-S413P (SEQ ID NO: 48);
TrCel6A-G365D-S413P (SEQ ID NO: 49);
TrCel6A-G365E-S413P (SEQ ID NO: 50);
TrCel6A-G365Q-S413P (SEQ ID NO: 51);
TrCel6A-G365S-S413P (SEQ ID NO: 52);
TrCel6A-R410A-S413P (SEQ ID NO: 53);
TrCel6A-R410F-S413P (SEQ ID NO: 54);
TrCel6A-R410L-S413P (SEQ ID NO: 55);
TrCel6A-R410Q-S413P (SEQ ID NO: 56);
TrCel6A-R410S-S413P (SEQ ID NO: 57);
TrCel6A-M134V-L136I-S413P (SEQ ID NO: 62);
TrCel6A-L136I-L215I-S413P (SEQ ID NO: 63);
TrCel6A-M134V-L136I-L215I-S413P (SEQ ID NO: 71);
HiCel6A-Y107K (SEQ ID NO: 78);
HiCel6A-Y107L (SEQ ID NO: 79);
HiCel6A-Q139T (SEQ ID NO: 80);
HiCel6A-L141V (SEQ ID NO: 81);
HiCel6A-A194Y (SEQ ID NO: 82);
PcCel6A-Y98K (SEQ ID NO: 83);
PcCel6A-Y98L (SEQ ID NO: 84);
PcCel6A-L131I (SEQ ID NO: 85);
PcCel6A-L131V (SEQ ID NO: 86);
PcCel6A-S182K (SEQ ID NO: 87);
PcCel6A-S182Y (SEQ ID NO: 88);
PcCel6A-G359Q (SEQ ID NO: 89);
PcCel6A-R404Q (SEQ ID NO: 90);

Furthermore, the present invention also relates to genetic constructs for directing expression and secretion of the Family 6 cellulase variant from a host microbe including, but not limited to, strains of *Trichoderma reesei* or *Saccharomyces cerevisiae*.

The present invention relates to genetic construct comprising a DNA sequence encoding A Family 6 cellulase variant having one or more of a basic, non-polar or proline residue at position 103, a valine or isoleucine residue at position 136, a tyrosine or lysine residue at position 186, an acidic, glutamine or serine residue at position 365, or an alanine, phenylalanine, leucine, glutamine or serine residue at position 410, which DNA sequence is operably linked to DNA sequences regulating its expression and secretion from a host microbe. Preferably, the DNA sequences regulating the expression and secretion of the Family 6 cellulase variant are derived from the host microbe used for expression of the isolated cellulase. The host microbe may be a yeast, such as *Saccharomyces cerevisiae*, or a filamentous fungus, such as *Trichoderma reesei*.

The invention also relates to a genetic construct as defined above, wherein the Family 6 cellulase variant encoded by the genetic construct further comprises one or more of a valine or threonine residue at position 134, an isoleucine residue at position 215 and a proline residue at position 413. Preferably, the DNA sequences regulating the expression and secretion of the Family 6 cellulase variant are derived from a filamentous fungus, including, but not limited to, *Trichoderma reesei*.

The invention also relates to a genetically modified microbe comprising a genetic construct encoding the Family 6 cellulase variant and capable of expression and secretion of a Family 6 cellulase variant comprising one or more of a basic, non-polar or proline residue at position 103, a valine or isoleucine residue at position 136, a tyrosine or lysine residues at position 186, an acidic, glutamine or serine residue at position 365, or an alanine, phenyl alanine, leucine, glutamine or serine residue at position 410. In one embodiment, the Family 6 cellulase variant further comprises one or more of a valine or threonine residue at position 134, an isoleucine residue at position 215 and a proline residue at position 413. Preferably, the genetically modified microbe is a yeast or filamentous fungus. More preferably, the genetically modified microbe is a species of *Saccharomyces, Pichia, Hansenula, Hypocrea, Trichoderma, Aspergillus, Fusarium, Humicola* or *Neurospora*.

The present invention also relates to the use of a Family 6 cellulase variant comprising one or more of a basic, non-polar or proline residue at position 103, a valine or isoleucine residue at position 136, a tyrosine or lysine residues at position 186, an acidic, glutamine or serine residue at position 365, or an alanine, phenylalanine, leucine, glutamine or serine residue at position 410 for hydrolysis of a cellulosic substrate.

The invention also relates to a process of producing the Family 6 cellulase variant as defined above, including transformation of a yeast or fungal host with a genetic construct comprising a DNA sequence encoding the Family 6 cellulase variant, selection of recombinant yeast or fungal strains expressing the Family 6 cellulase variant, and culturing the selected recombinant strains in submerged liquid fermentations under conditions that induce the expression of the Family 6 cellulase variant.

Family 6 cellulase variants of the present invention comprising one or more of a basic, non-polar or proline residue at position 103, a valine or isoleucine residue at position 136, a tyrosine or lysine residues at position 186, an acidic, glutamine or serine residue at position 365, or an alanine, phenylalanine, leucine, glutamine or serine residue at position 410 display reduced glucose inhibition relative to the parental Family 6 cellulases from which they are derived. Family 6 cellulase variants, as described herein, cellulases find use in a variety of applications in industry that require high concentrations of cellulosic substrates and enzymes that can retain high activity in the presence of normally inhibitory concentrations of the glucose produced from such substrates. For example, Family 6 cellulase variants, as described herein, may be used for the purposes of saccharification of lignocellulosic feedstocks for the production of fermentable sugars, or improving the digestibility of feeds in ruminant and non-ruminant animals.

BRIEF DESCRIPTION OF THE DRAWINGS

FIG. 1 shows an amino acid sequence alignment of 35 fungal Family 6 cellulases to amino acids 83-447 of *Trichoderma reesei* Cel6A (TrCel6A; SEQ ID NO:1). The amino acid numbering for each cellulase is as indicated at the left and right of each sequence. The residues at positions 103, 134, 136, 186, 215, 365, 410, and 413 (relative to TrCel6A) are indicated with an arrow. For cellulases with a cellulose-binding domain, only the catalytic core sequences are presented. CfCel6B (SEQ ID NO:2); HiCel6A (SEQ ID NO:3); HiCel6B (SEQ ID NO:4); MtCel6A (SEQ ID NO:5); NpCel6A (SEQ ID NO:6); OpC2Cel6F (SEQ ID NO:7); PcCel6A (SEQ ID NO:8); PE2Cel6A (SEQ ID NO:9); TfCel6A (SEQ ID NO:10); TfCel6B (SEQ ID NO:11).

DETAILED DESCRIPTION OF THE INVENTION

Figure 2:
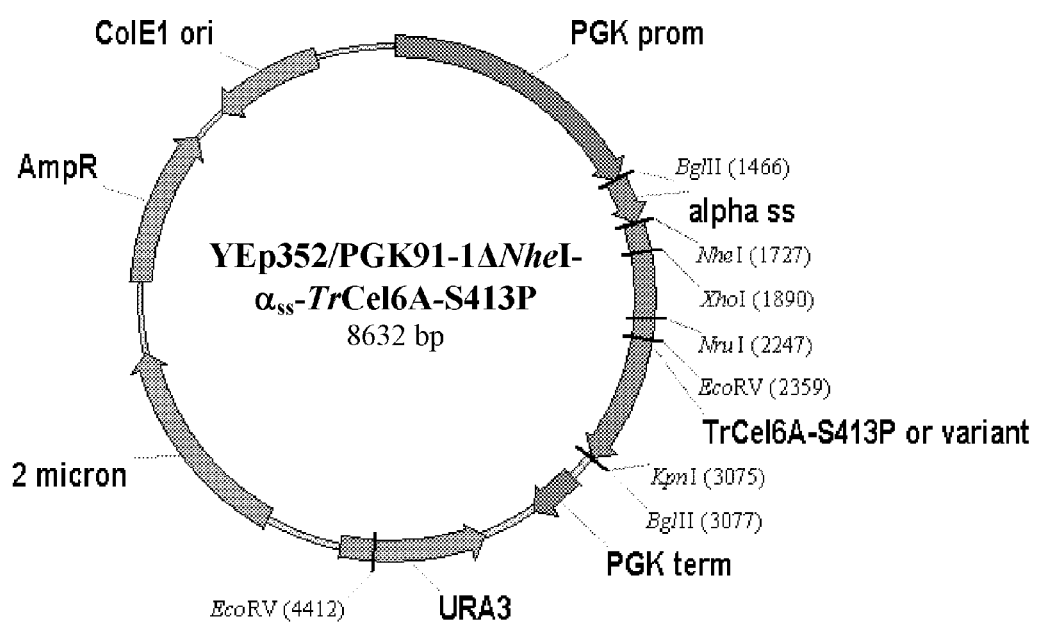
FIG. 2 depicts plasmid vector YEp352/PGK91-1ΔNhe I-a $_{ss}$-TrCel6A-S413P directing the expression and secretion of parental and variant TrCel6A cellulases from recombinant *Saccharomyces cerevisiae*.
Figure 3:
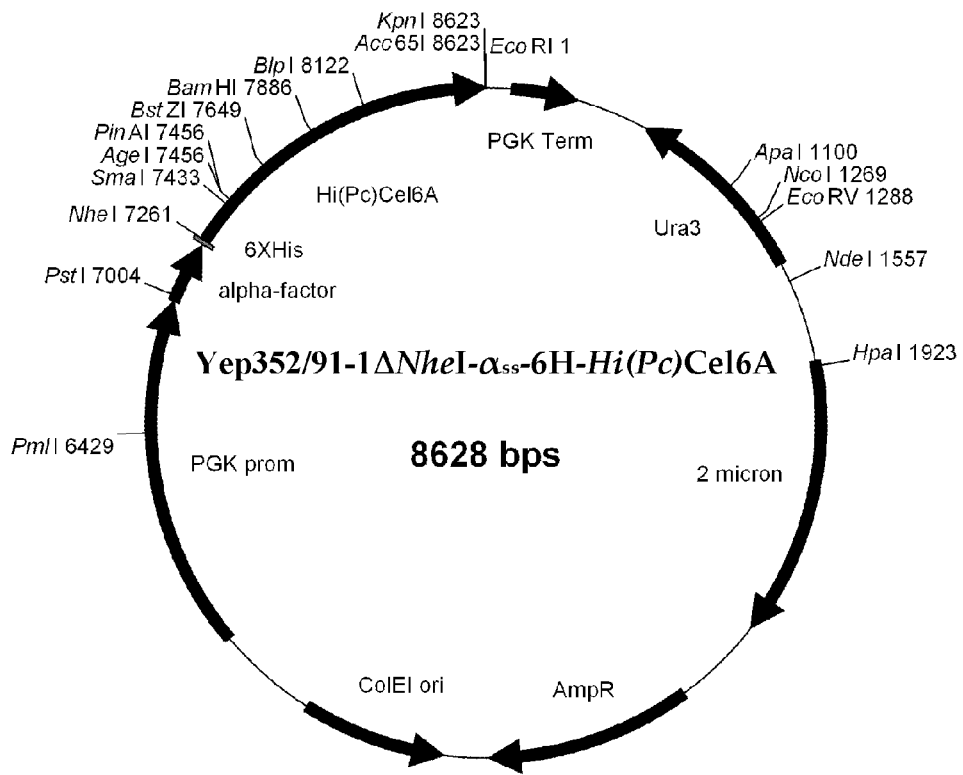
FIG. 3 depicts plasmid vector Yep352/91-1ΔNheI-α$_{ss}$-6H-Hi(Pc)Cel6A directing the expression and secretion of native and variant HiCel6A or PcCel6A from recombinant *Saccharomyces cerevisiae*.

The present invention relates to Family 6 cellulase variants. More specifically, the invention relates to Family 6 cellulase variants with reduced inhibition by glucose relative to the parental Family 6 cellulase from which it is derived. The present invention also relates to genetic constructs comprising nucleotide sequences encoding for Family 6 cellulase variants, methods for the production of Family 6 cellulase variants from host strains and the use of the Family 6 cellulase variants in the hydrolysis of cellulose.

The following description is of a preferred embodiment by way of example only and without limitation to the combination of features necessary for carrying the invention into effect.

DEFINITIONS

Family 6 Cellulase Variants

Family 6 (previously, Family B) cellulases enzymes are a group of enzymes that hydrolyse the beta-1,4 glucosidic linkages in cellulose with inversion of configuration of the anomeric carbon (Claeyssens, M. and Henrissat, B. 1992). Most of the Family 6 cellulases identified thus far are mesophilic. However, this family also includes thermostable cellulases from *Thermobifida fusca* (TfCel6A and TfCel6B of FIG. 1) and the alkalophilic cellulases from *Humicola insolens* (HiCel6A and HiCel6B of FIG. 1).

Figure 1:
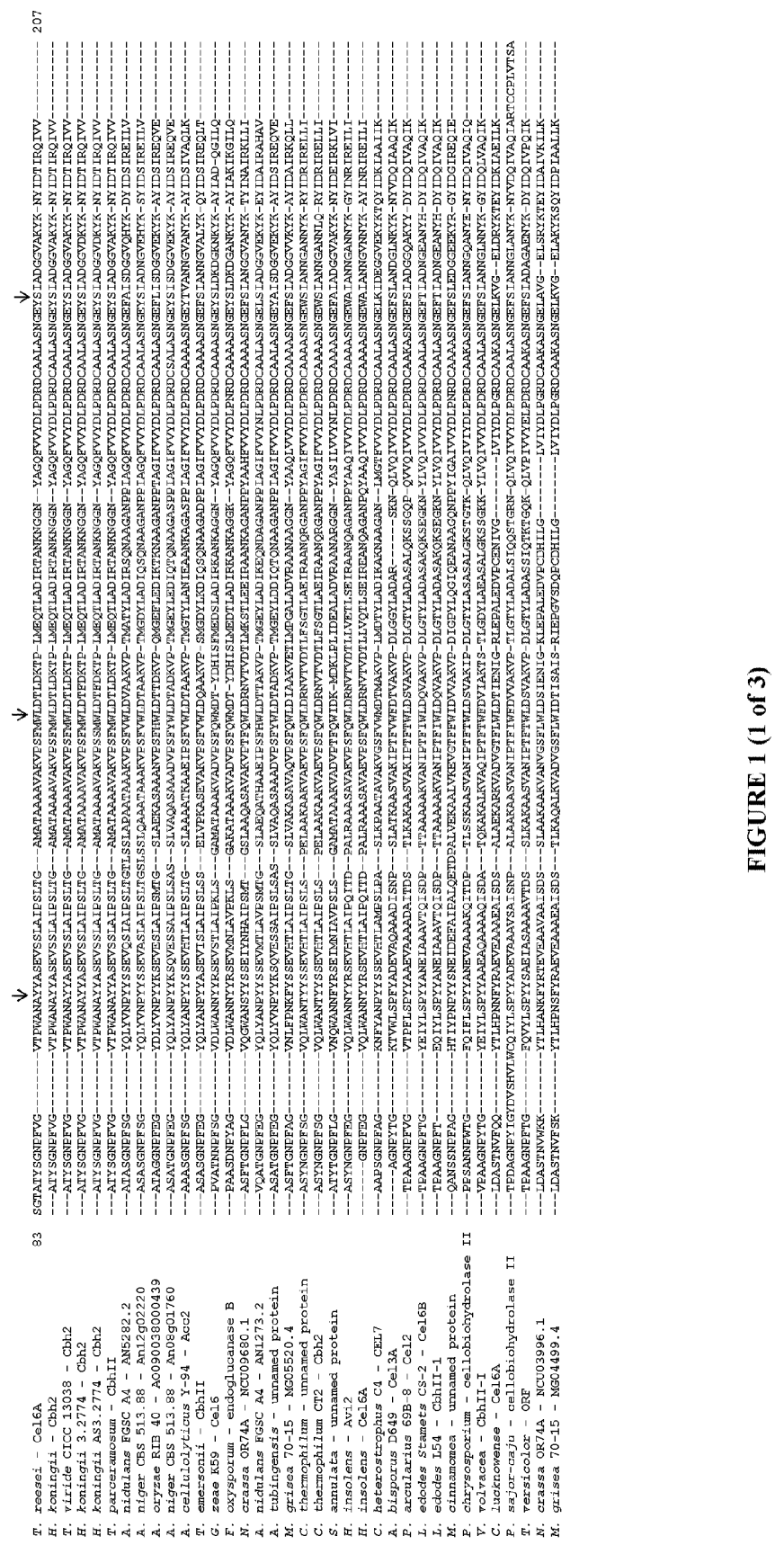
Figure 1:
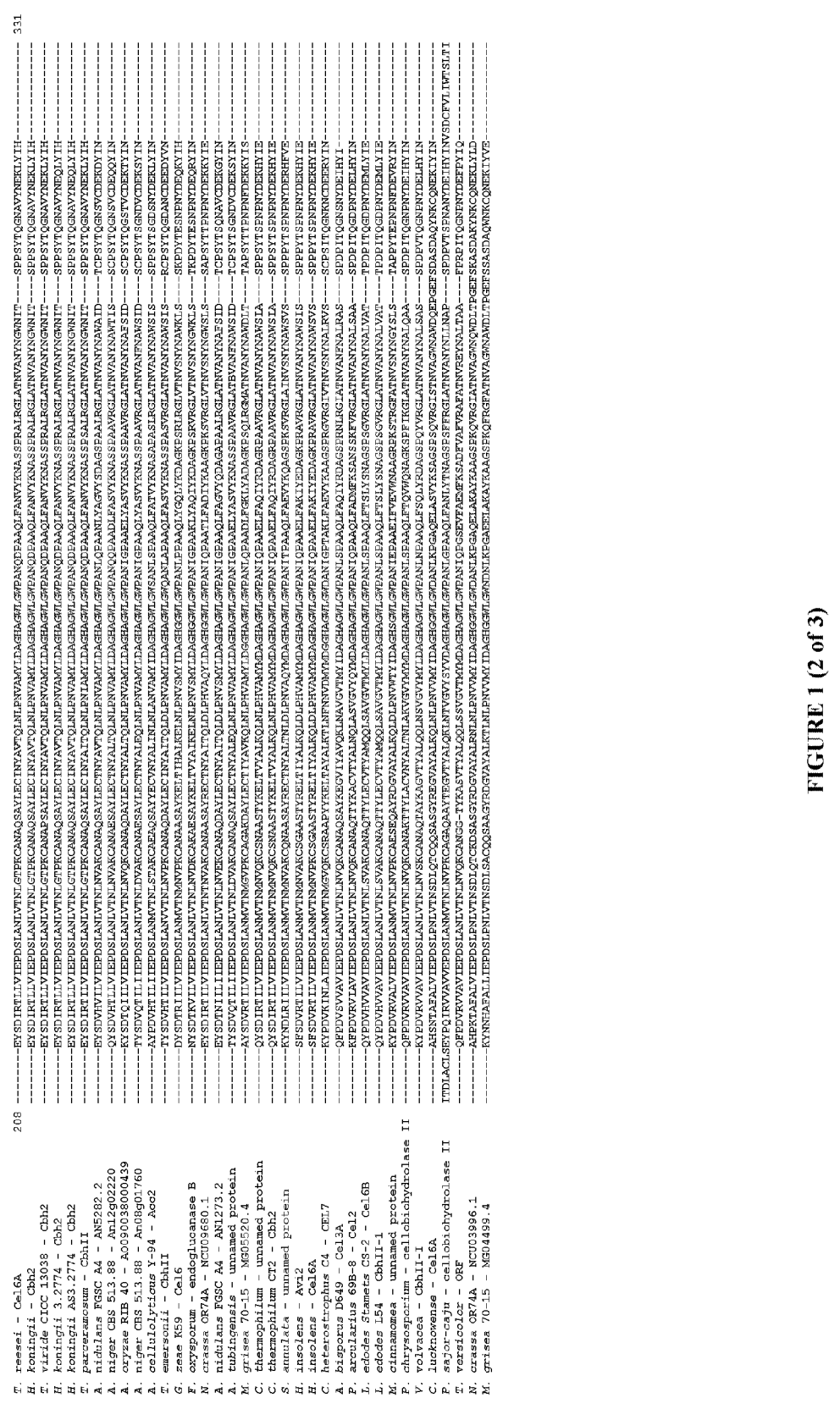
Figure 1:
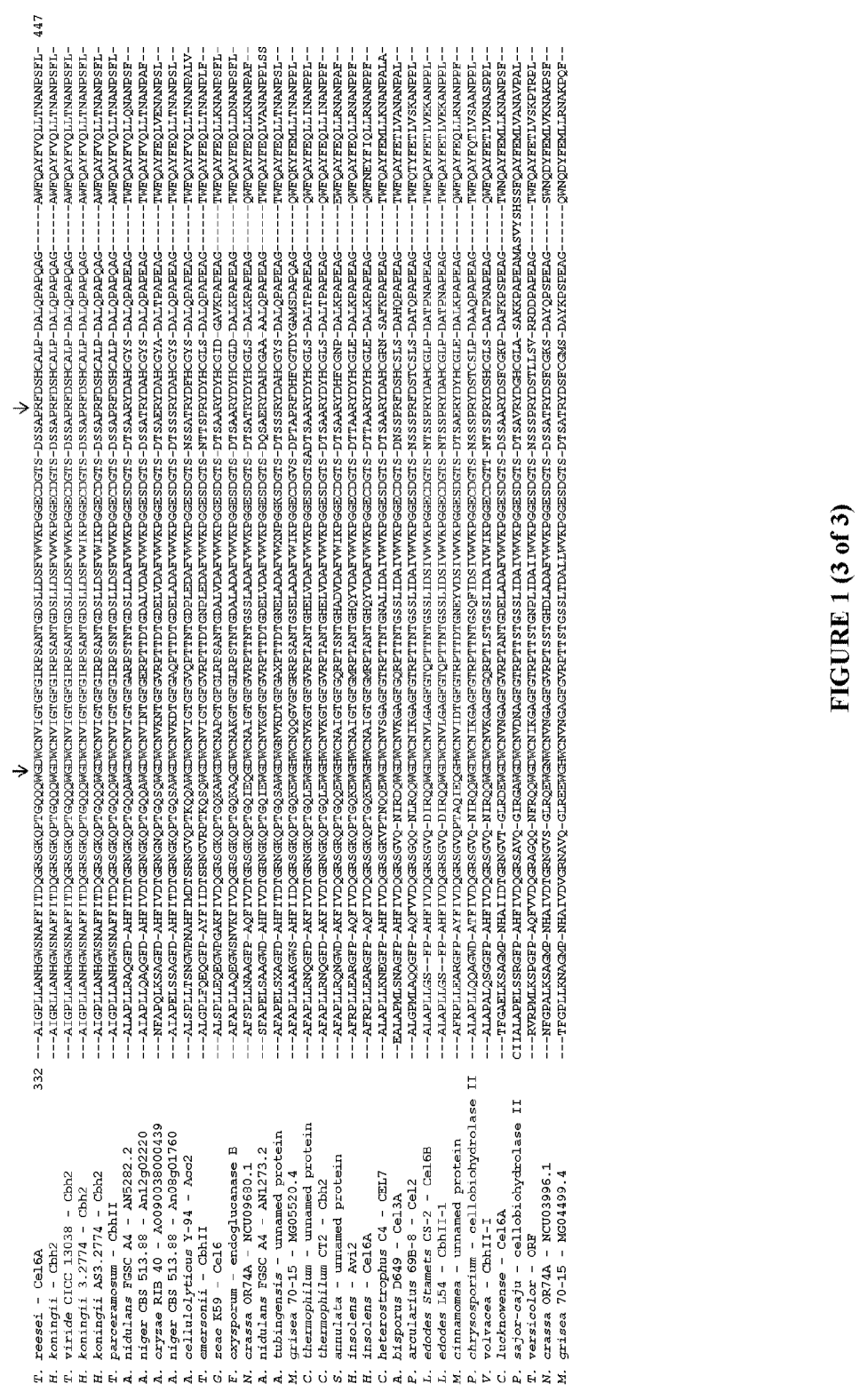

FIG. 1 and Table 1 show that there is a high degree of conservation of primary amino acid sequence among most of the cellulases of Family 6. Multiple alignment across 35 currently known Family 6 cellulase amino acid sequences shows that the most naturally occurring Family 6 cellulases of fungal origin show from about 47% to about 100% amino acid sequence identity to amino acids 83-447 of TrCel6A (FIG. 1 and Table 1); Family 6 cellulases of bacterial origin show a much lower degree of amino acid sequence identity to TrCel6A.

A cellulase is classified as a Family 6 cellulase if it comprises amino acids common to other Family 6 cellulase, including two aspartic acid (D) residues which may serve as catalytic residues. These aspartic acid residues are found at positions 175 and 221 (see FIG. 1; based on TrCel6A numbering). By "TrCel6A numbering", it is meant the numbering corresponding to the position of amino acids based on the amino acid sequence of TrCel6A (Table 1; FIG. 1; SEQ ID NO:1). As is evident by FIG. 1, Family 6 cellulases exhibit a substantial degree of sequence similarity. Therefore, by aligning the amino acids to optimize the sequence similarity between cellulase enzymes, and by using the amino acid numbering of TrCel6A as the basis for numbering, the positions of amino acids within other cellulase enzymes can be determined relative to TrCel6A. Methods to align amino acid sequences are well known and available to those of skill in the art and include BLAST (Basic Local Alignment Search Tool, see URL: blast.ncbi.nlm.nih.gov/Blast.cgi) which is useful for aligning two sequences and CLUSTALW (see URL: ebi-.ac.uk/Tools/clustalw2/index.html) for alignment of two or more sequences.

The conservation of overall three-dimensional structure provides further guidance to the alignment of the primary amino acid sequences of Family 6 cellulases. The topology of Family 6 catalytic domains is a variant of the α/β-barrel with a central β-barrel containing seven parallel β-strands connected by five α-helices. One important difference between Family 6 cellobiohydrolases and endo-β-1,4-glucanases is the length of their N- and C-terminal loops present on each side of the active site and which are responsible for their functional behavior on cellulose. In the cellobiohydrolases, an extensive C-terminal loop forms a tunnel with the N-terminal loop enclosing the active site. This confers the unique property of cellobiohydrolases to attack the ends of crystalline cellulose where the N- and C-terminal loops maintain a single cellulose chain in the active site and facilitate the processive degradation of the substrate. In the endo-β-1,4-glucanases, the C-terminal loop is reduced in length and the N-terminal loop pulls it away from the active site and could also be shorter resulting in a more open active site allowing access to internal β-1,4 glycosidic bonds of cellulose for hydrolysis. The role of these loops in the functional behavior of Family 6 enzymes on cellulose was confirmed by the deletion of fifteen amino acids of the C-terminal loop of the *Cellulomonas fimi* cellobiohydrolase Cel6B in order to mimic the properties of an endo-β-1,4-glucanase (Meinke, A., et al. 1995.). The mutation enhanced the endo-β-1,4-glucanase activity of the enzyme on soluble cellulose, such as carboxymethylcellulose, and altered its cellobiohydrolase activity on insoluble cellulose.

For the purpose of this invention, a "Family 6 cellulase" is defined as an enzyme capable of hydrolyzing polysaccharides using an inverting mechanism and characterized by having an α/β-barrel structure with a central β-barrel containing seven parallel β-strands connected by five α-helices an amino acid sequence that is from about 47% to about 100% identical to the amino acids 83 to 447 of SEQ ID NO:1, representing the Family 6 catalytic domain of TrCel6A. For example, a Family 6 cellulase may have an amino acid sequence that is about 47%, 50%, 55%, 60%, 65%, 70%, 75%, 80%, 85%, 90%, 95% or 100% identical to the amino acids 83-447 of SEQ ID NO: 1. One of skill in the art recognizes that the amino acid sequence of a given Family 6 cellulase may be modified by the addition, deletion or substitution of one or more amino acids and still be considered a Family 6 cellulase. Techniques for altering amino acid sequences include, but are not limited to, site-directed mutagenesis, cassette mutagenesis, random mutagenesis, synthetic oligonucleotide construction, cloning and other genetic engineering techniques as would be known by those of skill in the art (Eijsink V G, et al. 2005., which is incorporated herein by reference). Non-limiting examples of Family 6 cellulase that may be modified following the general approach and methodology as outlined herein are provided in Table 1.

TABLE 1

Family 6 Cellulases

| Organism | Protein | SEQ ID NO: | Identity with TrCel6A catalytic domain (83-447) (%) |
|---|---|---|---|
| Hypocrea koningii | cellobiohydrolase II (Cbh2) | 2 | 98.9 |
| Trichoderma viride CICC 13038 | cellobiohydrolase II (CbhII; Cbh2) | 3 | 98.9 |
| Hypocrea koningii 3.2774 | cellobiohydrolase II (Cbh2; CbhII) | 4 | 98.1 |
| Hypocrea koningii AS3.2774 | cbh2 | 5 | 97.8 |
| Trichoderma parceramosum | cellobiohydrolase II (CbhII) | 6 | 97.8 |
| Aspergillus nidulans FGSC A4 | cellobiohydrolase (AN5282.2) | 7 | 72.4 |
| Aspergillus niger CBS 513.88 | An12g02220 | 8 | 72.4 |
| Aspergillus oryzae RIB 40 | AO090038000439 | 9 | 67.8 |
| Aspergillus niger CBS 513.88 | An08g01760 | 10 | 67.7 |
| Acremonium cellulolyticus Y-94 | cellobiohydrolase II (Acc2) | 11 | 67.3 |
| Talaromyces emersonii | cellobiohydrolase II (CbhII) | 12 | 66.8 |
| Gibberella zeae K59 | Cel6-Cel6 | 13 | 66.1 |
| Fusarium oxysporum | endoglucanase B | 14 | 66.1 |
| Neurospora crassa OR74A | NCU09680.1 (64C2.180) | 15 | 65.9 |
| Aspergillus nidulans FGSC A4 | AN1273.2 | 16 | 65.5 |
| Aspergillus tubingensis | unnamed protein product (fragment) | 17 | 65.5 |
| Magnaporthe grisea 70-15 | MG05520.4 | 18 | 65.4 |
| Chaetomium thermophilum | unnamed protein product | 19 | 65.1 |
| Chaetomium thermophilum CT2 | cellobiohydrolase (Cbh2) | 20 | 65.0 |
| Stilbella annulata | unnamed protein product | 21 | 64.9 |
| Humicola insolens | avicelase 2 (Avi2) | 22 | 63.7 |
| Humicola insolens | cellobiohydrolase (CBHII)-Cel6A | 23 | 63.1 |
| Cochliobolus heterostrophus C4 | cellobiohydrolase II (CEL7) | 24 | 59.6 |
| Agaricus bisporus D649 | cellobiohydrolase II (Cel3; Cel3A) | 25 | 57.7 |
| Polyporus arcularius 69B-8 | cellobiohydrolase II (Cel2) | 26 | 57.1 |
| Lentinula edodes Stamets CS-2 | cellulase-Cel6B | 27 | 56.3 |
| Lentinula edodes L54 | cellobiohydrolase (CbhII-1) | 28 | 56.0 |
| Malbranchea cinnamomea | unnamed protein product | 29 | 54.9 |
| Phanerochaete chrysosporium | cellobiohydrolase II | 30 | 54.9 |
| Volvariella volvacea | cellobiohydrolase II-I (CbhII-I) | 31 | 53.8 |
| Chrysosporium lucknowense | cellobiohydrolase (EG6; CBH II)-Cel6A | 32 | 49.5 |
| Pleurotus sajor-caju | cellobiohydrolase II | 33 | 47.2 |
| Trametes versicolor | ORF | 34 | 47.0 |
| Neurospora crassa OR74A | NCU03996.1 | 35 | 46.8 |
| Magnaporthe grisea 70-15 | MG04499.4 | 36 | 45.1 |

By "Family 6 cellulase variant" or "modified Family 6 cellulase", it is meant a Family 6 cellulase which comprises one or more than one the following amino acid substitutions: the amino acid at position 103 has been replaced by a basic, non-polar or proline residue; the amino acid at position 136 has been replaced by a valine or isoleucine residue; the amino acid at position 186 has been replaced by a tyrosine or lysine residue; the amino acid at position 365 has been replaced by an acidic, glutamine or serine residue; or the amino acid at position 410 has been replaced by an alanine, phenylalanine, leucine, glutamine or serine residue; said position determined from sequence alignment of said isolated cellulase with a *Trichoderma reesei* Cel6A amino acid sequence as defined in SEQ ID NO:1. It will be understood that the Family 6 cellulase variant may be derived from any Family 6 cellulase. For example, the Family 6 cellulase variant may be derived from a wild-type cellulase or from a cellulase that already contains other amino acid substitutions. In one embodiment of the invention, the Family 6 cellulase variant exhibits reduced inhibition by glucose over the corresponding parental Family 6 cellulase from which it is derived.

By "wild type" or "native" Family 6 cellulase, it is meant a Family 6 cellulase having an amino acid sequence as encoded by the genome of the organism that naturally produces such Family 6 cellulase without the introduction of any substitutions, deletions, additions or modifications. For example, by wild type TrCel6A, wild type HiCel6A and wild type PcCel6A it is meant the cellulases of SEQ ID NO: 1, SEQ ID NO: 23 and SEQ ID NO: 30 respectively, without any amino acid substitutions.

By "parental Family 6 cellulase", it is meant a Family 6 cellulase that exhibits at least 1.4-fold less inhibition by glucose and comprises one or more naturally-occurring amino acid(s) at the mutated positions corresponding to that of the Family 6 cellulase variant, but that is otherwise identical to the Family 6 cellulase variant. The parental Family 6 cellulase does not include those cellulases in which the naturally-occurring amino acid at position 103 is a basic, non-polar or proline residue, the naturally occurring amino acid at position 136 is a valine or isoleucine residue, the naturally occurring amino acid at position 186 is a tyrosine or lysine residue, the naturally occurring amino acid at position 365 is an acidic, glutamine or serine residue, and/or the naturally occurring amino acid at position 410 is an alanine, phenylalanine, leucine, glutamine or serine residue. This definition encompasses parental Family 6 cellulases that contain one or more additional amino acid substitution at other positions that have been introduced by genetic engineering or other techniques, provided that these substitutions are also present in the corresponding Family 6 cellulase variant. For example, the parental cellulase may contain a mutation of the amino acid at position 413 (TrCel6A numbering) to a proline to confer increased thermostability.

TABLE 2

Family 6 cellulase variants

| Protein | SEQ ID NO: |
|---|---|
| TrCel6A-Y103A-S413P | 37 |
| TrCel6A-Y103H-S413P | 38 |
| TrCel6A-Y103K-S413P | 39 |
| TrCel6A-Y103L-S413P | 40 |
| TrCel6A-Y103M-S413P | 41 |
| TrCel6A-Y103P-S413P | 42 |
| TrCel6A-Y103R-S413P | 43 |
| TrCel6A-Y103V-S413P | 44 |
| TrCel6A-L136I-S413P | 45 |
| TrCel6A-L136V-S413P | 46 |
| TrCel6A-S186K-S413P | 47 |
| TrCel6A-S186Y-S413P | 48 |
| TrCel6A-G365D-S413P | 49 |
| TrCel6A-G365E-S413P | 50 |
| TrCel6A-G365Q-S413P | 51 |
| TrCel6A-G365S-S413P | 52 |
| TrCel6A-R410A-S413P | 53 |
| TrCel6A-R410F-S413P | 54 |
| TrCel6A-R410L-S413P | 55 |
| TrCel6A-R410Q-S413P | 56 |
| TrCel6A-R410S-S413P | 57 |
| TrCel6A-Y103L-L136I-S413P | 58 |
| TrCel6A-Y103L-S186Y-S413P | 59 |
| TrCel6A-Y103L-G365Q-S413P | 60 |
| TrCel6A-Y103L-R410Q-S413P | 61 |
| TrCel6A-L136I-S186Y-S413P | 64 |
| TrCel6A-L136I-G365Q-S413P | 65 |
| TrCel6A-L136I-R410Q-S413P | 66 |
| TrCel6A-S186Y-G365Q-S413P | 67 |
| TrCel6A-S186Y-R410Q-S413P | 68 |
| TrCel6A-G365Q-R410Q-S413P | 69 |
| TrCel6A-M134V-L136I-S413P | 62 |
| TrCel6A-L136I-L215I-S413P | 63 |
| TrCel6A-M134V-L136I-L215I-S413P | 71 |
| TrCel6A-Y103L-S186Y-G365Q-S413P | 70 |
| TrCel6A-Y103L-L136I-S186Y-G365Q-S413P | 72 |
| TrCel6A-Y103L-S186Y-G365Q-R410Q-S413P | 75 |

TABLE 2-continued

Family 6 cellulase variants

| Protein | SEQ ID NO: |
|---|---|
| TrCel6A-Y103L-L136I-S186Y-G365Q-R410Q-S413P | 77 |
| TrCel6A-L136I-S186Y-G365Q-R410Q-S413P | 76 |
| TrCel6A-Y103L-L136I-G365Q-R410Q-S413P | 74 |
| TrCel6A-Y103L-L136I-S186Y-R410Q-S413P | 73 |
| HiCel6A-Y107K | 78 |
| HiCel6A-Y107L | 79 |
| HiCel6A-Q139T | 80 |
| HiCel6A-L141V | 81 |
| HiCel6A-A194Y | 82 |
| PcCel6A-Y98K | 83 |
| PcCel6A-Y98L | 84 |
| PcCel6A-L131I | 85 |
| PcCel6A-L131V | 86 |
| PcCel6A-S182K | 87 |
| PcCel6A-S182Y | 88 |
| PcCel6A-G359Q | 89 |
| PcCel6A-R404Q | 90 |

Reduced Glucose Inhibition

Glucose inhibition of cellulases is measured by determination of the inhibition constant $K_G$, defined as the concentration of glucose which reduces the activity of the cellulase by 50%. The value of $K_G$ is not dependent on the nature of product inhibition—i.e., competitive, non-competitive or mixed-type. Cellulases that are less inhibited by glucose will have a higher value for $K_G$—i.e., it takes a higher concentration of glucose to reduce the enzyme activity by 50%.

For the purposes of the present invention, a Family 6 cellulase variant exhibits reduced glucose inhibition with respect to the corresponding parental Family 6 cellulase if it has a $K_G$ which is at least 1.4-fold, or at least about 1.8-fold, higher than that of the parental Family 6 cellulase. The $K_G$ is the concentration of glucose which reduces the activity of the isolated and parental Family 6 cellulases by 50% and is determined by the assay detailed in Example 9.

The Family 6 cellulase variant may have a $K_G$ which is about 1.4-fold higher than that of a corresponding parental Family 6 cellulase, or about 1.8-fold higher. For example, the Family 6 cellulase variant may have a $K_G$ that is at least about 1.4-, 1.5-, 1.6-, 1.8-, 2.0-, 2.5-, 3.0-, 3.5-, 4.0, 4.5-, 5.0-, 5.5-, 6.0-, 6.5-, 7.0-, 8.0-, 10.0-, 12.0-, 15.0- or 20.0-fold higher than that of the corresponding parental Family 6 cellulase.

Examples of Family 6 cellulase variants exhibiting reduced inhibition by glucose are shown in Table 2.

Genetic Constructs Encoding Family 6 Cellulase Variant

The present invention also relates to genetic constructs comprising a DNA sequence encoding the Family 6 cellulase variant operably linked to regulatory DNA sequences directing the expression and secretion of the Family 6 cellulase variant from a host microbe. By "regulatory DNA sequences" it is meant a promoter and a DNA sequence encoding a secretion signal peptide. The regulatory DNA sequences are preferably functional in a fungal host. The regulatory DNA sequences may be derived from genes that are highly expressed and secreted in the host microbe under industrial fermentation conditions. In a preferred embodiment, the regulatory sequences are derived from any one or more of the *Trichoderma reesei* cellulase or hemicellulase genes.

The genetic construct may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. In a preferred embodiment, the selectable marker gene confers resistance to hygromycin, phleomycin, kanamycin, geneticin, or G418, complements a deficiency of the host microbe in one of the trp, arg, leu, pyr4, pyr, ura3, ura5, his, or ade genes or confers the ability to grow on acetamide as a sole nitrogen source.

The genetic construct may further comprise other DNA sequences, for example, transcriptional terminators, DNA encoding peptide tags, synthetic sequences to link the various DNA sequences together, origins of replication, and the like. The practice of the present invention is not limited by the presence of any one or more of these other DNA sequences.

Genetically Modified Microbes Producing Family 6 Cellulase Variants

The Family 6 cellulase variant may be expressed and secreted from a genetically modified microbe produced by transformation of a host microbe with a genetic construct encoding the Family 6 cellulase variant. The host microbe may be a yeast or a filamentous fungus including, but not limited to, a species of *Saccharomyces, Pichia, Hansenula, Trichoderma, Hypocrea, Aspergillus, Fusarium, Humicola,* or *Neurospora*. For example, the host microbe may be *Saccharomyces cerevisiae* or an industrial strain of *Trichoderma reesei*. Typically, the host microbe is one which does not contain a gene encoding a Family 6 cellulase or from which the gene(s) encoding any or all Family 6 cellulases have been deleted.

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072, which is incorporated herein by reference). After selecting the recombinant fungal strains expressing the Family 6 cellulase variant, the selected recombinant strains may be cultured in submerged liquid fermentations under conditions that induce the expression of the Family 6 cellulase variant.

Figure 5:
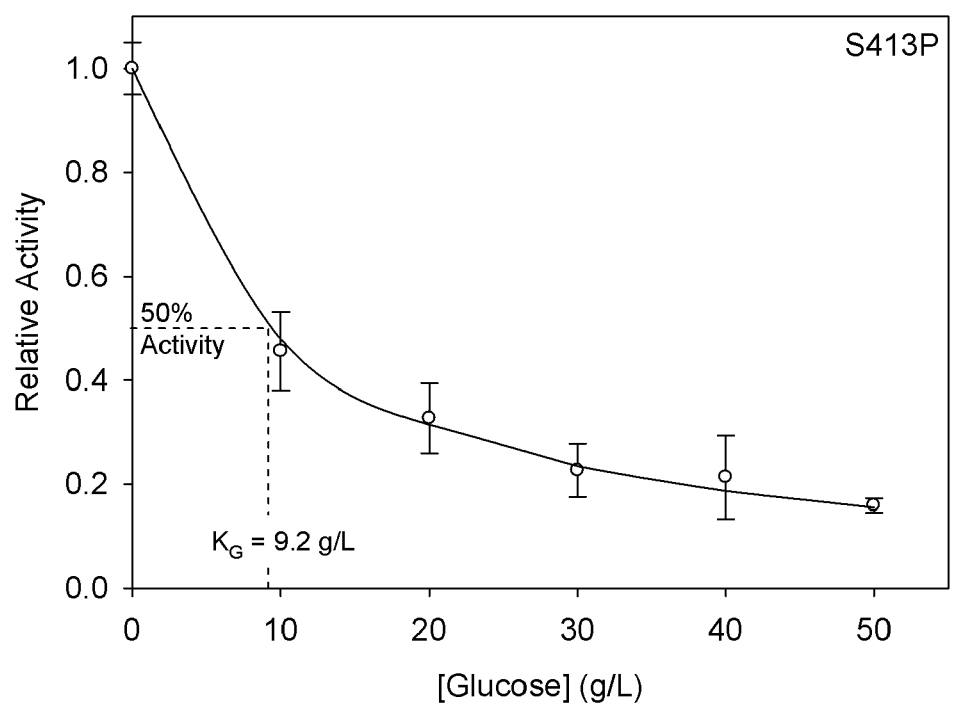
FIG. 5 shows the effect of increasing glucose concentration on the relative activity of the TrCel6A-S413P.
Figure 6:
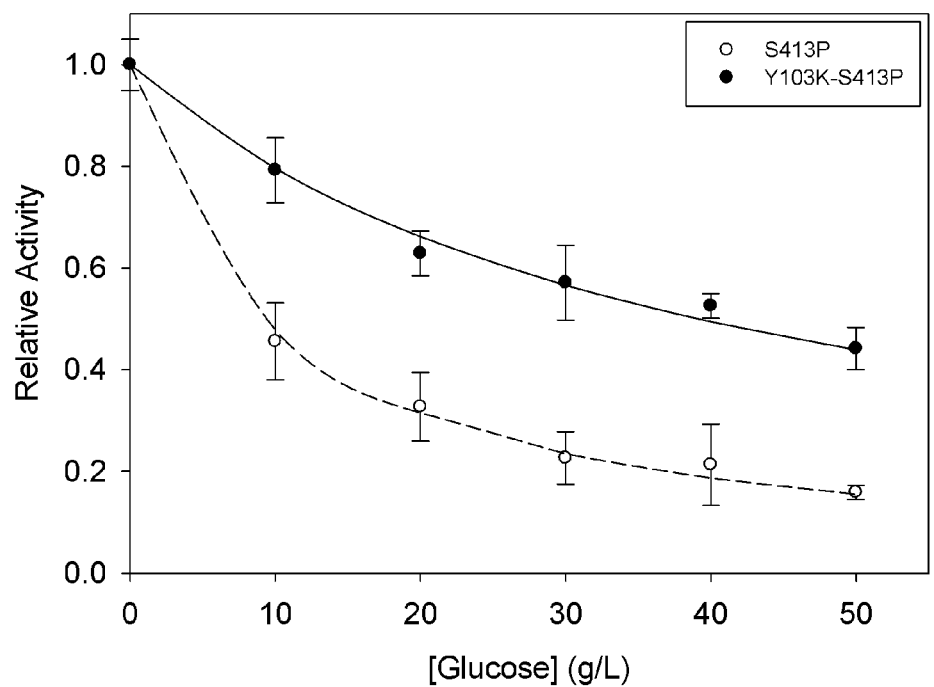
FIG. 6 shows the effect of increasing glucose concentration on the relative activity of the TrCel6A-S413P and TrCel6A-Y103K-S413P.
Figure 7:
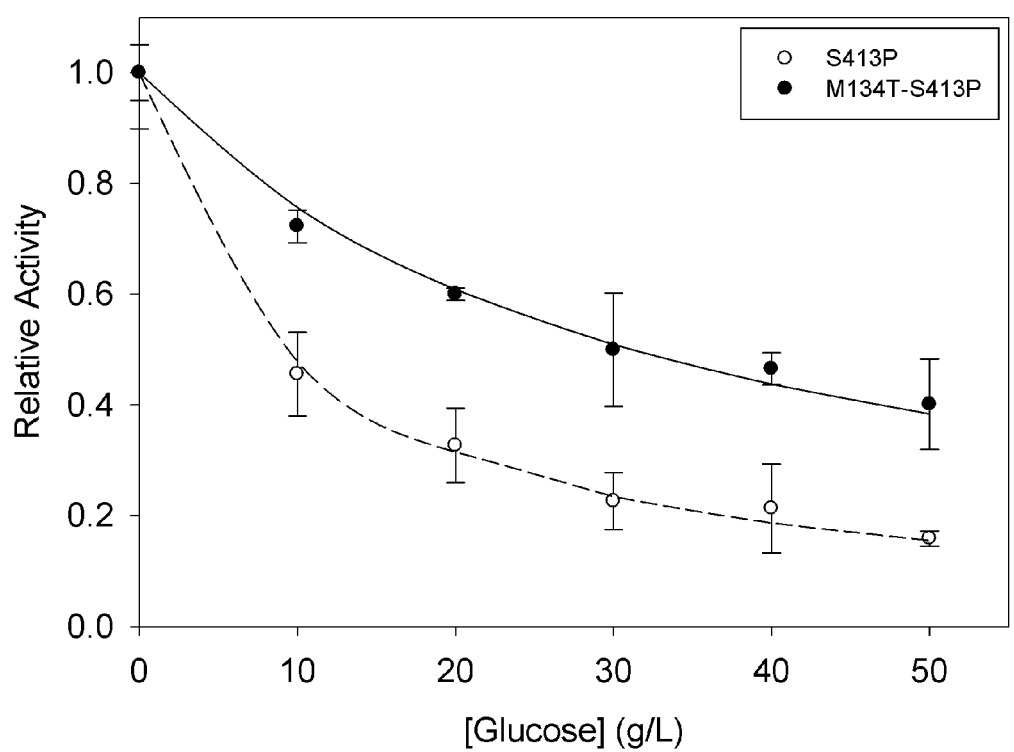
FIG. 7 shows the effect of increasing glucose concentration on the relative activity of the TrCel6A-S413P and TrCel6A-M134T-S413P.
Figure 8:
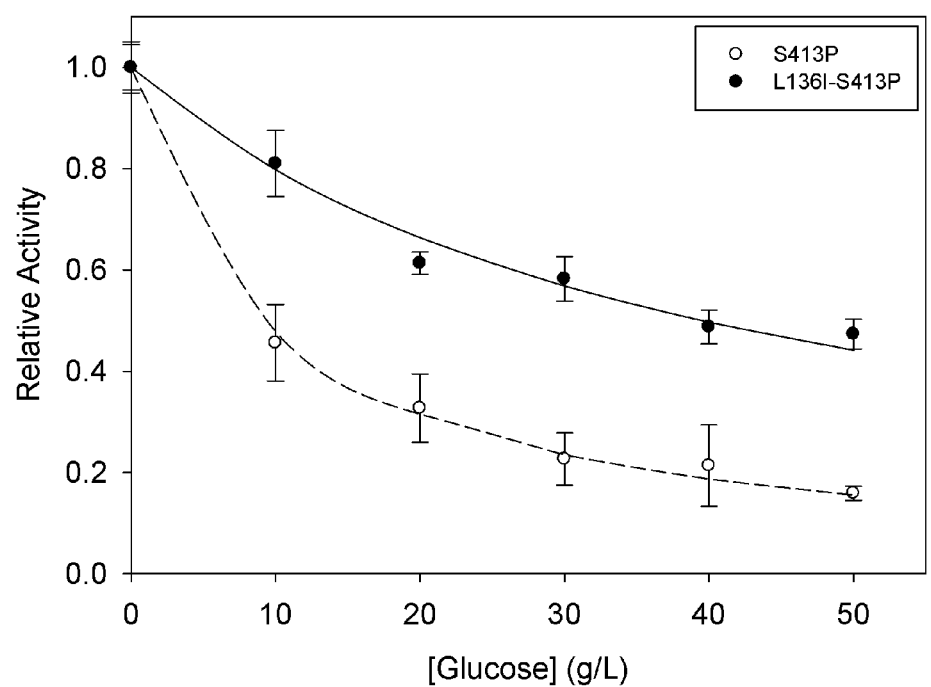
FIG. 8 shows the effect of increasing glucose concentration on the relative activity of the TrCel6A-S413P and TrCel6A-L136I-S413P.
Figure 9:
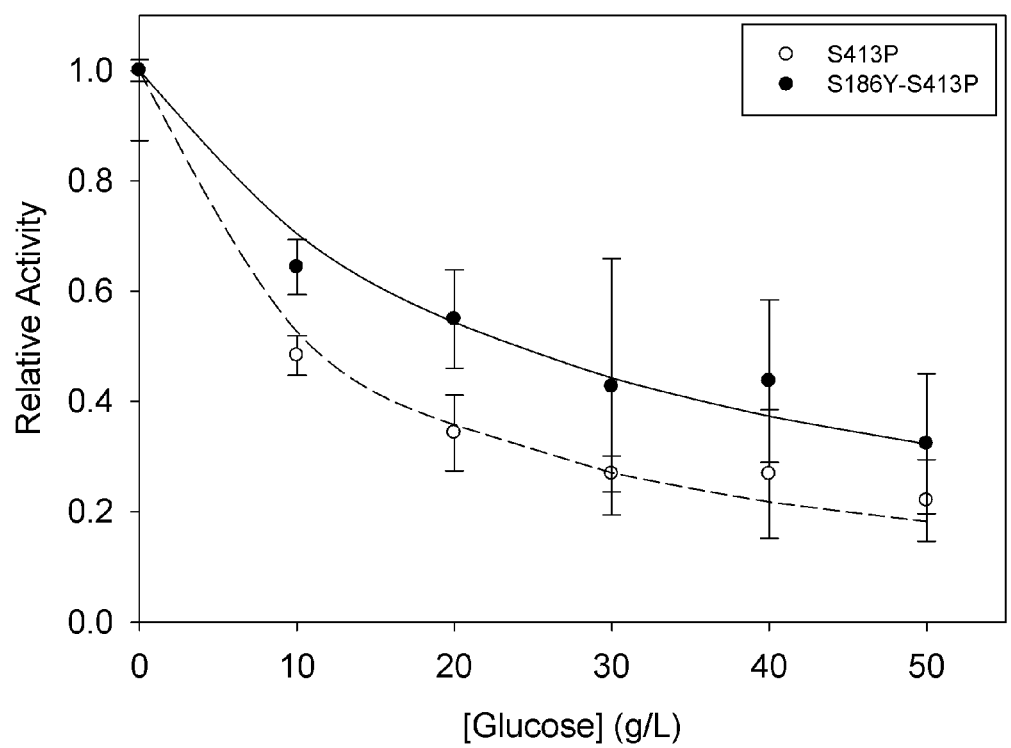
FIG. 9 shows the effect of increasing glucose concentration on the relative activity of the TrCel6A-S413P and TrCel6A-S186Y S413P.
Figure 10:
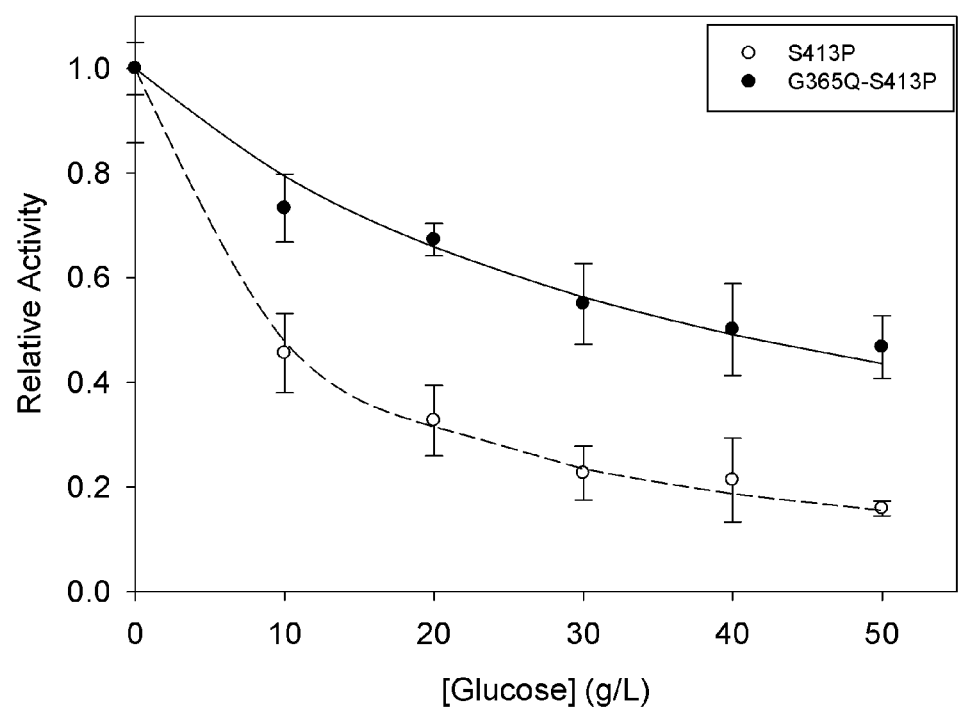
FIG. 10 shows the effect of increasing glucose concentration on the relative activity of the TrCel6A-S413P and TrCel6A-G365Q-S413P.
Figure 11:
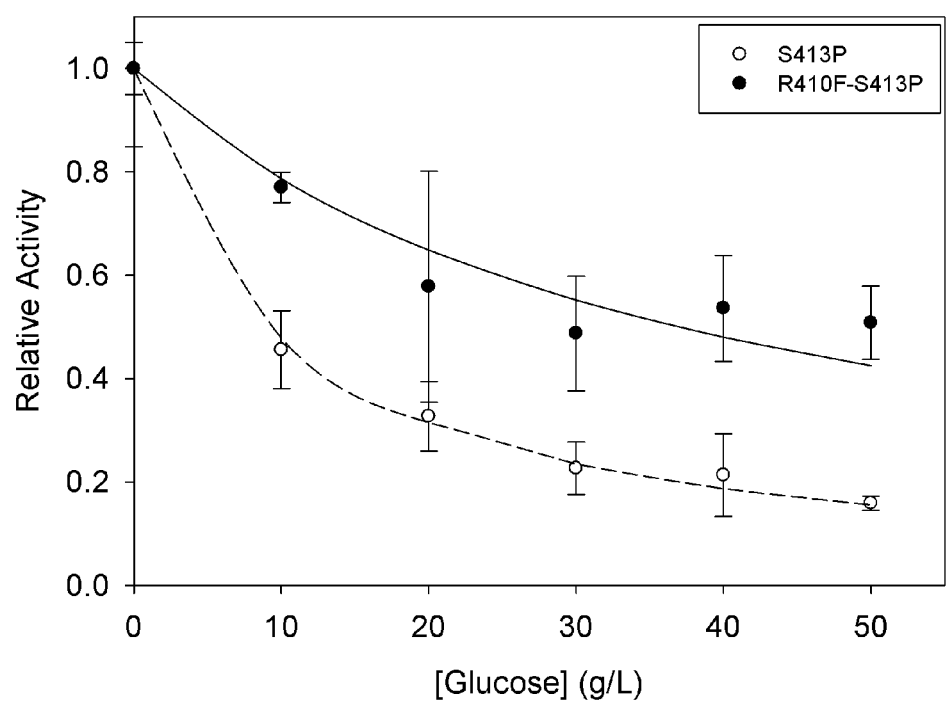
FIG. 11 shows the effect of increasing glucose concentration on the relative activity of the TrCel6A-S413P and TrCel6A-R410F-S413P.
Figure 12:
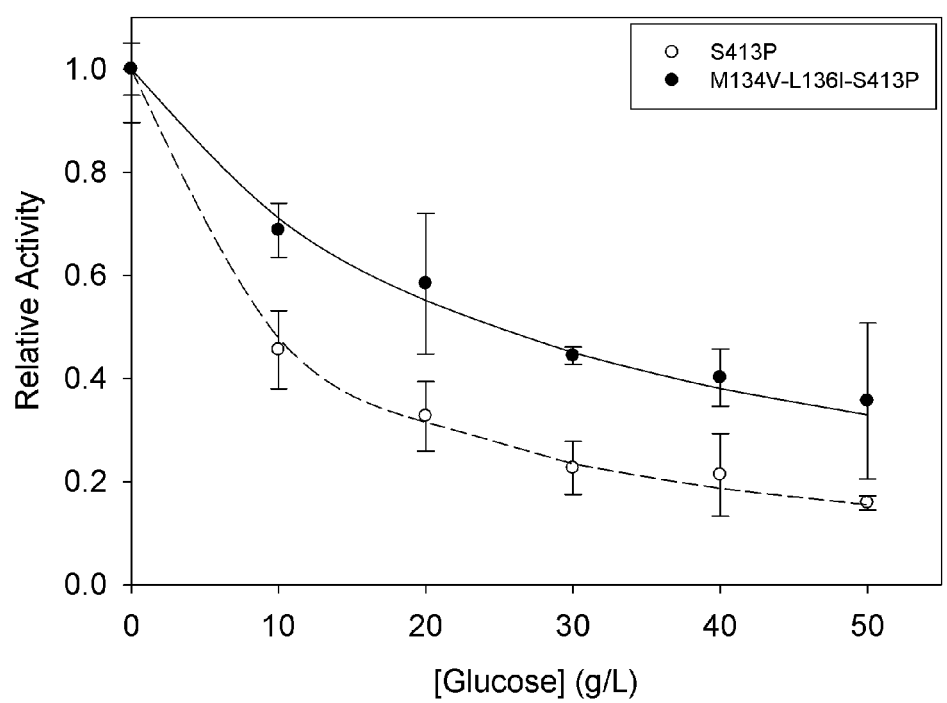
FIG. 12 shows the effect of increasing glucose concentration on the relative activity of the TrCel6A-S413P and TrCel6A-M134V-L136I-S413P.
Figure 13:
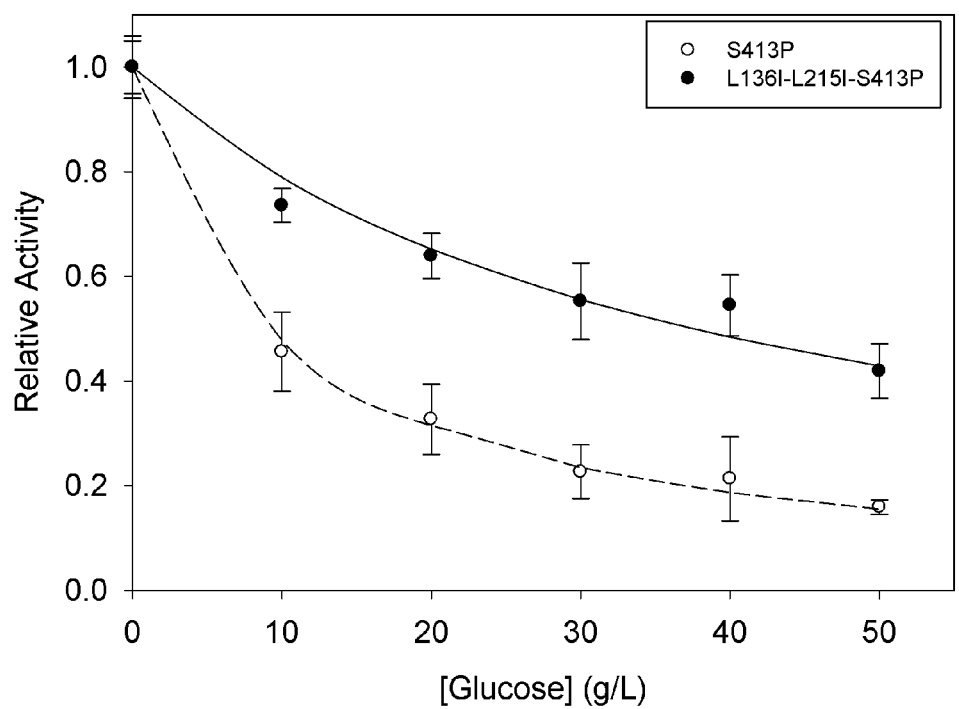
FIG. 13 shows the effect of increasing glucose concentration on the relative activity of the TrCel6A-S413P and TrCel6A-L136I-L215I-S413P.
Figure 14:
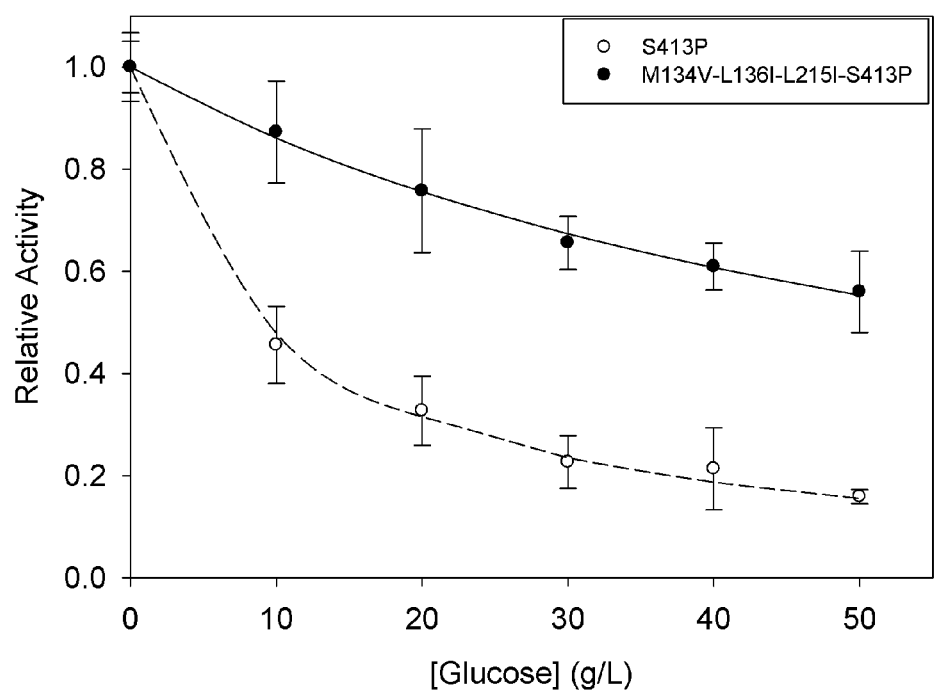
FIG. 14 shows the effect of increasing glucose concentration on the relative activity of the TrCel6A-S413P and TrCel6A-M134V-L136I-L215I-S413P.
Figure 15:
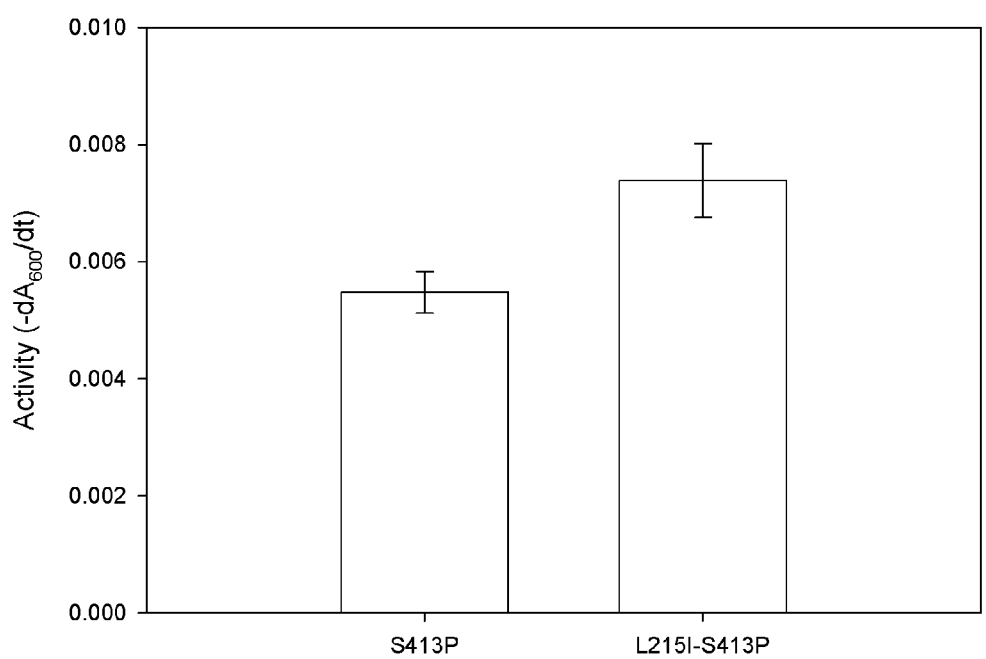
FIG. 15 shows the activity of TrCel6A-S413P and TrCel6A-L215I-S413P in the presence of 10 g/L glucose.

The Use of Family 6 Cellulase Variant in the Hydrolysis of Cellulosic Substrates The Family 6 cellulase variant of the invention is used for the enzymatic hydrolysis of cellulose. The Family 6 cellulase variants of the present invention are particularly useful for the hydrolysis of cellulose-containing substrates under conditions where an inhibitory level of glucose is present or accumulates. For example, the Family 6 cellulase variants of the present invention may be useful in processes in which the initial starting concentration of cellulose is about 20 g/L and in which about 50% of the cellulose will be converted to glucose or in which the initial starting concentration of cellulose are as high as about 200 g/L and in which about 5% of the cellulose will be converted to glucose. For example, the initial cellulose concentration may be 20, 30, 40, 50, 60, 80, 100, 120, 150 or 200 g/L and about 50%, 33%, 25%, 20%, 17%, 12%, 10%, 8%, 7% or 5% of the cellulose, respectively, is converted to glucose. In the case of using the parental TrCel6A-S413P in such processes, the concentration of glucose will therefore be similar to the $K_G$ of the enzyme and reduce its activity by about 50% (Table 5, FIG. 5).

For example, the Family 6 cellulase variant of the present invention may be used for the enzymatic hydrolysis of the cellulose present in "pretreated lignocellulosic feedstock." A pretreated lignocellulosic feedstock is a material of plant origin that, prior to pretreatment, contains at least 20% cellulose (dry wt) and at least 10% lignin (dry wt), and that has been subjected to physical and/or chemical processes to make the fiber more accessible and/or receptive to the actions of cellulolytic enzymes. After pretreatment, the lignocellulosic feedstock may contain greater than about 20% cellulose and greater than about 10% lignin. In one embodiment, the pretreated lignocellulosic feedstock contains greater than about 20% cellulose and greater than about 12% lignin. Non-limiting examples of pretreatment processes include chemical treatment of a lignocellulosic feedstock with sulfuric or sulfurous acid, or other acids; ammonia, lime, ammonium hydroxide, or other bases; ethanol, butanol, or other organic solvents; or pressurized water (See U.S. Pat. Nos. 4,461,648, 5,916,780, 6,090,595, 6,043,392, 4,600,590, Weil et al. (1997) and Öhgren, K., et al. (2005)).

Lignocellulosic feedstocks that may be used in the invention include, but are not limited to, agricultural residues such as corn stover, wheat straw, barley straw, rice straw, oat straw, canola straw, and soybean stover; fiber process residues such as corn fiber, sugar beet pulp, pulp mill fines and rejects or sugar cane bagasse; forestry residues such as aspen wood, other hardwoods, softwood, and sawdust; or grasses such as switch grass, miscanthus, cord grass, and reed canary grass. The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

By the term "enzymatic hydrolysis", it is meant a process by which cellulase enzymes or mixtures, including those comprising the Family 6 cellulase variant of the present invention, act on cellulose to convert all or a portion thereof to soluble sugars. By the term "cellulase mixture", it is meant a mixture of enzymes which decomposes cellulose and comprises one or more "endoglucanases", enzymes that hydrolyze beta-1,4 glycosidic bonds within cellulose chains, "cellobiohydrolases" or "exoglucanases", enzymes that sequentially cleave cellobiose from either the reducing or non-reducing end of a cellulose chain, and one or more "beta-glucosidases", enzymes that hydrolyzes cellobiose to glucose. A cellulase mixture may contain other enzymes or proteins in addition to endoglucanases, cellobiohydrolases and beta-glucosidases.

The enzymatic hydrolysis process preferably converts about 80% to about 100% of the cellulose to soluble sugars, or any range therebetween. For example, the enzymatic hydrolysis process converts about 90% to about 100% of the cellulose to soluble sugars, or any range therebetween. In a preferred embodiment, the enzymatic hydrolysis process converts about 98% to about 100% of the cellulose to soluble sugars, or any range therebetween.

Preferably, the primary cellulases are produced in one or more submerged liquid culture fermentations and separated from the cells at the end of the fermentation. The cells may be separated from the cellulases by filtration, centrifugation, or other processes familiar to those skilled in the art. The cell-free cellulase-containing fraction may then be concentrated (for example, via ultrafiltration), preserved, and/or stabilized prior to use. Alternatively, the primary cellulases are not separated from the cells, but are added to the enzymatic hydrolysis with the cells.

Decreasing the Glucose Inhibition of Family 6 Cellulases

The glucose inhibition constants of the Family 6 cellulase variants were determined by incubation of the enzyme in the presence of substrate at various concentrations of glucose. Activity of the cellulase was determined via a turbidometric assay with insoluble acid swollen cellulose as a substrate. By "turbidometric assay" it is meant an assay of the optical density of a suspension of particulates in a fluid, in which the fraction of incident light which is not scattered by the particles, and therefore directly transmitted through the suspension, is measured. "Nepholometry" is a related technique which measures the fraction of light which is scattered by the particles, typically from an observation angle of 90 degrees from the incident light.

The effect of amino acid substitutions at positions 103, 136, 186, 365 and 410, in combination with each other or with additional amino acid substitutions at positions 134 and 215 on the glucose tolerance of TrCel6A with substitution of the serine at position 413 with proline, was determined via a comparative study of variants of the parental Family 6 cellulases TrCel6A-S413P, HiCel6A and PcCel6A.

The absolute values of $K_G$ for the Family 6 cellulase variants and the relative reductions in glucose inhibition over the parental Family 6 cellulase are shown in Table 3, below:

TABLE 3

Reduced Glucose Inhibition of Family 6 cellulase variants

| Amino Acid Substitution | SEQ ID No: | $K_G$ (g/L) | Relative $K_G$ |
|---|---|---|---|
| None (TrCel6A-S413P) | 156 | 9.2 | 1.00 |
| Y103A | 37 | 25.1 | 2.73 |
| Y103H | 38 | 21.0 | 2.28 |
| Y103K | 39 | 39.1 | 4.26 |
| Y103L | 40 | 32.0 | 3.48 |
| Y103M | 41 | 26.0 | 2.83 |
| Y103P | 42 | 26.8 | 2.91 |
| Y103R | 43 | 24.2 | 2.63 |
| Y103V | 44 | 26.2 | 2.85 |
| M134I | 157 | 31.7 | 3.45 |
| M134Q | 158 | 23.7 | 2.58 |
| M134T | 159 | 31.2 | 3.39 |
| M134V | 160 | 24.6 | 2.67 |
| M134Y | 161 | 23.4 | 2.54 |
| L136I | 45 | 39.5 | 4.29 |
| L136V | 46 | 24.9 | 2.71 |
| S186K | 47 | 19.9 | 2.16 |
| S186Y | 48 | 23.8 | 2.59 |
| G365D | 49 | 17.6 | 1.91 |
| G365E | 50 | 21.1 | 2.29 |
| G365Q | 51 | 38.7 | 4.20 |
| G365S | 52 | 29.8 | 3.23 |
| R410A | 53 | 25.0 | 2.72 |
| R410F | 54 | 37.0 | 4.02 |
| R410L | 55 | 49.5 | 5.38 |
| R410Q | 56 | 37.8 | 4.11 |
| R410S | 57 | 24.5 | 2.66 |
| M134V-L136I | 62 | 48.6 | 5.28 |
| L136I-L215I | 63 | 37.5 | 4.08 |
| M134V-L136I-L215I | 71 | 61.9 | 6.73 |
| *H. insolens* HiCel6A wildtype | 23 | 31.9 | 1.00 |
| Y107K | 78 | 45.5 | 1.43 |
| Y107L | 79 | 61.0 | 1.91 |
| Q139T | 80 | 51.9 | 1.62 |
| L141V | 81 | 54.6 | 1.71 |
| A194Y | 82 | 63.2 | 1.98 |
| *P. chrysosporium* wildtype | 30 | 20.3 | 1.00 |
| Y98K | 83 | 65.5 | 3.22 |
| Y98L | 84 | 31.9 | 1.57 |
| L131I | 85 | 32.9 | 1.62 |
| L131V | 86 | 33.3 | 1.64 |
| S182K | 87 | 39.7 | 1.95 |
| S182Y | 88 | 46.4 | 2.28 |

TABLE 3-continued

Reduced Glucose Inhibition of Family 6 cellulase variants

| Amino Acid Substitution | SEQ ID No: | $K_G$ (g/L) | Relative $K_G$ |
|---|---|---|---|
| G359Q | 89 | 35.2 | 1.73 |
| R404Q | 90 | 47.4 | 2.33 |

By "relative $K_G$" it is mean the ratio of the absolute $K_G$ of the Familiy 6 cellulase variant by the absolute $K_G$ of the parental Family 6 cellulase from which the Family 6 cellulase variant is derived. As such, the Family 6 cellulase variant is said to exhibit "-fold" less inhibition by glucose than the parental Family 6 cellulase from which it is derived. For example, as shown in Table 3 the Y98K variant of the *P. chrysosporium* Family 6 cellulase exhibits a relative $K_G$ of 3.22 and is therefore 3.22-fold less inhibited by glucose than the parental, wild-type *P. chrysosporium* Family 6 cellulase from which the Y98K variant is derived.

EXAMPLES

The present invention will be further illustrated in the following examples. However, it is to be understood that these examples are for illustrative purposes only and should not be used to limit the scope of the present invention in any manner.

Example 1 describes the strains and vectors used in the following examples. Examples 2-5 describe the cloning of the TrCel6A-S413P gene and transformation in yeast, the making of error prone-PCR and site-saturation mutagenesis libraries of Cel6A, and the generation of combinatorial mutants. Examples 6 and 7 describe the expression of TrCel6A-S413P variants from microculture and the high-throughput screening to identify Family 6 cellulase variants with reduced inhibition by glucose. Examples 8 and 9 describe the expression and characterization of isolated and parental Family 6 cellulases with reduced inhibition by glucose. Examples 10-14 describe the construction, expression, purification, and characterization of PcCel6A-His6 and HiCel6A-His6 and their variants. Example 15 describes an immunoassay for measuring the concentration of TrCel6A variants.

Example 1

Strains and Vectors

*Saccharomyces cerevisiae* strain YDR483W BY4742 [14317] (MATα his3Δ1 leu2Δ0 lys2Δ0 ura3Δ0 Akre2) was obtained from ATCC (#4014317). *Humicola insolens* and *Phanerochaete chrysosporium* strains were obtained from ATCC® (#22082™ and #201542™, respectively). *Escherichia coli* strain DH5α (F φ80lacZΔM15 Δ(lacZYA-argF) U169 recA1 endA1 hsdR17($r_k^-$, $m_k^+$) phoA supE44 thi-1 gyrA96 relA1λ⁻) was obtained from Invitrogen. The YEp352/PGK91-1 vector was obtained from the National Institute of Health. The YEpFLAGΔKpn 10-S413P vector is described in U.S. Patent Application 60/841,507. The YEp-FLAG-1 vector was obtained from Sigma as a part of the Amino-Terminal Yeast FLAG Expression Kit. The pGEM T-easy vector was obtained from Promega.

Example 2

Cloning of the TrCel6A-S413P Gene into the YEp352/PGK91-1 and Transformation in Yeast In order to facilitate cloning using NheI and KpnI restriction enzymes, the unique NheI site at position 1936 of the YEp352/PGK91-1 vector was blunted using the DNA Polymerase I large (Klenow) fragment to generate YEp352/PGK91-1ΔNheI. The TrCel6A-S413P gene was amplified by PCR from YEpFLAGΔKpn 10-S413P vector (U.S. Application No. 60/841,507) using primers 5'NheCel6A and 3'BglKpnCel6A. In parallel, the yeast α-factor leader sequence was amplified by PCR from the YEpFLAG-1 vector (Sigma) using primers (5'BglAlphaSS and 3'NheAlphaSS) to introduce restriction sites for BglII at the 5' end and NheI at 3' end of the amplicon.

The yeast α-factor leader sequence was isolated by BglII/NheI digestion and a three piece ligation performed with the TrCel6A-S413P gene (isolated by NheI/BglII digestion) and YEp352/PGK91-1ΔNheI vector (isolated by BglII digestion). The resulting vector YEp352/PGK91-1ΔNheI-α$_{ss}$-TrCel6A-S413P (FIG. 2) was transformed in yeast strain BY4742 using the procedure described by Gietz, R. D. and Woods, R. A. (2002). Primer sequences are listed below:

```
5'BglAlphaSS:
                                            (SEQ ID NO: 91)
5'ACC AAA AGA TCT ATG AGA TTT CCT TCA ATT 3'NheAlphaSS:
                                            (SEQ ID NO: 92)
5'TGA GCA GCT AGC CCT TTT ATC CAA AGA TAC 5'NheCel6A:
                                            (SEQ ID NO: 93)
5'AAA AGG GCT AGC TGC TCA AGC GTC TGG GGC 3'BglKpnCel6A:
                                            (SEQ ID NO: 94)
5'GAG CTC AGA TCT GGT ACC TTA CAG GAA CGA TGG GTT
```

Example 3

Making Error Prone-PCR Libraries

Random mutagenesis libraries were generated using two methods: a Mutazyme® II DNA polymerase method and a Mn$^{2+}$/biased dNTP mix method. For the Mutazyme® II DNA polymerase method, a series of four independent PCR were performed using 10, 20, 30, and 40 ng of YEp352/PGK91-1ΔNheI-α$_{ss}$-TrCel6A-S413P vector and the Mutazyme® II DNA polymerase with primers YalphaN21 and 3'PGK-term. The amplification was done for 25 cycles. The four PCR products were pooled and diluted to 10 ng/μL. A second PCR mutagenesis step was performed using 30 ng of pooled PCR product with Mutazyme® II DNA polymerase using the same primers for 30 amplification cycles. The YEp352/PGK91-1ΔNheI-α$_{ss}$-TrCel6A-S413P vector was digested with NheI and KpnI and the empty vector fragment was isolated. This linear fragment and the final amplicon were transformed simultaneously and cloned by in vivo recombination into yeast strain BY4742 (Butler et al., 2003).

For the Mn$^{2+}$/biased dNTP mix method, a PCR was performed using 25 ng YEp352/PGK91-1ΔNheI-α$_{ss}$-TrCel6A-S413P vector, 200 μM dATP, 200 μM dCTP, 240 μM dGTP, 200 μM dTTP, and 640 μM Mn$^{2+}$ with Taq DNA polymerase (Sigma) with primers YalphaN21 and 3'PGK-term for 30 amplification cycles. The final amplicon was cloned into YEp352/PGK91-1ΔNheI-α$_{ss}$-TrCel6A-S413P vector as described above.

```
YalphaN21:
5'AGC ACA AAT AAC GGG TTA TTG         (SEQ ID NO: 95)

3'PGK-term:
5'GCA ACA CCT GGC AAT TCC TTA CC      (SEQ ID NO: 96)
```

Example 4

Making Site-Saturation Mutagenesis Libraries

Seven amino acid positions in TrCel6A-S413P (M134, L136, L215, Y103, S186, G365, and R410), identified during high-throughput screening (Example 7), were chosen for site-saturation mutagenesis in order to find an amino acid which further improves the tolerance to glucose. Site-saturation mutagenesis was performed by megaprimer PCR (two-step PCR reaction) using NNS primers (listed below), the YEp352/PGK91-1ΔNheI-α$_{ss}$-TrCel6A-S413P vector as template, and the Platinum® Taq DNA Polymerase High Fidelity (Invitrogen). The first-step PCR was done using the NNS primer and the complementary external primer (YalphaN21 or 3'PGK-term). The purified amplicon served as a megaprimer for the second-step PCR and the other complementary external primers were used to amplify the complete mutated gene. This final amplicon was then cloned into YEp352/PGK91-1ΔNheI-α$_{ss}$-TrCel6A-S413P vector as described in Example 3.

```
3'M134X:
                                            (SEQ ID NO: 97)
5'GAG TAT CTA GCC ASN NAA AAG AGG GAA C

3'L136X:
                                            (SEQ ID NO: 98)
5'CTT GTC AAG AGT ATC SNN CCA CAT AAA AG

3'L215X:
                                            (SEQ ID NO: 99)
5'GCT CAA TAA CCA GSN NGG TCC GGA TAT C

3'Y103X:
                                            (SEQ ID NO: 100)
5'CTT CAG AGG CGT ASN NTG CAT TGG CCC

3'S186X:
                                            (SEQ ID NO: 101)
5'CAC CAT CGG CAA TSN NGT ATT CGC CAT TC

5'G365X:
                                            (SEQ ID NO: 102)
5'CAG CAA CAG TGG NNS GAC TGG TGC AAT G

5'R410X:
                                            (SEQ ID NO: 103)
5'GAC AGC AGT GCG CCA NNS TTT GAC CCC CAC TGT GC
```

Example 5

Making Combinatorial Mutants

Based on the TrCel6A-S413P positive variants identified in Example 7 for tolerance to glucose, a set of three multiple mutants and one single mutant were designed over the parent TrCel6A-S413P (M134V-L136I, L136I-L215I, M134V-L136I-L215I, and M134V). For the M134V-L136I mutant, the YEp352/PGK91-1ΔNheI-α$_{ss}$-TrCel6A-S413P vector served as a template for a megaprimer PCR two-step reaction using the mutagenic primer 5'M134V-L136I, the external primer 3'PGK-term, and the Platinum® Taq DNA Polymerase High Fidelity (Invitrogen). The purified amplicon served as a megaprimer for the second-step PCR and the YalphaN21 external primers are used to amplified the complete mutated gene. This final amplicon and the purified YEp352/PGK91-1ΔNheI-α$_{ss}$-TrCel6A-S413P vector digested with XhoI and NruI were transformed simultaneously and cloned by in vivo recombination into yeast strain BY4742. For the L136I-L215I mutant, the NheI-EcoRV purified fragment and the purified YEp352/PGK91-1ΔNheI-α$_{ss}$-TrCel6A-S413P-L215I vector (isolated in Example 7) digested with XhoI and NruI were transformed simultaneously and cloned by in vivo recombination into yeast strain BY4742. For the M134V-L136I-L215I mutant, the purified megaprimer described above and the purified YEp352/PGK91-1ΔNheI-α$_{ss}$-TrCel6A-S413P-L215I vector (isolated in Example 7) digested with XhoI and NruI were transformed simultaneously and cloned by in vivo recombination into yeast strain BY4742. Finally, for the M134V mutant, the YEp352/PGK91-1ΔNheI-α$_{ss}$-TrCel6A-S413P vector served as a template for a megaprimer PCR two-step reaction using the mutagenic primer 5'M134V, the external primer 3'PGK-term, and the Platinum® Taq DNA Polymerase High Fidelity (Invitrogen). The purified amplicon served as a megaprimer for the second-step PCR and the YalphaN21 external primers are used to amplified the complete mutated gene. This final amplicon and the purified YEp352/PGK91-1ΔNheI-α$_{ss}$-TrCel6A-S413P vector digested with XhoI and NruI were transformed simultaneously and cloned by in vivo recombination into yeast strain BY4742.

```
5'M134V-L136I:
                                          (SEQ ID NO: 104)
5'GTT CCC TCT TTT GTG TGG ATA GAT ACT CTT GAC

5'M134V:
                                          (SEQ ID NO: 105)
5'GTT CCC TCT TTT GTG TGG CTA GAT ACT
```

Example 6

Expression and Isolation of TrCel6A-S413P and its Variants from Microplate Cultures This example describes the selection and expression of TrCel6A-S413P variants from *Saccharomyces cerevisiae* for use in a high-throughput screening assay (Example 7).

*Saccharomyces cerevisiae* transformants, from Example 2-5, were grown on plates containing synthetic complete medium (SC: 2% agar w/v, 0.17% yeast nitrogen base w/v, 0.078%-Ura drop-out supplement w/v, 2% glucose w/v, 2% casamino acids w/v, 0.5% ammonium sulfate w/v, pH 5.5) and 0.12% Azo-barley-β-glucan (Megazyme) for 4 days at 30° C.

Colonies showing visible clearing halos, after an overnight incubation at 45° C., were selected for liquid media pre-cultures by toothpick inoculation of 150 μL synthetic complete media (SC: 0.17% yeast nitrogen base w/v, 0.078%-Ura drop-out supplement w/v, 2% glucose w/v, 2% casamino acids w/v, 0.5% ammonium sulfate w/v, pH 5.5) in 96-well microplates. Pre-cultures were grown overnight (16-18 hr) at 30° C. and 300 rpm to stationary phase. For expression culture inoculation, 25 μL of pre-culture was used to inoculate 1 mL of SC media in deepwell microplates containing one glass bead. Expression cultures were grown for 3 days at 30° C. and 250 rpm with humidity control. Plates were centrifuged at 3000 rpm for 5 minutes to pellet cells and supernatant was aspirated for screening assays (Example 7). To the remaining pre-culture, stocks were prepared by the addition of glycerol to a final concentration of 15% and stored at −80° C.

Example 7

Screening of *Trichoderma reesei* Cel6A Gene Libraries for Family 6 Cellulase Variant with Tolerance to Glucose This example describes the screening of *Trichoderma reesei* Cel6A-S413P variants with reduced inhibition by glucose by comparison to the parent TrCel6A-S413P that had been cloned into *Saccharomyces cerevisiae*.

TrCel6-S413P variants from yeast microcultures as described in Example 6 were tested in a 0.25 mL citrate buffered (pH 5) cellulose hydrolysis assay using a 96-well microplate format. An aliquot of supernatant from each variant was added to a first well containing 30 g/L glucose and to a second well absent of glucose and incubated with cellulose, at a concentration 0.067% w/v, for 19 hours at 50° C. Yeast supernatants were complemented with *Trichoderma reesei* Cel7B and Cel5A (40 mg protein/g cellulose) and 125 IU/g cellulose *A. niger* beta-glucosidase. Contained in each 96-well microplate were six parent TrCel6A-S413P controls used for comparison. Cellulase activity was measured by turbidometry. A ±glucose activity ratio was calculated for all TrCel6A variants and the parental TrCel6A-S413P by dividing the cellulase activity in the presence of glucose by the cellulase activity in the absence of glucose. The ±glucose activity ratio for each TrCel6A-S413P variant was compared to the average of six parental TrCel6A-S413P controls on a particular microplate and positives were selected at the 95% confidence level using a t-test. All positive variants were produced again in microculture and re-screened to reduce the number of false positives. Table 4 summarizes the screening results obtained for the EP-PCR library (Example 3) and the seven SSM libraries (Example 4).

TABLE 4

Screening Results of EP-PCR and SSM Libraries

| Library | # of Variants Screened | # of Positives |
|---|---|---|
| EP-PCR | 4800 | 43 |
| SSM-M134 | 100 | 11 |
| SSM-L136 | 40 | 2 |
| SSM-L215 | 68 | 0 |
| SSM-Y103 | 110 | 16 |
| SSM-S186 | 83 | 5 |
| SSM-G365 | 104 | 8 |
| SSM-R410 | 142 | 7 |

Example 8

Expression and Concentration of TrCel6A-S413P and its Variants from Large Scale Cultures Two 500 mL volumes of sterile SC*-Ura media (0.77 g/L-Ura drop out supplement, 1.7 g/L yeast nitrogen base, 5 g/L $(NH_4)_2SO_4$, 20 g/L casamino acids, 20 g/L glucose) were inoculated with 10 mL of overnight cultures of transformed *Saccharomyces cerevisiae* grown from cells freshly picked from an agar plate. The cultures were then incubated for 96 hours at 30° C. with shaking at 200 rpm.

After incubation, each pair of 500 mL yeast cultures was pooled, centrifuged for 10 minutes at 9000 rpm and the pellet (containing yeast cells) discarded. The supernatant pH was adjusted to 5.0 and then allowed to cool to 4° C. for an hour.

Subsequent to cooling, 625 g (NH$_4$)$_2$SO$_4$ was added to bring the yeast supernatant to 93% saturation. Precipitation was allowed to occur over a period of 16 hours at 4° C. with constant stirring. The next day the precipitate was centrifuged for 15 minutes at 9000 rpm and the supernatant discarded.

The pellet was resuspended with pipetting in a total volume of 10 mL of 50 mM sodium phosphate, pH 7.0. Once the pellet was resuspended, the solution was mixed with gentle inversion for 30 minutes. The solution was then centrifuged at 3000 rpm for 3 minutes to pellet any insoluble material. The supernatant was removed carefully with a pipette to prevent disruption of the pellet and retained. The concentration of TrCel6A-S413P in this supernatant was determined by ELISA using TrCel6A-specific antibodies with a standard curve of purified TrCel6A-S413P as described in Example 15, below. Purity of the samples was verified by SDS-PAGE analysis such as that shown for TrCel6A-S413P in FIG. 16.

Example 9

Enzymatic Characterization of Family 6 Cellulase Variants

Acid swollen cellulose (ASC) was produced from Sigmacell50 using procedures known to those skilled in the art. The ASC was slurried in 150 mM citrate, pH 5.0, to a final concentration of 1.8 g cellulose/L and degassed under vacuum for 5 minutes with constant stirring.

Figure 4:
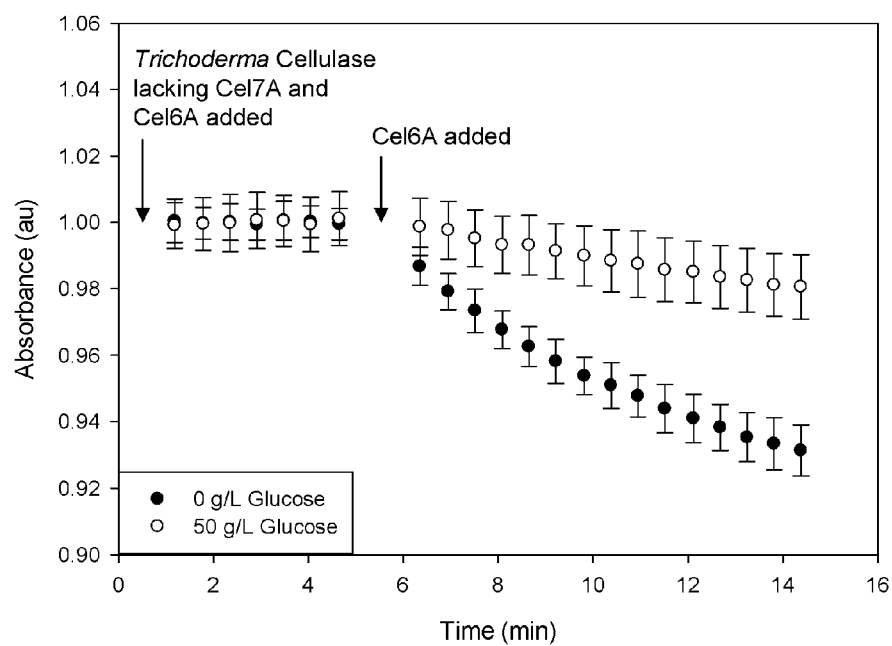
FIG. 4 depicts data demonstrating the activity of TrCel6A-S413P on Sigmacell50 which has been treated with a cellulase free of Cel7A and Cel6A. The cellobiohydrolase-free cellulase is added at the start of data acquisition and there is no discernable effect on apparent absorbance. Five minutes after the start of data collection, TrCel6A-S413P is added and the apparent absorbance begins to decrease. The activity of the Cel6A is proportionate to the slope of the linear portion of the decrease in absorbance. Activity in the absence of glucose and in the presence of the highest concentration of glucose used, 50 g/L, is shown. Data represent averages of 5 replicates and error bars represent one standard deviation.

Activity of the TrCel6A-S413P was monitored as a decrease in the absorbance of the slurry, diluted to 0.6 g cellulose/L either by water or a glucose solution, at 600 nm after the addition of cellulase. The sample was maintained at 50° C. and was stirred constantly during data collection. A twin-beam absorbance apparatus was used to subtract the absorbance of a no-enzyme control slurry in real time for each sample. Immediately after initiation of data acquisition, 50 mg/g cellulose of *Trichoderma* cellulase lacking Cel7A and Cel6A was added to all cuvettes. In the absence of cellobiohydrolases there is no significant change in the size of substrate particles and therefore no difference in the apparent absorbance due to an approximately constant size of the scatterers. During this time, the cellobiohydrolase-free enzyme mixture creates new chain ends, which are sites of enzymatic action by cellobiohydrolases. Five minutes after starting data acquisition, a parental Family 6 cellulase or a Family 6 cellulase variants added to a total dose of 50 mg/g. Cellobiohydrolases, such as a parental Family 6 cellulase or a Family 6 cellulase variant, effect a decrease in the size of the substrate particles via hydrolysis and the initial slope of the absorbance decrease was recorded as a measure of activity. As only the linear portion of the activity trace is used and only cellobiohydrolases, such as a parental Family 6 cellulase or a Family 6 cellulase variant, can reduce the apparent absorbance of the substrate, the assay is specific for the activity of the Cel6A alone and is not influenced by any potential inhibition of the non-cellobiohydrolase enzymes. Moreover, any influence of these enzymes would be the same when comparing a parental Family 6 cellulase to a Family 6 cellulase variant with decreased inhibition by glucose. Data collected during a typical experiment with TrCel6A-S413P are depicted in FIG. 4.

Activity data were collected in the absence of glucose and the presence of 10, 20, 30, 40 and 50 g/L glucose. Five replicate data sets were collected for each of these conditions. Data were plotted as absorbance slope vs. glucose concentration and fit with a model of simple linear inhibition using the Solver function in Microsoft Excel. The best fit values of $K_G$ and 95% confidence intervals were calculated using standard statistical methods. The mean value of the slope measured in the absence of glucose was taken as a measure of specific activity. A type 2, two-tailed t-test was used to compare the $K_G$ and specific activity of each TrCel6A-S413P variant tested to the parameter values of the parent enzyme.

As shown by the results in Table 5, below, and in FIGS. 5-15, all of the TrCel6A-S413P variants show at least 1.8-fold and as much as 6.73-fold reductions in glucose inhibition over the parental TrCel6A.

TABLE 5

Glucose inhibition constants for Family 6 cellulase variants derived from TrCel6A-S413P

| Amino Acid Substitution | $K_G$ (g/L) | 95% Confidence Intervals | Relative $K_G$ | P Value |
|---|---|---|---|---|
| None (TrCel6A-S413P) | 9.2 | 7.7-11.0 | 1.00 | 1.00 |
| Y103A | 25.1 | 21.2-30.2 | 2.73 | 1.5E−08 |
| Y103H | 21.0 | 18.2-24.6 | 2.28 | 2.2E−07 |
| Y103K | 39.1 | 35.3-45.2 | 4.26 | 3.2E−11 |
| Y103L | 32.0 | 28.1-36.9 | 3.48 | 2.6E−10 |
| Y103M | 26.0 | 18.8-36.4 | 2.83 | 1.4E−07 |
| Y103P | 26.8 | 22.9-32.2 | 2.91 | 4.4E−09 |
| Y103R | 24.2 | 19.8-29.9 | 2.63 | 4.2E−08 |
| Y103V | 26.2 | 21.1-32.8 | 2.85 | 1.5E−08 |
| M134I | 31.7 | 23.0-44.3 | 3.45 | 1.7E−04 |
| M134Q | 23.7 | 20.6-27.7 | 2.58 | 2.3E−08 |
| M134T | 31.2 | 25.1-39.4 | 3.39 | 1.1E−08 |
| M134V | 24.6 | 20.9-29.4 | 2.67 | 2.0E−08 |
| M134Y | 23.4 | 18.1-30.1 | 2.54 | 1.1E−03 |
| L136I | 39.5 | 35.5-44.7 | 4.29 | 2.8E−11 |
| L136V | 24.9 | 21.7-28.5 | 2.71 | 8.9E−09 |
| S186K | 19.9 | 14.2-27.5 | 2.16 | 2.6E−05 |
| S186Y | 23.8 | 17.5-33.3 | 2.59 | 2.2E−03 |
| G365D | 17.6 | 12.4-24.7 | 1.91 | 3.5E−04 |
| G365E | 21.1 | 16.8-27.3 | 2.29 | 3.8E−03 |
| G365Q | 38.7 | 33.1-46.2 | 4.20 | 4.1E−11 |
| G365S | 29.8 | 23.2-38.6 | 3.23 | 3.7E−09 |
| R410A | 25.0 | 17.0-37.4 | 2.72 | 1.0E−06 |
| R410F | 37.0 | 26.9-51.7 | 4.02 | 5.1E−10 |
| R410L | 49.5 | 27.0-97.9 | 5.38 | 8.1E−10 |
| R410Q | 37.8 | 28.6-51.2 | 4.11 | 2.0E−10 |
| R410S | 24.5 | 15.8-38.0 | 2.66 | 4.1E−06 |
| M134V-L136I | 48.6 | 42.3-57.0 | 5.28 | 5.8E−12 |
| L136I-L215I | 37.5 | 32.7-43.6 | 4.08 | 4.7E−11 |
| M134V-L136I-L215I | 61.9 | 50.9-76.3 | 6.73 | 1.1E−12 |

Example 10

Generation of HiCel6A and PcCel6A and Their Cloning into the Yep352/PGK91-1-α$_{ss}$-6His Vector Construction of the YEp352/PGK91-1-α$_{ss}$-6His Vector A DNA adapter containing SpeI, NheI, KpnI, and EcoRI restriction sites was prepared by annealing primers AT044 and AT045 together. The adapter contains sequences coding for six histidine residues downstream of the SpeI site and upstream of the NheI site. The adapter was inserted into a YEp based-plasmid (YEp352/PGK91-1α$_{ss}$) containing the pgk1 promoter, alpha mating factor secretion signal, and pgk1 terminator sequences to make plasmid YEp352/PGK91-1/α$_{ss}$6HNKE. Specifically, the linker was inserted as a NheI/EcoRI fragment into the NheI and EcoRI sites located downstream of the alpha mating factor secretion signal and upstream of the pgk1 terminator. Primer sequences are shown below:

AT044:
(SEQ ID NO: 106)
5'CTA GTC ATC ACC ATC ACC ATC ACG CTA GCT GAT CAC
TGA GGT ACC G

AT045:
(SEQ ID NO: 107)
5'AAT TCG GTA CCT CAG TGA TCA GCT AGC GTG ATG GTG
ATG GTG ATG A

Generation of YEp352/PGK91-1-$\alpha_{ss}$-6H-HiCel6A

Lyophilized *H. insolens* was resuspended in 300 μL sterile H$_2$O and 50 μL was spreaded onto Emerson YPSS pH 7 agar plate (0.4% Yeast extract, 0.1% K$_2$HPO$_4$, 0.05% MgSO$_4$.7H$_2$O, 1.5% Glucose, 1.5% Agar). Fungus was incubated for 6 days at 45° C. then spores were inoculated in Novo media (as per Barbesgaard U.S. Pat. No. 4,435,307): Incubation for 48 hours at 37° C. in 100 mL growth phase media (2.4% CSL, 2.4% Glucose, 0.5% Soy oil, pH adjusted to 5.5, 0.5% CaCO3), then 6 mL of pre-culture was transferred into 100 mL production phase media (0.25% NH$_4$NO$_3$, 0.56% KH$_2$PO$_4$, 0.44% K$_2$HPO$_4$, 0.075% MgSO$_4$.7H$_2$O, 2% Sigmacell, pH adjusted to 7, 0.25% CaCO$_3$) and culture was incubated for up to 4 days prior to biomass harvest. Then, 50 mg of biomass was used to isolate total RNA with the Absolutely RNA® Miniprep Kit (Stratagene) according to the manufacturer procedure. Total cDNA was generated from the total RNA using the SuperScript™II Reverse Transcriptase (Invitrogen) according to the manufacturer procedure. Gene encoding for HiCel6A was amplified from the cDNA using the following primers:

5'HiCel6A-cDNA
(SEQ ID NO: 108)
5'CTA TTG CTA GCT GTG CCC CGA CTT GGG GCC AGT GC

3'HiCel6A-cDNA
(SEQ ID NO: 109)
5'CTA TTG AAT TCG GTA CCT CAG AAC GGC GGA TTG GCA
TTA CGA AG

The PCR amplicon was cloned into the pGEM®-T Easy vector by TA-cloning according to the manufacturer's recommendations. Plasmid pGEM-HiCel6A was digested with NheI and EcoRI to release the HiCel6A gene. This fragment was purified and ligated into the NheI and EcoRI sites of YEp352/PGK91-1/$\alpha_{ss}$6HNKE to obtain YEp352/PGK91-1/$\alpha_{ss}$6H-HiCel6A.

Generation of YEp352/PGK91-1-$\alpha_{ss}$-6H-PcCel6A

Lyophilized *P. chrysosporium* was resuspended in 300 μL sterile H$_2$O and 50 μL were spreaded onto PDA plates. Plates were incubated at 24° C. for 4 days. Spores for *P. chrysosporium* were inoculated on a cellophane circle on top of a PDA plate and biomass was harvested after 4-6 days at 24° C. Then, 50 mg of biomass was used to isolate total RNA with the Absolutely RNA® Miniprep Kit (Stratagene) according to the manufacturer procedure. Total cDNA was generated from the total RNA using the SuperScript™II Reverse Transcriptase (Invitrogen) according to the manufacturer procedure. Gene encoding for PcCel6A was amplified from the cDNA using the following primers (which introduced an N-terminal NheI site and C-terminal KpnI and EcoRI sites):

5'PcCel6A-cDNA
(SEQ ID NO: 110)
5'CTA TTG CTA GCT CGG AGT GGG GAC AGT GCG GTG GC

3'PcCel6A-cDNA
(SEQ ID NO: 111)
5'CTA TTG AAT TCG GTA CCC TAC AGC GGC GGG TTG GCA
GCA GAA AC

The PCR amplicon was cloned into the pGEM®-T Easy vector by TA-cloning according to the manufacturer's recommendations. Plasmid pGEM-PcCel6A was digested with NheI and EcoRI to release the PcCel6A gene. This fragment was purified and ligated into the NheI and EcoRI sites of YEp352/PGK91-1/$\alpha_{ss}$6HNKE to obtain YEp352/PGK91-1/$\alpha_{ss}$6H-PcCel6A.

Example 11

Mutagenesis of Vectors with PcCel6A-His6 and HiCel6A-His6 and Their Variants

The HiCel6A and PcCel6A variants were constructed using a two-step PCR method involving megaprimer synthesis followed by PCR-mediated overlap extension (Vallejo et al., 1994). All PCR reactions were carried out using the High Fidelity iProof Taq Polymerase (BioRad). The plasmids YEp352/PGK91-1-$\alpha_{ss}$-6H-HiCel6A and YEp352/PGK91-1-$\alpha_{ss}$-6H-PcCel6A served as the templates for both *Humicola insolens* and *Phanerochaete chrysosporium*, respectively. Megaprimers upstream of (and including) the mutagenesis site were amplified using external primer YaN21 in combination with an internal reverse primer (i.e. DK022 for HiCel6A Y107L; refer to Table 6) specific to a given glucose tolerant variant. Similarly, megaprimers downstream of (and including) the mutagenesis site were amplified using the external primer PGKterm together with an internal forward primer (i.e. DK021 for HiCel6A Y107L; refer to Table 6) unique for a particular glucose tolerant variant. The internal primers were designed to introduce the desired glucose tolerant mutations into the Cel6A homologues. The megaprimers were purified using the Wizard® SV Gel and PCR Clean-Up System (Promega).

TABLE 6

List of primers used to introduce glucose tolerant mutations within the *H. insolens* and *P. chrysosporium* Cel6A homologues.

| Primer name | Homolog | Variant | SEQ ID NO: | Sequence |
|---|---|---|---|---|
| DK021 | HiCel6A | Y107L | 112 | CTCTGGGCCAACAAC<u>CTG</u>TACCGCTCTGAGGTC |
| DK022 | HiCel6A | Y107L | 113 | GACCTCAGAGCGGTA<u>CAG</u>GTTGTTGGCCCAGAG |
| DK023 | HiCel6A | Y107K | 114 | CTCTGGGCCAACAAC<u>AAG</u>TACCGCTCTGAGGTC |

TABLE 6-continued

List of primers used to introduce glucose tolerant mutations within the *H. insolens* and *P. chrysosporium* Ce16A homologues.

| Primer name | Homolog | Variant | SEQ ID NO: | Sequence |
|---|---|---|---|---|
| DK024 | HiCe16A | Y107K | 115 | GACCTCAGAGCGGTACTTGTTGTTGGCCCAGAG |
| DK025 | HiCe16A | Q139I | 116 | GAGGTCCCGAGCTTCATCTGGCTCGACCGCAAC |
| DK026 | HiCe16A | Q139I | 117 | GTTGCGGTCGAGCCAGATGAAGCTCGGGACCTC |
| DK027 | HiCe16A | Q139T | 118 | GAGGTCCCGAGCTTCACCTGGCTCGACCGCAAC |
| DK028 | HiCe16A | Q139T | 119 | GTTGCGGTCGAGCCAGGTGAAGCTCGGGACCTC |
| DK029 | HiCe16A | L141I | 120 | CCGAGCTTCCAGTGGATCGACCGCAACGTCACG |
| DK030 | HiCe16A | L141I | 121 | CGTGACGTTGCGGTCGATCCACTGGAAGCTCGG |
| DK031 | HiCe16A | L141V | 122 | CCGAGCTTCCAGTGGGTCGACCGCAACGTCACG |
| DK032 | HiCe16A | L141V | 123 | CGTGACGTTGCGGTCGACCCACTGGAAGCTCGG |
| DK033 | HiCe16A | A194Y | 124 | TCGAACGGCGAGTGGTACATCGCCAACAACGGC |
| DK034 | HiCe16A | A194Y | 125 | GCCGTTGTTGGCGATGTACCACTCGCCGTTCGA |
| DK035 | HiCe16A | A194K | 126 | TCGAACGGCGAGTGGAAGATCGCCAACAACGGC |
| DK036 | HiCe16A | A194K | 127 | GCCGTTGTTGGCGATCTTCCACTCGCCGTTCGA |
| DK037 | HiCe16A | G372Q | 128 | GGCCAGAAGGAATGGCAGCACTGGTGCAATGCC |
| DK038 | HiCe16A | G372Q | 129 | GGCATTGCACCAGTGCTGCCATTCCTTCTGGCC |
| DK039 | HiCe16A | R417Q | 130 | GACACGACCGCTGCCCAGTACGACTACCACTGC |
| DK040 | HiCe16A | R417Q | 131 | GCAGTGGTAGTCGTACTGGGCAGCGGTCGTGTC |
| DK041 | HiCe16A | R417F | 132 | GACACGACCGCTGCCTTCTACGACTACCACTGC |
| DK042 | HiCe16A | R417F | 133 | GCAGTGGTAGTCGTAGAAGGCAGCGGTCGTGTC |
| DK043 | PcCe16A | Y98L | 134 | GATCTTCCTCAGCCCTCTGTACGCGAACGAGGTC |
| DK044 | PcCe16A | Y98L | 135 | GACCTCGTTCGCGTACAGAGGGCTGAGGAAGATC |
| DK045 | PcCe16A | Y98K | 136 | GATCTTCCTCAGCCCTAAGTACGCGAACGAGGTC |
| DK046 | PcCe16A | Y98K | 137 | GACCTCGTTCGCGTACTTAGGGCTGAGGAAGATC |
| DK047 | PcCe16A | T129I | 138 | GCAAATATCCCCACTTTCATCTGGCTGGACTCTGTC |
| DK048 | PcCe16A | T129I | 139 | GACAGAGTCCAGCCAGATGAAAGTGGGGATATTTGC |
| DK049 | PcCe16A | T129Q | 140 | GCAAATATCCCCACTTTCCAGTGGCTGGACTCTGTC |
| DK050 | PcCe16A | T129Q | 141 | GACAGAGTCCAGCCACTGGAAAGTGGGGATATTTGC |
| DK051 | PcCe16A | L131I | 142 | CCCACTTTCACGTGGATCGACTCTGTCGCGAAG |
| DK052 | PcCe16A | L131I | 143 | CTTCGCGACAGAGTCGATCCACGTGAAAGTGGG |
| DK053 | PcCe16A | L131V | 144 | CCCACTTTCACGTGGGTCGACTCTGTCGCGAAG |
| DK054 | PcCe16A | L131V | 145 | CTTCGCGACAGAGTCGACCCACGTGAAAGTGGG |
| DK055 | PcCe16A | S182Y | 146 | TCCAACGGAGAGTTCTACATTGCCAACAACGGA |
| DK056 | PcCe16A | S182Y | 147 | TCCGTTGTTGGCAATGTAGAACTCTCCGTTGGA |
| DK057 | PcCe16A | S182K | 148 | TCCAACGGAGAGTTCAAGATTGCCAACAACGGA |
| DK058 | PcCe16A | S182K | 149 | TCCGTTGTTGGCAATCTTGAACTCTCCGTTGGA |
| DK059 | PcCe16A | G359Q | 150 | CATCCGCCAACAGTGGCAGGACTGGTGCAACATC |
| DK060 | PcCe16A | G359Q | 151 | GATGTTGCACCAGTCCTGCCACTGTTGGCGGATG |

TABLE 6-continued

List of primers used to introduce glucose tolerant mutations within the *H. insolens* and *P. chrysosporium* Cel6A homologues.

| Primer name | Homolog | Variant | SEQ ID NO: | Sequence |
|---|---|---|---|---|
| DK061 | PcCel6A | R404Q | 152 | CCAACAGCTCCTCGCCC*CAG*TACGACTCGACTTGTTC |
| DK062 | PcCel6A | R404Q | 153 | GAACAAGTCGAGTCGTA*CTG*GGGCGAGGAGCTGTTGG |
| DK063 | PcCel6A | R404F | 154 | CCAACAGCTCCTCGCCC*TTC*TACGACTCGACTTGTTC |
| DK064 | PcCel6A | R404F | 155 | GAACAAGTCGAGTCGTA*GAA*GGGCGAGGAGCTGTTGG |
| YαLN21 | PGK plasmid | — | 95 | AGCACAAATAACGGGTTATTG |
| PGKterm | PGK plasmid | — | 96 | GCAACACCTGGCAATTCCTTACC |

Amino acids are italicized in cases where the original residue differs from that found in the homologous T. reesei sequence. With respect to the primer sequences, underlined nucleotides effect the desired amino acid substitution. External plasmid primers are included.

During the second round of PCR, both megaprimers of a desired construct were allowed to anneal and extend for 10 cycles to generate the final template. The external primers YαN21 and PGKterm were then added for another 25 cycles to amplify the final product, which was subsequently purified using the Wizard® SV Gel and PCR Clean-Up System. Both the purified PCR product and the linearized vector YEp352/PGK91-1α$_{ss}$-6HNKE (digested with NheI+KpnI) were transformed and cloned via in vivo recombination within the BY4742 yeast strain using the procedure described by Gietz and Woods (2002). For each construct, the vector was isolated from the transformed yeast using a method modified from Hoffman and Winston (Hoffman and Winston, 1987) and transformed in *E. coli* DH5α chemically-competent cells. Plasmids were isolated from the *E. coli* cells using the Wizard® Plus SV Minipreps DNA Purification System (Promega). The integrity of the cloned region of all the variants was confirmed by DNA sequence analysis.

Example 12

Expression and Concentration of PcCel6A-His6 and HiCel6A-His6 and Their Variants from Large Scale Cultures Two 500 mL volumes of sterile SC*-Ura media (0.77 g/L-Ura drop out supplement, 1.7 g/L yeast nitrogen base, 5 g/L $(NH_4)_2SO_4$, 20 g/L casamino acids, 20 g/L glucose) were inoculated with 10 mL of overnight cultures of transformed *Saccharomyces cerevisiae* grown from cells freshly picked from an agar plate. The cultures were then incubated for 96 hours at 30° C. with shaking at 200 rpm.

After incubation, each pair of 500 mL yeast cultures was pooled, centrifuged for 10 minutes at 9000 rpm and the pellet (containing yeast cells) discarded. The supernatant pH was adjusted to 5.0 and then allowed to cool to 4° C. for an hour. BSA (0.1 g) was added to help co-precipitate Cel6A. Subsequent to cooling, 559 g $(NH_4)_2SO_4$ was added to bring the yeast supernatant to 85% saturation. Precipitation was allowed to occur over a period of 16 hours at 4° C. with constant stirring. The next day the precipitate was centrifuged for 15 minutes at 9000 rpm and the supernatant discarded.

The pellet was resuspended with pipetting in a total volume of 50 mL binding buffer (200 mM NaCl, 20 mM sodium phosphate, 30 mM imidazole, pH 7.4). Once the pellet was resuspended, the solution was mixed with gentle inversion for 30 minutes at 4° C. The solution was then filtered with glass fiber filter paper to remove insoluble material before purification as described in Example 13.

Example 13

Purification of PcCel6A-His6 and HiCel6A-His6 and Their Variants

For activity assays (Example 14), the His-tagged parental *Humicola* Cel6A and *Phanerochaete* Cel6A cellulases and their respective variants were purified from culture supernatants using immobilized metal affinity chromatography. Prior to loading proteins onto the His-trap column, the $Ni^{2+}$ resin was equilibrated with binding buffer (200 mM NaCl, 20 mM sodium phosphate, 30 mM imidazole, pH 7.4). The culture supernatant was adjusted to the same salt concentrations and pH as the binding buffer and applied to a 1 mL His-trap column (GE HealthcareO at a flow rate of 0.5-1.0 mL/min. The column was then washed with the same binding buffer until $OD_{280nm}$ reached a steady baseline. The bound His-tagged Cel6A was eluted from the column with elution buffer (20 mM sodium phosphate, 500 mM imidazole, pH 7.4).

Figure 16:
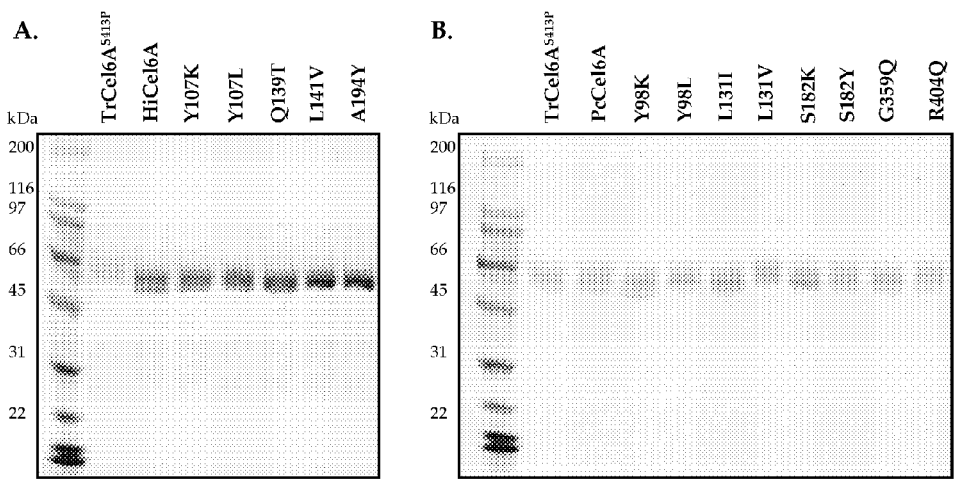
FIG. 16 shows SDS-PAGE analysis of parental Family 6 cellulases and Family 6 cellulase variants purified as described in Example 8 (TrCel6A-S413P) and Example 13 (HiCel6A variants, panel A) and PcCel6A variants (panel B). The purified Family 6 cellulases were visualized by Coomassie blue staining.

The elution buffer was removed from the purified proteins by buffer exchange and 5 mL of the eluted fractions was added to 15 mL of 50 mM citrate pH 5.0 buffer and loaded onto a Centricon Plus-20 (polyethersulfone membrane, nominal molecular weight cut-off of 5 kDa). The column was centrifuged at 1600×g for 10 minutes or until the volume remaining in the column was 2.5 mL. At this point, 17.5 mL of 50 mM citrate buffer pH 5.0 was further added to the column and the centrifugation repeated. The last centrifugation was done in the same fashion until only 1-2 mL remained in the column. The protein concentration of this final supernatent determined using a Biorad protein assay using a *Trichoderma reesei* cellulase of known protein concentration. Purity of the parental and variant PcCel6A and HiCel6A was confirmed by SDS-PAGE analysis (FIG. 16).

Example 14

Enzymatic Characterization of PcCel6A-His6 and HiCel6A-His6 and Their Variants Activity assays were performed as described in Example 9 using the parental PcCel6A-His6 and HiCel6A-His6 cellulases and variants derived therefrom that were purified from yeast culture filtrates as described in Example 13, above. As shown by the results in Table 7, below, all of the HiCel6A and PcCel6A variants show at least 1.43-fold and as much as 3.22-fold less inhibition by glucose over the corresponding parental Family 6 cellulase control.

TABLE 7

Glucose inhibition constants for parental PcCel6A and HiCel6A cellulases and Family 6 cellulase variants derived from PcCel6A and HiCel6A.

| Amino Acid Substitution | Equivalent TrCel6A position | $K_G$ (g/L) | 95% Confidence Intervals | Relative $K_G$ | P Value vs. wildtype |
|---|---|---|---|---|---|
| *P. chrysosporium* wildtype | — | 20.3 | 16.7-24.9 | 1.00 | 1.00 |
| Y98K | 103 | 65.5 | 52.9-82.7 | 3.22 | 2.1E−08 |
| Y98L | 103 | 31.9 | 26.1-39.1 | 1.57 | 2.8E−03 |
| L131I | 136 | 32.9 | 28.7-38.0 | 1.62 | 7.1E−04 |
| L131V | 136 | 33.3 | 26.3-42.4 | 1.64 | 2.1E−03 |
| S182K | 186 | 39.7 | 32.3-49.5 | 1.95 | 5.5E−05 |
| S182Y | 186 | 46.4 | 36.0-60.6 | 2.28 | 7.4E−06 |
| G359Q | 365 | 35.2 | 27.0-46.2 | 1.73 | 1.3E−03 |
| R404Q | 410 | 47.4 | 31.6-74.4 | 2.33 | 7.6E−05 |
| *H. insolens* wildtype | — | 31.9 | 26.4-38.8 | 1.00 | 1.00 |
| Y107K | 103 | 45.5 | 35.3-59.9 | 1.43 | 2.6E−02 |
| Y107L | 103 | 61.0 | 46.3-82.3 | 1.91 | 2.1E−04 |
| Q139T | 134 | 51.9 | 40.6-67.8 | 1.62 | 2.6E−03 |
| L141V | 136 | 54.6 | 41.7-73.8 | 1.71 | 1.5E−03 |
| A194Y | 186 | 63.2 | 50.2-81.7 | 1.98 | 5.2E−05 |

Example 15

Determination of TrCel6A-S413P Concentration by ELISA

Supernatants and purified standard were diluted in phosphate-buffered saline (PBS), pH 7.2, and incubated overnight at 4° C. in microtitre plates (Costar EIA #9018). Following overnight incubation, these plates were washed with PBS containing 0.1% Tween-20 (PBS/Tween) and then incubated in PBS containing 1% bovine serum albumin (PBS/BSA) for 1 hr at room temperature. Blocked microtitre wells were washed with PBS/Tween. Rabbit polyclonal antisera specific for TrCel6A was diluted in PBS/BSA, added to the microtitre plates and incubated for 2 hr at room temperature. Plates were washed and incubated with a goat anti-rabbit antibody coupled to horseradish peroxidase (Sigma #A6154), diluted 1/2000 in PBS/BSA, for 1 hr at room temperature. After washing, 100 µL of tetramethylbenzidine (Sigma #8665) was added to well and incubated for 30 min at room temperature. The absorbance at 360 nm was measured in each well and converted into protein concentration using the TrCel6A standard curve.

PBS contains:

| Component | g/L |
|---|---|
| NaCl | 80 |
| KCl | 2 |
| $Na_2HPO_4$ | 14.4 |
| $KH_2PO_4$ | 2.4 |

REFERENCES

Barr, B., Hsieh, Y., Ganem, B., and Wilson, D. (1996) Identification of two functionally different classes of exocellulases. *Biochemistry* 35:586.

Butler, T. and Alcalde, M. (2003) In Methods in Molecular Biology, vol. 231: (F. H. Arnold and G. Georgiou, editors), Humana Press Inc. Totowa (N.J.), pages 17-22.

Caminal, G., Lopez-Santin, J., and Sola, C. (1985) Kinetic modeling of the enzymatic hydrolysis of pretreated cellulose. *Biotech. Bioeng.* 27:1282.

Claeyssens, M. and Henrissat, B. 1992, Protein Science 1: 1293-1297.

Converse, A., Matsuno, R., Tanaka, M., and Taniguchi, M. (1988) A model of enzyme adsorption and hydrolysis of microcrystalline cellulose with slow deactivation of the adsorbed enzyme. *Biotech. Bioeng.* 32:45.

Eriksson, T., Karlsson, J., and Tjerneld, F. (2002) A model explaining the declining rate in hydrolysis of lignocellulose substrates with cellobiohydrolase I (Cel7A) and endoglucanase I (Cel7B) of *Trichoderma reesei*. *Appl. Biochem. Biotechnol.* 101:41.

Farrell, A., Plevin, R., Turner, B., Jones, A., O'Hare, M., and Kammen, D. (2006) Ethanol can contribute to energy and environmental goals. *Science* 311:506.

Gietz, R. D. and Woods, R. A. (2002) Transformation of yeast by the Liac/ss carrier DNA/PEG method. *In Methods in Enzymology*, 350:87-96.

Gruno, M., Valjamae, P., Pettersson, G., and Johansson, G. (2004) Inhibition of the *Trichoderma reesei* cellulases by cellobiose is strongly dependent on the nature of the substrate. *Biotech. Bioeng.* 86:503.

Gusakov, A., and Sinitsyn, A. (1992) A theoretical analysis of cellulase product inhibition: Effect of cellulase binding constant, enzyme/substrate ratio, and β-glucosidase activity on the inhibition pattern. *Biotech. Bioeng.* 40:663.

Holtzapple, M., Cognata, M., Shu, Y., and Hendrickson, C. (1990) Inhibition of *Trichoderma reesei* cellulase by sugars and solvents. *Biotech. Bioeng.* 36:275.

Hoffman, C. S., and Winston, F. (1987) A ten-minute DNA preparation from yeast efficiently releases autonomous plasmids for transformation of *Escherichia coli. Gene,* 57: 267-272.

Lee, Y-H. and Fan, L. T. (1983) Kinetic studies of enzymatic hydrolysis of insoluble cellulose: (II) Analysis of extended hydrolysis times. *Biotech. Bioeng.* 25:939.

Meinke, A., et al. 1995. J. Biol. Chem. 270:4383-4386.

Nidetzky, B. and Steiner, W. (1993) A new approach for modeling cellulase-cellulose adsorption and the kinetics of the enzymatic hydrolysis of microcrystalline cellulose. *Biotech. Bioeng.* 42:469.

Perlack, R., Wright, L., Tuhollow, A., and Graham, R. (2005) Biomass as feedstock for a bioenergy and bioproducts industry: The technical feasability of a billion-ton annual supply. Oak Ridge National Laboratory.

Steipe, B. (2004) Consensus-based engineering of protein stability: From intrabodies to thermostable enzymes. *Meth. Enz.* 388:176.

Teleman, A., Koivula, A., Reinikainen, T., Valkeajärvi, A., Teeri, T. T., Drakenberg, T., and Teleman, O. (1995) Progress-curve analysis shows that glucose inhibits the cellotriose hydrolysis catalysed by cellobiohydrolase II from *Trichoderma reesei. Eur. J. Biochem.* 231:250.

Tolan, J., (2002) Iogen's process for producing ethanol from cellulosic biomass, *Clean Tech. and Enviro. Policy,* 3:339.

Vallejo, A. N., Pogulis, R. J. and Pease, L. R. (1994) In vitro synthesis of novel genes: mutagenesis and recombination by PCR. *PCR Methods Appl.,* 4:123-130.

Zhang, S., Wolfgang, D., and Wilson, D. (1999) Substrate heterogeniety causes the nonlinear kinetics of insoluble cellulose hydrolysis. *Biotech. Bioeng.* 66:35.

Zhang, S., Irwin, D., and Wilson, D. (2000) Site-directed mutation of noncatalytic residues of *Thermobifida fusca* exocellulase Cel6B. *Eur. J. Biochem.* 267:3101.

The invention claimed is:

1. An isolated Family 6 cellulase variant comprising at least one of the amino acid substitutions selected from the group consisting of:
   - a basic, non-polar or proline residue at position 103 (X103H, K, R, A, V, L, P, or M);
   - a valine or isoleucine residue at position 136 (X136V, or I);
   - a tyrosine or lysine residues at position 186 (X186Y, or K);
   - an acidic, glutamine or serine residue at position 365 (X365D, E, Q, or S); and
   - an alanine, phenylalanine, leucine, glutamine or serine residue at position 410 (X410A, F, L, Q, or S), said position determined from alignment of a parental Family 6 cellulase with a *Trichoderma reesei* Cel6A amino acid sequence as defined in SEQ ID NO: 1 and wherein said isolated Family 6 cellulase variant comprises an amino acid sequence which is at least about 55% identical to amino acids 83-447 of SEQ ID NO: 1 and exhibits at least about 1.4-fold less inhibition by glucose than the parental Family 6 cellulase from which it is derived.

2. The isolated Family 6 cellulase variant of claim 1, wherein the amino acid sequence of said isolated Family 6 cellulase variant is at least about 63% identical to amino acids 83-447 of SEQ ID NO: 1.

3. The isolated Family 6 cellulase variant of claim 2, wherein the amino acid sequence of said isolated Family 6 cellulase variant is at least about 95% identical to amino acids 83-447 of SEQ ID NO: 1.

4. The isolated Family 6 cellulase variant of claim 1, wherein said residue at position 103 is a histidine, arginine or lysine residue.

5. The isolated Family 6 cellulase variant of claim 1, wherein said residue at position 103 is an alanine, valine, methionine or leucine residue.

6. The isolated Family 6 cellulase variant of claim 1, wherein said residue at position 365 is aspartic acid or glutamic acid.

7. The isolated Family 6 cellulase variant of claim 1, further comprising an isoleucine, valine, threonine, tyrosine or glutamine residue at position 134.

8. The isolated Family 6 cellulase variant of claim 1, further comprising an isoleucine residue at position 215.

9. The isolated Family 6 cellulase variant of claim 1, further comprising a proline residue at position 413.

10. The isolated Family 6 cellulase variant of claim 1, wherein said isolated Family 6 cellulase variant exhibits at least about 1.8-fold less inhibition by glucose than the parental Family 6 cellulase from which it is derived.

11. The isolated Family 6 cellulase variant of claim 1, wherein said parental Family 6 cellulase from which said isolated Family 6 cellulase variant is derived does not have any of a naturally-occurring basic, non-polar or proline residue at position 103, a naturally-occurring valine or isoleucine residue at position 136, a naturally-occurring tyrosine or lysine residues at position 186, a naturally-occurring acidic, glutamine or serine residue at position 365, or a naturally-occurring alanine, phenylalanine, leucine, glutamine or serine residue at position 410.

12. A process for producing the Family 6 cellulase variant of claim 1, comprising culturing an isolated genetically modified microbe comprising a genetic construct encoding said Family 6 cellulase variant;
   expressing and secreting the Family 6 cellulase variant; and
   recovering the Family 6 cellulase variant from the culture medium.

13. The process of claim 12, wherein said microbe is a yeast or a filamentous fungus.

14. The process of claim 13, wherein said microbe is *Saccharomyces, Pichia, Trichoderma, Hypocrea, Aspergillus, Fusarium, Humicola,* or *Neurospora*.

15. The process of claim 14, wherein said microbe is *Saccharomyces cerevisiae* or *Trichoderma reesei*.

16. A process for the hydrolyzing a cellulosic substrate to glucose, comprising treating the cellulosic substrate with a cellulase composition so as to effect the conversion of the cellulose to glucose, said cellulase composition comprising the Family 6 cellulase variant of claim 1.

17. The process of claim 16, wherein the cellulosic substrate is a pretreated lignocellulosic feedstock.

18. The process of claim 17, wherein the pretreated lignocellulosic feedstock comprises corn stover, wheat straw, barley straw, rice straw, oat straw, canola straw, soybean stover, corn fiber, sugar beet pulp, pulp mill fines and rejects, sugar cane bagasse, hardwood, softwood, sawdust, switch grass, miscanthus, cord grass, or reed canary grass.

19. An isolated Family 6 cellulase variant selected from the group consisting of
   TrCel6A-Y103A-S413P (SEQ ID NO: 37);
   TrCel6A-Y103H-S413P (SEQ ID NO: 38);
   TrCel6A-Y103K-S413P (SEQ ID NO: 39);
   TrCel6A-Y103L-S413P (SEQ ID NO: 40);
   TrCel6A-Y103M-S413P (SEQ ID NO: 41);
   TrCel6A-Y103P-S413P (SEQ ID NO: 42);
   TrCel6A-Y103R-S413P (SEQ ID NO: 43);
   TrCel6A-Y103V-S413P (SEQ ID NO: 44);
   TrCel6A-L136I -S413P (SEQ ID NO: 45);
   TrCel6A-L136V -S413P (SEQ ID NO: 46);
   TrCel6A-S186K -S413P (SEQ ID NO: 47);
   TrCel6A-S186Y -S413P (SEQ ID NO: 48);
   TrCel6A-G365D-S413P (SEQ ID NO: 49);
   TrCel6A-G365E-S413P (SEQ ID NO: 50);
   TrCel6A-G365Q-S413P (SEQ ID NO: 51);
   TrCel6A-G365S-S413P (SEQ ID NO: 52);
   TrCel6A-R410A-S413P (SEQ ID NO: 53);
   TrCel6A-R410E-S413P (SEQ ID NO: 54);
   TrCel6A-R410L-S413P (SEQ ID NO: 55);
   TrCel6A-R410Q-S413P (SEQ ID NO: 56);
   TrCel6A-R410S-S413P (SEQ ID NO: 57);

TrCel6A-M134V-L136I-S413P (SEQ ID NO: 62);
TrCel6A-L136I-L215I-S413P (SEQ ID NO: 63);
TrCel6A-M134V-L136I-L215I-S413P (SEQ ID NO: 71);
HiCel6A-Y107K (SEQ ID NO: 78);
HiCel6A-Y107L (SEQ ID NO: 79);
HiCel6A-Q139T (SEQ ID NO: 80);
HiCel6A-L141V (SEQ ID NO: 81);
HiCel6A-A194Y (SEQ ID NO: 82);
PcCel6A-Y98K (SEQ ID NO: 83);
PcCel6A-Y98L (SEQ ID NO: 84);
PcCel6A-L131I (SEQ ID NO: 85);
PcCel6A-L131V (SEQ ID NO: 86);
PcCel6A-S182K (SEQ ID NO: 87);
PcCel6A-S182Y (SEQ ID NO: 88);
PcCel6A-G359Q (SEQ ID NO: 89); and
PcCel6A-R404Q (SEQ ID NO: 90),
wherein said isolated Family 6 cellulase variant exhibits at least 1.4-fold less inhibition by glucose than a parental Family 6 cellulase from which it is derived.

* * * * *

UNITED STATES PATENT AND TRADEMARK OFFICE
CERTIFICATE OF CORRECTION

| | | |
|---|---|---|
| PATENT NO. | : 8,012,734 B2 | Page 1 of 2 |
| APPLICATION NO. | : 12/355373 | |
| DATED | : September 6, 2011 | |
| INVENTOR(S) | : James A. Lavigne et al. | |

It is certified that error appears in the above-identified patent and that said Letters Patent is hereby corrected as shown below:

ON THE TITLE PAGE ITEM [56] REFERENCES CITED:

Other Publications, "Lee et al.," should begin a new line.

COLUMN 3:

Line 63, "NO: 1" should read --NO: 1.--;
Line 66, "least" should read --at least--; and
Line 67, "NO: 1" should read --NO: 1.--.

COLUMN 5:

Line 29, "dues" should read --due--;
Line 43, "residues" should read --residue--;
Line 60, "residues" should read --residue--; and
Line 65, "cellulases" should be deleted.

COLUMN 8:

Line 46, "α-helices" should read --α-helices,--.

COLUMN 13:

Line 9, "tip, arg, leu, pyr4, pyr, ura3," should be italicized;
Line 10, "ura5, his, or ade" should be italicized; and
Line 56, "are" should read --is--.

COLUMN 14:

Line 46, "hydrolyzes" should read --hydrolyze--.

Signed and Sealed this
Twenty-ninth Day of November, 2011

David J. Kappos
*Director of the United States Patent and Trademark Office*

CERTIFICATE OF CORRECTION (continued)
U.S. Pat. No. 8,012,734 B2

COLUMN 16:

Line 9, "mean" should read --meant--.

COLUMN 17:

Line 44, "PCR were" should read --PCR procedures were--.

COLUMN 19:

Line 25, "amplified" should read --amplify--.

COLUMN 23:

Line 20, "CaCO3)," should read --CaCO$_3$),--.

COLUMN 28:

Line 52, "was" should read --were--.

COLUMN 261:

Line 19, "residues" should read --residue--.

COLUMN 262:

Line 12, "residues" should read --residue--;
  Line 32, "the" should be deleted; and
  Line 64, "TrCe16A-R410E-S413P (SEQ ID NO:54);" should read
     --TrCe16A-R410F-S413P (SEQ ID NO:54);--.

SEQUENCE LISTING

```
<160> NUMBER OF SEQ ID NOS: 161

<210> SEQ ID NO 1
<211> LENGTH: 447
<212> TYPE: PRT
<213> ORGANISM: Trichoderma reesei

<400> SEQUENCE: 1

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
```

```
                225                 230                 235                 240
Ala Tyr Leu Glu Cys Ile Asn Tyr Ala Val Thr Gln Leu Asn Leu Pro
                    245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                    325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 2
<211> LENGTH: 362
<212> TYPE: PRT
<213> ORGANISM: Hypocrea koningii

<400> SEQUENCE: 2

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
                20                  25                  30

Gly Ala Met Ala Thr Ala Ala Ala Val Ala Lys Val Pro Ser Phe
            35                  40                  45

Met Trp Leu Asp Thr Leu Asp Lys Thr Pro Leu Met Glu Gln Thr Leu
50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
    130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
```

```
                165                 170                 175
Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
            195                 200                 205

Arg Ala Leu Arg Gly Leu Ala Thr Asn Val Ala Asn Tyr Asn Gly Trp
            210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Arg Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
            275                 280                 285

Gly Phe Gly Ile Arg Pro Ser Ala Asn Thr Gly Asp Ser Leu Leu Asp
            290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
            355                 360

<210> SEQ ID NO 3
<211> LENGTH: 362
<212> TYPE: PRT
<213> ORGANISM: Trichoderma viride CICC 13038

<400> SEQUENCE: 3

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
                20                  25                  30

Gly Ala Met Ala Thr Ala Ala Ala Val Ala Lys Val Pro Ser Phe
            35                  40                  45

Met Trp Leu Asp Thr Leu Asp Lys Thr Pro Leu Met Glu Gln Thr Leu
        50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Pro Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
```

```
                    180                 185                 190
Pro Ala Ala Gln Leu Phe Ala Asn Val Tyr Lys Asn Ala Ser Ser Pro
                195                 200                 205

Arg Ala Leu Arg Gly Leu Ala Thr Asn Val Ala Asn Tyr Asn Gly Trp
            210                 215                 220

Asn Ile Thr Ser Pro Ser Tyr Thr Gln Gly Asn Ala Val Tyr Asn
225                 230                 235                 240

Glu Lys Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
    290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360

<210> SEQ ID NO 4
<211> LENGTH: 362
<212> TYPE: PRT
<213> ORGANISM: Hypocrea koningii 3.2774

<400> SEQUENCE: 4

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
                20                  25                  30

Gly Ala Met Ala Thr Ala Ala Ala Val Ala Lys Val Pro Ser Phe
            35                  40                  45

Met Trp Leu Asp Thr Phe Asp Lys Thr Pro Leu Met Glu Gln Thr Leu
    50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Asp Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
    130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
```

```
                195                 200                 205
Arg Ala Leu Arg Gly Leu Ala Thr Asn Val Ala Asn Tyr Asn Gly Trp
    210                 215                 220

Asn Ile Thr Ser Pro Ser Tyr Thr Gln Gly Asn Ala Val Tyr Asn
225                 230                 235                 240

Glu Gln Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
    290                 295                 300

Ser Phe Val Trp Ile Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360

<210> SEQ ID NO 5
<211> LENGTH: 362
<212> TYPE: PRT
<213> ORGANISM: Hypocrea koningii AS3.2774

<400> SEQUENCE: 5

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

Gly Ala Met Ala Thr Ala Ala Ala Val Ala Lys Val Pro Ser Ser
        35                  40                  45

Met Trp Leu Asp Thr Phe Asp Lys Thr Pro Leu Met Glu Gln Thr Leu
50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Asp Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
```

```
                    210                 215                 220
Asn Ile Thr Ser Pro Pro Ser Tyr Thr Gln Gly Asn Ala Val Tyr Asn
225                 230                 235                 240

Glu Gln Leu Tyr Ile His Ala Ile Gly Pro Leu Leu Ala Asn His Gly
                    245                 250                 255

Trp Ser Asn Ala Phe Phe Ile Thr Asp Gln Gly Arg Ser Gly Lys Gln
                    260                 265                 270

Pro Thr Gly Gln Gln Gln Trp Gly Asp Trp Cys Asn Val Ile Gly Thr
                    275                 280                 285

Gly Phe Gly Ile Arg Pro Ser Ala Asn Thr Gly Asp Ser Leu Leu Asp
                    290                 295                 300

Ser Phe Val Trp Ile Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                    325                 330                 335

Gln Pro Ala Pro Gln Ala Gly Ala Trp Phe Gln Ala Tyr Phe Val Gln
                    340                 345                 350

Leu Leu Thr Asn Ala Asn Pro Ser Phe Leu
                    355                 360

<210> SEQ ID NO 6
<211> LENGTH: 362
<212> TYPE: PRT
<213> ORGANISM: Trichoderma parceramosum

<400> SEQUENCE: 6

Ala Thr Tyr Ser Gly Asn Pro Phe Val Gly Val Thr Pro Trp Ala Asn
1                   5                   10                  15

Ala Tyr Tyr Ala Ser Glu Val Ser Leu Ala Ile Pro Ser Leu Thr
                    20                  25                  30

Gly Ala Met Ala Thr Ala Ala Ala Val Ala Lys Val Pro Ser Phe
                    35                  40                  45

Met Trp Leu Asp Thr Leu Asp Lys Thr Pro Leu Met Glu Gln Thr Leu
50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                    85                  90                  95

Asn Gly Glu Tyr Ser Ile Ala Asp Gly Gly Val Ala Lys Tyr Lys Asn
                    100                 105                 110

Tyr Ile Asp Thr Ile Arg Gln Ile Val Val Glu Tyr Ser Asp Ile Arg
                    115                 120                 125

Thr Ile Leu Val Ile Glu Pro Asp Ser Leu Ala Asn Leu Val Thr Asn
                    130                 135                 140

Leu Gly Thr Pro Lys Cys Ala Asn Ala Gln Ser Ala Tyr Leu Glu Cys
145                 150                 155                 160

Ile Asn Tyr Ala Ile Thr Gln Leu Asn Leu Pro Asn Ile Ala Met Tyr
                    165                 170                 175

Leu Asp Ala Gly His Ala Gly Trp Leu Gly Trp Pro Ala Asn Gln Asp
                    180                 185                 190

Pro Ala Ala Gln Leu Phe Ala Asn Val Tyr Lys Asn Ala Ser Ser Pro
                    195                 200                 205

Ser Ala Leu Arg Gly Leu Ala Thr Asn Val Ala Asn Tyr Asn Gly Trp
                    210                 215                 220

Asn Ile Thr Ser Pro Pro Ser Tyr Thr Gln Gly Asn Ala Val Tyr Asn
```

```
                225                 230                 235                 240
Glu Lys Leu Tyr Ile His Ala Ile Gly Pro Leu Leu Ala Asn His Gly
                    245                 250                 255

Trp Ser Asn Ala Phe Phe Ile Thr Asp Gln Gly Arg Ser Gly Lys Gln
                260                 265                 270

Pro Thr Gly Gln Gln Gln Trp Gly Asp Trp Cys Asn Val Ile Gly Thr
            275                 280                 285

Gly Phe Gly Ile Arg Pro Ser Ser Asn Thr Gly Asp Ser Leu Leu Asp
        290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
                340                 345                 350

Leu Leu Thr Asn Ala Asn Pro Ser Phe Leu
                355                 360

<210> SEQ ID NO 7
<211> LENGTH: 365
<212> TYPE: PRT
<213> ORGANISM: Aspergillus nidulans FGSC A4

<400> SEQUENCE: 7

Ala Thr Ala Ser Gly Asn Pro Phe Ser Gly Tyr Gln Leu Tyr Val Asn
1               5                   10                  15

Pro Tyr Tyr Ser Ser Glu Val Gln Ser Ile Ala Ile Pro Ser Leu Thr
                20                  25                  30

Gly Thr Leu Ser Ser Leu Ala Pro Ala Ala Thr Ala Ala Ala Lys Val
            35                  40                  45

Pro Ser Phe Val Trp Leu Asp Val Ala Ala Lys Val Pro Thr Met Ala
        50                  55                  60

Thr Tyr Leu Ala Asp Ile Arg Ser Gln Asn Ala Ala Gly Ala Asn Pro
65                  70                  75                  80

Pro Ile Ala Gly Gln Phe Val Val Tyr Asp Leu Pro Asp Arg Asp Cys
                85                  90                  95

Ala Ala Leu Ala Ser Asn Gly Glu Phe Ala Ile Ser Asp Gly Gly Val
            100                 105                 110

Gln His Tyr Lys Asp Tyr Ile Asp Ser Ile Arg Glu Ile Leu Val Glu
        115                 120                 125

Tyr Ser Asp Val His Val Ile Leu Val Ile Glu Pro Asp Ser Leu Ala
130                 135                 140

Asn Leu Val Thr Asn Leu Asn Val Ala Lys Cys Ala Asn Ala Gln Ser
145                 150                 155                 160

Ala Tyr Leu Glu Cys Thr Asn Tyr Ala Val Thr Gln Leu Asn Leu Pro
                165                 170                 175

Asn Val Ala Met Tyr Leu Asp Ala Gly His Ala Gly Trp Leu Gly Trp
            180                 185                 190

Pro Ala Asn Leu Gln Pro Ala Ala Asn Leu Tyr Ala Gly Val Tyr Ser
        195                 200                 205

Asp Ala Gly Ser Pro Ala Ala Leu Arg Gly Leu Ala Thr Asn Val Ala
    210                 215                 220

Asn Tyr Asn Ala Trp Ala Ile Asp Thr Cys Pro Ser Tyr Thr Gln Gly
225                 230                 235                 240

Asn Ser Val Cys Asp Glu Lys Asp Tyr Ile Asn Ala Leu Ala Pro Leu
```

```
                        245                 250                 255
Leu Arg Ala Gln Gly Phe Asp Ala His Phe Ile Thr Asp Thr Gly Arg
                260                 265                 270

Asn Gly Lys Gln Pro Thr Gly Gln Gln Ala Trp Gly Asp Trp Cys Asn
            275                 280                 285

Val Ile Gly Thr Gly Phe Gly Ala Arg Pro Ser Thr Asn Thr Gly Asp
        290                 295                 300

Ser Leu Leu Asp Ala Phe Val Trp Val Lys Pro Gly Gly Glu Ser Asp
305                 310                 315                 320

Gly Thr Ser Asp Thr Ser Ala Ala Arg Tyr Asp Ala His Cys Gly Tyr
                325                 330                 335

Ser Asp Ala Leu Gln Pro Ala Pro Glu Ala Gly Thr Trp Phe Gln Ala
            340                 345                 350

Tyr Phe Val Gln Leu Leu Gln Asn Ala Asn Pro Ser Phe
        355                 360                 365

<210> SEQ ID NO 8
<211> LENGTH: 365
<212> TYPE: PRT
<213> ORGANISM: Aspergillus niger CBS 513.88

<400> SEQUENCE: 8

Ala Ser Ala Ser Gly Asn Pro Phe Ser Gly Tyr Gln Leu Tyr Val Asn
1               5                   10                  15

Pro Tyr Tyr Ser Ser Glu Val Ala Ser Leu Ala Ile Pro Ser Leu Thr
            20                  25                  30

Gly Ser Leu Ser Ser Leu Gln Ala Ala Thr Ala Ala Ala Lys Val
        35                  40                  45

Pro Ser Phe Val Trp Leu Asp Thr Ala Ala Lys Val Pro Thr Met Gly
    50                  55                  60

Asp Tyr Leu Ala Asp Ile Gln Ser Gln Asn Ala Ala Gly Ala Asn Pro
65                  70                  75                  80

Pro Ile Ala Gly Gln Phe Val Val Tyr Asp Leu Pro Asp Arg Asp Cys
                85                  90                  95

Ala Ala Leu Ala Ser Asn Gly Glu Tyr Ser Ile Ala Asp Asn Gly Val
            100                 105                 110

Glu His Tyr Lys Ser Tyr Ile Asp Ser Ile Arg Glu Ile Leu Val Gln
        115                 120                 125

Tyr Ser Asp Val His Thr Leu Leu Val Ile Glu Pro Asp Ser Leu Ala
130                 135                 140

Asn Leu Val Thr Asn Leu Asn Val Ala Lys Cys Ala Asn Ala Glu Ser
145                 150                 155                 160

Ala Tyr Leu Glu Cys Thr Asn Tyr Ala Leu Thr Gln Leu Asn Leu Pro
                165                 170                 175

Asn Val Ala Met Tyr Leu Asp Ala Gly His Ala Gly Trp Leu Gly Trp
            180                 185                 190

Pro Ala Asn Gln Gln Pro Ala Ala Asp Leu Phe Ala Ser Val Tyr Lys
        195                 200                 205

Asn Ala Ser Ser Pro Ala Ala Val Arg Gly Leu Ala Thr Asn Val Ala
    210                 215                 220

Asn Tyr Asn Ala Trp Thr Ile Ser Ser Cys Pro Ser Tyr Thr Gln Gly
225                 230                 235                 240

Asn Ser Val Cys Asp Glu Gln Gln Tyr Ile Asn Ala Ile Ala Pro Leu
                245                 250                 255

Leu Gln Ala Gln Gly Phe Asp Ala His Phe Ile Val Asp Thr Gly Arg
```

```
                260                 265                 270
Asn Gly Lys Gln Pro Thr Gly Gln Gln Ala Trp Gly Asp Trp Cys Asn
            275                 280                 285
Val Ile Asn Thr Gly Phe Gly Glu Arg Pro Thr Thr Asp Thr Gly Asp
        290                 295                 300
Ala Leu Val Asp Ala Phe Val Trp Val Lys Pro Gly Gly Glu Ser Asp
305                 310                 315                 320
Gly Thr Ser Asp Ser Ser Ala Thr Arg Tyr Asp Ala His Cys Gly Tyr
                325                 330                 335
Ser Asp Ala Leu Gln Pro Ala Pro Glu Ala Gly Thr Trp Phe Gln Ala
            340                 345                 350
Tyr Phe Val Gln Leu Leu Thr Asn Ala Asn Pro Ala Phe
        355                 360                 365

<210> SEQ ID NO 9
<211> LENGTH: 362
<212> TYPE: PRT
<213> ORGANISM: Aspergillus oryzae RIB 40

<400> SEQUENCE: 9

Ala Thr Ala Gly Gly Asn Pro Phe Glu Gly Tyr Asp Leu Tyr Val Asn
1               5                   10                  15
Pro Tyr Tyr Lys Ser Glu Val Glu Ser Leu Ala Ile Pro Ser Met Thr
            20                  25                  30
Gly Ser Leu Ala Glu Lys Ala Ser Ala Ala Asn Val Pro Ser Phe
        35                  40                  45
His Trp Leu Asp Thr Thr Asp Lys Val Pro Gln Met Gly Glu Phe Leu
    50                  55                  60
Glu Asp Ile Lys Thr Lys Asn Ala Ala Gly Ala Asn Pro Pro Thr Ala
65                  70                  75                  80
Gly Ile Phe Val Val Tyr Asp Leu Pro Asp Arg Asp Cys Ala Ala Leu
                85                  90                  95
Ala Ser Asn Gly Glu Phe Leu Ile Ser Asp Gly Gly Val Glu Lys Tyr
            100                 105                 110
Lys Ala Tyr Ile Asp Ser Ile Arg Glu Gln Val Glu Lys Tyr Ser Asp
        115                 120                 125
Thr Gln Ile Ile Leu Val Ile Glu Pro Asp Ser Leu Ala Asn Leu Val
    130                 135                 140
Thr Asn Leu Asn Val Gln Lys Cys Ala Asn Ala Gln Asp Ala Tyr Leu
145                 150                 155                 160
Glu Cys Thr Asn Tyr Ala Leu Thr Gln Leu Asn Leu Pro Asn Val Ala
                165                 170                 175
Met Tyr Leu Asp Ala Gly His Ala Gly Trp Leu Gly Trp Pro Ala Asn
            180                 185                 190
Ile Gly Pro Ala Ala Glu Leu Tyr Ala Ser Val Tyr Lys Asn Ala Ser
        195                 200                 205
Ser Pro Ala Ala Val Arg Gly Leu Ala Thr Asn Val Ala Asn Tyr Asn
    210                 215                 220
Ala Phe Ser Ile Asp Ser Cys Pro Ser Tyr Thr Gln Gly Ser Thr Val
225                 230                 235                 240
Cys Asp Glu Lys Thr Tyr Ile Asn Asn Phe Ala Pro Gln Leu Lys Ser
                245                 250                 255
Ala Gly Phe Asp Ala His Phe Ile Val Asp Thr Gly Arg Asn Gly Asn
            260                 265                 270
Gln Pro Thr Gly Gln Ser Gln Trp Gly Asp Trp Cys Asn Val Lys Asn
```

```
                    275                 280                 285
Thr Gly Phe Gly Val Arg Pro Thr Thr Asp Thr Gly Asp Glu Leu Val
290                 295                 300

Asp Ala Phe Val Trp Val Lys Pro Gly Gly Glu Ser Asp Gly Thr Ser
305                 310                 315                 320

Asp Thr Ser Ala Glu Arg Tyr Asp Ala His Cys Gly Tyr Ala Asp Ala
                325                 330                 335

Leu Thr Pro Ala Pro Glu Ala Gly Thr Trp Phe Gln Ala Tyr Phe Glu
                340                 345                 350

Gln Leu Val Glu Asn Ala Asn Pro Ser Leu
                355                 360

<210> SEQ ID NO 10
<211> LENGTH: 363
<212> TYPE: PRT
<213> ORGANISM: Aspergillus niger CBS 513.88

<400> SEQUENCE: 10

Ala Ser Ala Thr Gly Asn Pro Phe Glu Gly Tyr Gln Leu Tyr Ala Asn
1               5                   10                  15

Pro Tyr Tyr Lys Ser Gln Val Glu Ser Ser Ala Ile Pro Ser Leu Ser
                20                  25                  30

Ala Ser Ser Leu Val Ala Gln Ala Ser Ala Ala Asp Val Pro Ser
            35                  40                  45

Phe Tyr Trp Leu Asp Thr Ala Asp Lys Val Pro Thr Met Gly Glu Tyr
        50                  55                  60

Leu Glu Asp Ile Gln Thr Gln Asn Ala Ala Gly Ala Ser Pro Pro Ile
65                  70                  75                  80

Ala Gly Ile Phe Val Val Tyr Asp Leu Pro Asp Arg Asp Cys Ser Ala
                85                  90                  95

Leu Ala Ser Asn Gly Glu Tyr Ser Ile Ser Asp Gly Gly Val Glu Lys
                100                 105                 110

Tyr Lys Ala Tyr Ile Asp Ser Ile Arg Glu Gln Val Glu Thr Tyr Ser
            115                 120                 125

Asp Val Gln Thr Ile Leu Ile Ile Glu Pro Asp Ser Leu Ala Asn Leu
130                 135                 140

Val Thr Asn Leu Asp Val Ala Lys Cys Ala Asn Ala Glu Ser Ala Tyr
145                 150                 155                 160

Leu Glu Cys Thr Asn Tyr Ala Leu Glu Gln Leu Asn Leu Pro Asn Val
                165                 170                 175

Ala Met Tyr Leu Asp Ala Gly His Ala Gly Trp Leu Gly Trp Pro Ala
                180                 185                 190

Asn Ile Gly Pro Ala Ala Gln Leu Tyr Ala Ser Val Tyr Lys Asn Ala
            195                 200                 205

Ser Ser Pro Ala Ala Val Arg Gly Leu Ala Thr Asn Val Ala Asn Phe
210                 215                 220

Asn Ala Trp Ser Ile Asp Ser Cys Pro Ser Tyr Thr Ser Gly Asn Asp
225                 230                 235                 240

Val Cys Asp Glu Lys Ser Tyr Ile Asn Ala Ile Ala Pro Glu Leu Ser
                245                 250                 255

Ser Ala Gly Phe Asp Ala His Phe Ile Thr Asp Thr Gly Arg Asn Gly
                260                 265                 270

Lys Gln Pro Thr Gly Gln Ser Ala Trp Gly Asp Trp Cys Asn Val Lys
            275                 280                 285

Asp Thr Gly Phe Gly Ala Gln Pro Thr Thr Asp Thr Gly Asp Glu Leu
```

```
            290                 295                 300
Ala Asp Ala Phe Val Trp Val Lys Pro Gly Gly Glu Ser Asp Gly Thr
305                 310                 315                 320

Ser Asp Thr Ser Ser Ser Arg Tyr Asp Ala His Cys Gly Tyr Ser Asp
                325                 330                 335

Ala Leu Gln Pro Ala Pro Glu Ala Gly Thr Trp Phe Gln Ala Tyr Phe
            340                 345                 350

Glu Gln Leu Leu Thr Asn Ala Asn Pro Ser Leu
            355                 360

<210> SEQ ID NO 11
<211> LENGTH: 364
<212> TYPE: PRT
<213> ORGANISM: Acremonium cellulolyticus Y-94

<400> SEQUENCE: 11

Ala Ala Ala Ser Gly Asn Pro Phe Ser Gly Tyr Gln Leu Tyr Ala Asn
1               5                   10                  15

Pro Tyr Tyr Ser Ser Glu Val His Thr Leu Ala Ile Pro Ser Leu Thr
            20                  25                  30

Gly Ser Leu Ala Ala Ala Thr Lys Ala Ala Glu Ile Pro Ser Phe
        35                  40                  45

Val Trp Leu Asp Thr Ala Ala Lys Val Pro Thr Met Gly Thr Tyr Leu
50                  55                  60

Ala Asn Ile Glu Ala Ala Asn Lys Ala Gly Ala Ser Pro Pro Ile Ala
65                  70                  75                  80

Gly Ile Phe Val Val Tyr Asp Leu Pro Asp Arg Asp Cys Ala Ala Ala
                85                  90                  95

Ala Ser Asn Gly Glu Tyr Thr Val Ala Asn Asn Gly Val Ala Asn Tyr
            100                 105                 110

Lys Ala Tyr Ile Asp Ser Ile Val Ala Gln Leu Lys Ala Tyr Pro Asp
        115                 120                 125

Val His Thr Ile Leu Ile Ile Glu Pro Asp Ser Leu Ala Asn Met Val
    130                 135                 140

Thr Asn Leu Ser Thr Ala Lys Cys Ala Glu Ala Gln Ser Ala Tyr Tyr
145                 150                 155                 160

Glu Cys Val Asn Tyr Ala Leu Ile Asn Leu Asn Leu Ala Asn Val Ala
                165                 170                 175

Met Tyr Ile Asp Ala Gly His Ala Gly Trp Leu Gly Trp Ser Ala Asn
            180                 185                 190

Leu Ser Pro Ala Ala Gln Leu Phe Ala Thr Val Tyr Lys Asn Ala Ser
        195                 200                 205

Ala Pro Ala Ser Leu Arg Gly Leu Ala Thr Asn Val Ala Asn Tyr Asn
    210                 215                 220

Ala Trp Ser Ile Ser Ser Pro Pro Ser Tyr Thr Ser Gly Asp Ser Asn
225                 230                 235                 240

Tyr Asp Glu Lys Leu Tyr Ile Asn Ala Leu Ser Pro Leu Leu Thr Ser
                245                 250                 255

Asn Gly Trp Pro Asn Ala His Phe Ile Met Asp Thr Ser Arg Asn Gly
            260                 265                 270

Val Gln Pro Thr Lys Gln Gln Ala Trp Gly Asp Trp Cys Asn Val Ile
        275                 280                 285

Gly Thr Gly Phe Gly Val Gln Pro Thr Thr Asn Thr Gly Asp Pro Leu
    290                 295                 300

Glu Asp Ala Phe Val Trp Val Lys Pro Gly Gly Glu Ser Asp Gly Thr
```

```
            305                 310                 315                 320
Ser Asn Ser Ser Ala Thr Arg Tyr Asp Phe His Cys Gly Tyr Ser Asp
                325                 330                 335

Ala Leu Gln Pro Ala Pro Glu Ala Gly Thr Trp Phe Gln Ala Tyr Phe
            340                 345                 350

Val Gln Leu Leu Thr Asn Ala Asn Pro Ala Leu Val
            355                 360

<210> SEQ ID NO 12
<211> LENGTH: 362
<212> TYPE: PRT
<213> ORGANISM: Talaromyces emersonii

<400> SEQUENCE: 12

Ala Ser Ala Ser Gly Asn Pro Phe Glu Gly Tyr Gln Leu Tyr Ala Asn
1               5                   10                  15

Pro Tyr Tyr Ala Ser Glu Val Ile Ser Leu Ala Ile Pro Ser Leu Ser
            20                  25                  30

Ser Glu Leu Val Pro Lys Ala Ser Glu Val Ala Lys Val Pro Ser Phe
        35                  40                  45

Val Trp Leu Asp Gln Ala Ala Lys Val Pro Ser Met Gly Asp Tyr Leu
50                  55                  60

Lys Asp Ile Gln Ser Gln Asn Ala Ala Gly Ala Asp Pro Pro Ile Ala
65                  70                  75                  80

Gly Ile Phe Val Val Tyr Asp Leu Pro Asp Arg Asp Cys Ala Ala Ala
                85                  90                  95

Ala Ser Asn Gly Glu Phe Ser Ile Ala Asn Asn Gly Val Ala Leu Tyr
            100                 105                 110

Lys Gln Tyr Ile Asp Ser Ile Arg Glu Gln Leu Thr Thr Tyr Ser Asp
        115                 120                 125

Val His Thr Ile Leu Val Ile Glu Pro Asp Ser Leu Ala Asn Val Val
    130                 135                 140

Thr Asn Leu Asn Val Pro Lys Cys Ala Asn Ala Gln Asp Ala Tyr Leu
145                 150                 155                 160

Glu Cys Ile Asn Tyr Ala Ile Thr Gln Leu Asp Leu Pro Asn Val Ala
                165                 170                 175

Met Tyr Leu Asp Ala Gly His Ala Gly Trp Leu Gly Trp Gln Ala Asn
            180                 185                 190

Leu Ala Pro Ala Ala Gln Leu Phe Ala Ser Val Tyr Lys Asn Ala Ser
        195                 200                 205

Ser Pro Ala Ser Val Arg Gly Leu Ala Thr Asn Val Ala Asn Tyr Asn
    210                 215                 220

Ala Trp Ser Ile Ser Arg Cys Pro Ser Tyr Thr Gln Gly Asp Ala Asn
225                 230                 235                 240

Cys Asp Glu Glu Asp Tyr Val Asn Ala Leu Gly Pro Leu Phe Gln Glu
                245                 250                 255

Gln Gly Phe Pro Ala Tyr Phe Ile Ile Asp Thr Ser Arg Asn Gly Val
            260                 265                 270

Arg Pro Thr Lys Gln Ser Gln Trp Gly Asp Trp Cys Asn Val Ile Gly
        275                 280                 285

Thr Gly Phe Gly Val Arg Pro Thr Thr Asp Thr Gly Asn Pro Leu Glu
    290                 295                 300

Asp Ala Phe Val Trp Val Lys Pro Gly Gly Glu Ser Asp Gly Thr Ser
305                 310                 315                 320

Asn Thr Thr Ser Pro Arg Tyr Asp Tyr His Cys Gly Leu Ser Asp Ala
```

Leu Gln Pro Ala Pro Glu Ala Gly Thr Trp Phe Gln Ala Tyr Phe Glu
            325                 330                 335

Gln Leu Leu Thr Asn Ala Asn Pro Leu Phe
            340                 345

<210> SEQ ID NO 13
<211> LENGTH: 361
<212> TYPE: PRT
<213> ORGANISM: Gibberella zeae K59

<400> SEQUENCE: 13

Pro Val Ala Thr Asn Asn Pro Phe Ser Gly Val Asp Leu Trp Ala Asn
1               5                   10                  15

Asn Tyr Tyr Arg Ser Glu Val Ser Thr Leu Ala Ile Pro Lys Leu Ser
            20                  25                  30

Gly Ala Met Ala Thr Ala Ala Lys Val Ala Asp Val Pro Ser Phe
            35                  40                  45

Gln Trp Met Asp Thr Tyr Asp His Ile Ser Phe Met Glu Asp Ser Leu
    50                  55                  60

Ala Asp Ile Arg Lys Ala Asn Lys Ala Gly Asn Tyr Ala Gly Gln
65                  70                  75                  80

Phe Val Val Tyr Asp Leu Pro Asp Arg Asp Cys Ala Ala Ala Ser
                85                  90                  95

Asn Gly Glu Tyr Ser Leu Asp Lys Asp Gly Lys Asn Lys Tyr Lys Ala
            100                 105                 110

Tyr Ile Ala Asp Gln Gly Ile Leu Gln Asp Tyr Ser Asp Thr Arg Ile
            115                 120                 125

Ile Leu Val Ile Glu Pro Asp Ser Leu Ala Asn Met Val Thr Asn Met
    130                 135                 140

Asn Val Pro Lys Cys Ala Asn Ala Ala Ser Ala Tyr Lys Glu Leu Thr
145                 150                 155                 160

Ile His Ala Leu Lys Glu Leu Asn Leu Pro Asn Val Ser Met Tyr Ile
                165                 170                 175

Asp Ala Gly His Gly Gly Trp Leu Gly Trp Pro Ala Asn Leu Pro Pro
            180                 185                 190

Ala Ala Gln Leu Tyr Gly Gln Leu Tyr Lys Asp Ala Gly Lys Pro Ser
            195                 200                 205

Arg Leu Arg Gly Leu Val Thr Asn Val Ser Asn Tyr Asn Ala Trp Lys
    210                 215                 220

Leu Ser Ser Lys Pro Asp Tyr Thr Glu Ser Asn Pro Asn Tyr Asp Glu
225                 230                 235                 240

Gln Lys Tyr Ile His Ala Leu Ser Pro Leu Leu Glu Gln Glu Gly Trp
                245                 250                 255

Pro Gly Ala Lys Phe Ile Val Asp Gln Gly Arg Ser Gly Lys Gln Pro
            260                 265                 270

Thr Gly Gln Lys Ala Trp Gly Asp Trp Cys Asn Ala Pro Gly Thr Gly
            275                 280                 285

Phe Gly Leu Arg Pro Ser Ala Asn Thr Gly Asp Ala Leu Val Asp Ala
    290                 295                 300

Phe Val Trp Val Lys Pro Gly Gly Glu Ser Asp Gly Thr Ser Asp Thr
305                 310                 315                 320

Ser Ala Ala Arg Tyr Asp Tyr His Cys Gly Ile Asp Gly Ala Val Lys
                325                 330                 335

Pro Ala Pro Glu Ala Gly Thr Trp Phe Gln Ala Tyr Phe Glu Gln Leu

Leu Lys Asn Ala Asn Pro Ser Phe Leu
        355                 360

<210> SEQ ID NO 14
<211> LENGTH: 362
<212> TYPE: PRT
<213> ORGANISM: Fusarium oxysporum

<400> SEQUENCE: 14

Pro Ala Ala Ser Asp Asn Pro Tyr Ala Gly Val Asp Leu Trp Ala Asn
1               5                   10                  15

Asn Tyr Tyr Arg Ser Glu Val Met Asn Leu Ala Val Pro Lys Leu Ser
            20                  25                  30

Gly Ala Lys Ala Thr Ala Ala Lys Val Ala Asp Val Pro Ser Phe
        35                  40                  45

Gln Trp Met Asp Thr Tyr Asp His Ile Ser Leu Met Glu Asp Thr Leu
    50                  55                  60

Ala Asp Ile Arg Lys Ala Asn Lys Ala Gly Gly Lys Tyr Ala Gly Gln
65                  70                  75                  80

Phe Val Val Tyr Asp Leu Pro Asn Arg Asp Cys Ala Ala Ala Ser
                85                  90                  95

Asn Gly Glu Tyr Ser Leu Asp Lys Asp Gly Ala Asn Lys Tyr Lys Ala
            100                 105                 110

Tyr Ile Ala Lys Ile Lys Gly Ile Leu Gln Asn Tyr Ser Asp Thr Lys
        115                 120                 125

Val Ile Leu Val Ile Glu Pro Asp Ser Leu Ala Asn Leu Val Thr Asn
    130                 135                 140

Leu Asn Val Asp Lys Cys Ala Lys Ala Glu Ser Ala Tyr Lys Glu Leu
145                 150                 155                 160

Thr Val Tyr Ala Ile Lys Glu Leu Asn Leu Pro Asn Val Ser Met Tyr
                165                 170                 175

Leu Asp Ala Gly His Gly Gly Trp Leu Gly Trp Pro Ala Asn Ile Gly
            180                 185                 190

Pro Ala Ala Lys Leu Tyr Ala Gln Ile Tyr Lys Asp Ala Gly Lys Pro
        195                 200                 205

Ser Arg Val Arg Gly Leu Val Thr Asn Val Ser Asn Tyr Asn Gly Trp
    210                 215                 220

Lys Leu Ser Thr Lys Pro Asp Tyr Thr Glu Ser Asn Pro Asn Tyr Asp
225                 230                 235                 240

Glu Gln Arg Tyr Ile Asn Ala Phe Ala Pro Leu Leu Ala Gln Glu Gly
                245                 250                 255

Trp Ser Asn Val Lys Phe Ile Val Asp Gln Gly Arg Ser Gly Lys Gln
            260                 265                 270

Pro Thr Gly Gln Lys Ala Gln Gly Asp Trp Cys Asn Ala Lys Gly Thr
        275                 280                 285

Gly Phe Gly Leu Arg Pro Ser Thr Asn Thr Gly Asp Ala Leu Ala Asp
    290                 295                 300

Ala Phe Val Trp Val Lys Pro Gly Gly Glu Ser Asp Gly Thr Ser Asp
305                 310                 315                 320

Thr Ser Ala Ala Arg Tyr Asp Tyr His Cys Gly Leu Asp Asp Ala Leu
                325                 330                 335

Lys Pro Ala Pro Glu Ala Gly Thr Trp Phe Gln Ala Tyr Phe Glu Gln
            340                 345                 350

Leu Leu Asp Asn Ala Asn Pro Ser Phe Leu
        355                 360

<210> SEQ ID NO 15
<211> LENGTH: 363
<212> TYPE: PRT
<213> ORGANISM: Neurospora crassa OR74A

<400> SEQUENCE: 15

```
Ala Ser Phe Thr Gly Asn Pro Phe Leu Gly Val Gln Gly Trp Ala Asn
1               5                   10                  15

Ser Tyr Tyr Ser Ser Glu Ile Tyr Asn His Ala Ile Pro Ser Met Thr
            20                  25                  30

Gly Ser Leu Ala Ala Gln Ala Ser Ala Val Ala Lys Val Pro Thr Phe
        35                  40                  45

Gln Trp Leu Asp Arg Asn Val Thr Val Asp Thr Leu Met Lys Ser Thr
    50                  55                  60

Leu Glu Glu Ile Arg Ala Ala Asn Lys Ala Gly Ala Asn Pro Pro Tyr
65                  70                  75                  80

Ala Ala His Phe Val Val Tyr Asp Leu Pro Asp Arg Asp Cys Ala Ala
                85                  90                  95

Ala Ala Ser Asn Gly Glu Phe Ser Ile Ala Asn Gly Gly Val Ala Asn
            100                 105                 110

Tyr Lys Thr Tyr Ile Asn Ala Ile Arg Lys Leu Leu Ile Glu Tyr Ser
        115                 120                 125

Asp Ile Arg Thr Ile Leu Val Ile Glu Pro Asp Ser Leu Ala Asn Leu
    130                 135                 140

Val Thr Asn Thr Asn Val Ala Lys Cys Ala Asn Ala Ala Ser Ala Tyr
145                 150                 155                 160

Arg Glu Cys Thr Asn Tyr Ala Ile Thr Gln Leu Asp Leu Pro His Val
                165                 170                 175

Ala Gln Tyr Leu Asp Ala Gly His Gly Gly Trp Leu Gly Trp Pro Ala
            180                 185                 190

Asn Ile Gln Pro Ala Ala Thr Leu Phe Ala Asp Ile Tyr Lys Ala Ala
        195                 200                 205

Gly Lys Pro Lys Ser Val Arg Gly Leu Val Thr Asn Val Ser Asn Tyr
    210                 215                 220

Asn Gly Trp Ser Leu Ser Ser Ala Pro Ser Tyr Thr Thr Pro Asn Pro
225                 230                 235                 240

Asn Tyr Asp Glu Lys Lys Tyr Ile Glu Ala Phe Ser Pro Leu Leu Asn
                245                 250                 255

Ala Ala Gly Phe Pro Ala Gln Phe Ile Val Asp Thr Gly Arg Ser Gly
            260                 265                 270

Lys Gln Pro Thr Gly Gln Ile Glu Gln Gly Asp Trp Cys Asn Ala Ile
        275                 280                 285

Gly Thr Gly Phe Gly Val Arg Pro Thr Thr Asn Thr Gly Ser Ser Leu
    290                 295                 300

Ala Asp Ala Phe Val Trp Val Lys Pro Gly Gly Glu Ser Asp Gly Thr
305                 310                 315                 320

Ser Asp Thr Ser Ala Thr Arg Tyr Asp Tyr His Cys Gly Leu Ser Asp
                325                 330                 335

Ala Leu Lys Pro Ala Pro Glu Ala Gly Gln Trp Phe Gln Ala Tyr Phe
            340                 345                 350

Glu Gln Leu Leu Lys Asn Ala Asn Pro Ala Phe
        355                 360
```

```
<210> SEQ ID NO 16
<211> LENGTH: 364
<212> TYPE: PRT
<213> ORGANISM: Aspergillus nidulans FGSC A4

<400> SEQUENCE: 16

Val Gln Ala Thr Gly Asn Pro Phe Glu Gly Tyr Gln Leu Tyr Ala Asn
 1               5                  10                  15

Pro Tyr Tyr Ser Ser Glu Val Met Thr Leu Ala Val Pro Ser Met Thr
             20                  25                  30

Gly Ser Leu Ala Glu Gln Ala Thr His Ala Ala Glu Ile Pro Ser Phe
         35                  40                  45

His Trp Leu Asp Thr Thr Ala Lys Val Pro Thr Met Gly Glu Tyr Leu
     50                  55                  60

Ala Asp Ile Lys Glu Gln Asn Asp Ala Gly Ala Asn Pro Pro Ile Ala
 65                  70                  75                  80

Gly Ile Phe Val Val Tyr Asn Leu Pro Asp Arg Asp Cys Ala Ala Leu
                 85                  90                  95

Ala Ser Asn Gly Glu Leu Ser Ile Ala Asp Gly Gly Val Glu Lys Tyr
            100                 105                 110

Lys Glu Tyr Ile Asp Ala Ile Arg Ala His Ala Val Glu Tyr Ser Asp
        115                 120                 125

Thr Asn Ile Ile Leu Ile Ile Glu Pro Asp Ser Leu Ala Asn Leu Val
130                 135                 140

Thr Asn Leu Asn Val Glu Lys Cys Ala Asn Ala Gln Asp Ala Tyr Leu
145                 150                 155                 160

Glu Cys Thr Asn Tyr Ala Ile Thr Gln Leu Asp Leu Pro Asn Val Ser
                165                 170                 175

Met Tyr Leu Asp Ala Gly His Ala Gly Trp Leu Gly Trp Pro Ala Asn
            180                 185                 190

Ile Gly Pro Ala Ala Gln Leu Phe Ala Gly Val Tyr Gln Asp Ala Gly
        195                 200                 205

Ala Pro Ala Ala Leu Arg Gly Leu Ala Thr Asn Val Ala Asn Tyr Asn
    210                 215                 220

Ala Phe Ser Ile Asp Thr Cys Pro Ser Tyr Thr Ser Gln Asn Ala Val
225                 230                 235                 240

Cys Asp Glu Lys Gly Tyr Ile Asn Ser Phe Ala Pro Glu Leu Ser Ala
                245                 250                 255

Ala Gly Trp Asp Ala His Phe Ile Val Asp Thr Gly Arg Asn Gly Lys
            260                 265                 270

Gln Pro Thr Gly Gln Ile Glu Trp Gly Asp Trp Cys Asn Val Lys Gly
        275                 280                 285

Thr Gly Phe Gly Val Arg Pro Thr Thr Asp Thr Gly Asp Glu Leu Val
    290                 295                 300

Asp Ala Phe Val Trp Val Lys Pro Gly Gly Glu Ser Asp Gly Thr Ser
305                 310                 315                 320

Asp Gln Ser Ala Glu Arg Tyr Asp Ala His Cys Gly Ala Ala Ala Ala
                325                 330                 335

Leu Gln Pro Ala Pro Glu Ala Gly Thr Trp Phe Gln Ala Tyr Phe Glu
            340                 345                 350

Gln Leu Val Ala Asn Ala Asn Pro Pro Leu Ser Ser
        355                 360

<210> SEQ ID NO 17
<211> LENGTH: 363
<212> TYPE: PRT
```

```
<213> ORGANISM: Aspergillus tubingensis
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid

<400> SEQUENCE: 17
```

Ala Ser Ala Thr Gly Asn Pro Phe Glu Gly Tyr Gln Leu Tyr Val Asn
1               5                  10                  15

Pro Tyr Tyr Lys Ser Gln Val Glu Ser Ser Ala Ile Pro Ser Leu Ser
            20                  25                  30

Ala Ser Ser Leu Val Ala Gln Ala Ser Ala Ala Asp Val Pro Ser
        35                  40                  45

Phe Tyr Trp Leu Asp Thr Ala Asp Lys Val Pro Thr Met Gly Glu Tyr
    50                  55                  60

Leu Asp Asp Ile Gln Thr Gln Asn Ala Ala Gly Ala Asn Pro Pro Ile
65                  70                  75                  80

Ala Gly Ile Phe Val Val Tyr Asp Leu Pro Asp Arg Asp Cys Ala Ala
                85                  90                  95

Leu Ala Ser Asn Gly Glu Tyr Ala Ile Ser Asp Gly Gly Val Glu Lys
            100                 105                 110

Tyr Lys Ala Tyr Ile Asp Ser Ile Arg Glu Gln Val Glu Thr Tyr Ser
        115                 120                 125

Asp Val Gln Thr Ile Leu Ile Ile Glu Pro Asp Ser Leu Ala Asn Leu
    130                 135                 140

Val Thr Asn Leu Asp Val Ala Lys Cys Ala Asn Ala Gln Ser Ala Tyr
145                 150                 155                 160

Leu Glu Cys Thr Asn Tyr Ala Leu Glu Gln Leu Asn Leu Pro Asn Val
                165                 170                 175

Ala Met Tyr Leu Asp Ala Gly His Ala Gly Trp Leu Gly Trp Pro Ala
            180                 185                 190

Asn Ile Gly Pro Ala Ala Glu Leu Tyr Ala Ser Val Tyr Lys Asn Ala
        195                 200                 205

Ser Ser Pro Ala Ala Val Arg Gly Leu Ala Thr Asx Val Ala Asn Phe
    210                 215                 220

Asn Ala Trp Ser Ile Asp Thr Cys Pro Ser Tyr Thr Ser Gly Asn Asp
225                 230                 235                 240

Val Cys Asp Glu Lys Ser Tyr Ile Asn Ala Phe Ala Pro Glu Leu Ser
                245                 250                 255

Xaa Ala Gly Phe Asp Ala His Phe Ile Thr Asp Thr Gly Arg Asn Gly
            260                 265                 270

Lys Gln Pro Thr Gly Gln Ser Ala Trp Gly Asp Trp Gly Asn Val Lys
        275                 280                 285

Asp Thr Gly Phe Gly Ala Xaa Pro Thr Thr Asp Thr Gly Asn Glu Leu
    290                 295                 300

Ala Asp Ala Phe Val Trp Xaa Asn Pro Gly Gly Lys Ser Asp Gly Thr
305                 310                 315                 320

Ser Asp Thr Ser Ser Ser Arg Tyr Asp Ala His Cys Gly Tyr Ser Asp
                325                 330                 335

Ala Leu Gln Pro Ala Pro Glu Ala Gly Thr Trp Phe Gln Ala Tyr Phe

```
            340                 345                 350
Glu Gln Leu Leu Thr Asn Ala Asn Pro Ser Leu
        355                 360

<210> SEQ ID NO 18
<211> LENGTH: 362
<212> TYPE: PRT
<213> ORGANISM: Magnaporthe grisea 70-15

<400> SEQUENCE: 18

Ala Ser Phe Thr Gly Asn Pro Phe Ala Gly Val Asn Leu Phe Pro Asn
1               5                   10                  15

Lys Phe Tyr Ser Ser Glu Val His Thr Leu Ala Ile Pro Ser Leu Thr
            20                  25                  30

Gly Ser Leu Val Ala Lys Ala Ser Ala Val Ala Gln Val Pro Ser Phe
        35                  40                  45

Gln Trp Leu Asp Ile Ala Ala Lys Val Glu Thr Leu Met Pro Gly Ala
    50                  55                  60

Leu Ala Asp Val Arg Ala Ala Asn Ala Ala Gly Gly Asn Tyr Ala Ala
65                  70                  75                  80

Gln Leu Val Val Tyr Asp Leu Pro Asp Arg Asp Cys Ala Ala Ala Ala
                85                  90                  95

Ser Asn Gly Glu Phe Ser Ile Ala Asp Gly Gly Val Val Lys Tyr Lys
            100                 105                 110

Ala Tyr Ile Asp Ala Ile Arg Lys Gln Leu Leu Ala Tyr Ser Asp Val
        115                 120                 125

Arg Thr Ile Leu Val Ile Glu Pro Asp Ser Leu Ala Asn Met Val Thr
    130                 135                 140

Asn Met Gly Val Pro Lys Cys Ala Gly Ala Lys Asp Ala Tyr Leu Glu
145                 150                 155                 160

Cys Thr Ile Tyr Ala Val Lys Gln Leu Asn Leu Pro His Val Ala Met
                165                 170                 175

Tyr Leu Asp Gly Gly His Ala Gly Trp Leu Gly Trp Pro Ala Asn Leu
            180                 185                 190

Gln Pro Ala Ala Asp Leu Phe Gly Lys Leu Tyr Ala Asp Ala Gly Lys
        195                 200                 205

Pro Ser Gln Leu Arg Gly Met Ala Thr Asn Val Ala Asn Tyr Asn Ala
    210                 215                 220

Trp Asp Leu Thr Thr Ala Pro Ser Tyr Thr Thr Pro Asn Pro Asn Phe
225                 230                 235                 240

Asp Glu Lys Lys Tyr Ile Ser Ala Phe Ala Pro Leu Leu Ala Ala Lys
                245                 250                 255

Gly Trp Ser Ala His Phe Ile Ile Asp Gln Gly Arg Ser Gly Lys Gln
            260                 265                 270

Pro Thr Gly Gln Lys Glu Trp Gly His Trp Cys Asn Gln Gln Gly Val
        275                 280                 285

Gly Phe Gly Arg Arg Pro Ser Ala Asn Thr Gly Ser Glu Leu Ala Asp
    290                 295                 300

Ala Phe Val Trp Ile Lys Pro Gly Gly Glu Cys Asp Gly Val Ser Asp
305                 310                 315                 320

Pro Thr Ala Pro Arg Phe Asp His Phe Cys Gly Thr Asp Tyr Gly Ala
                325                 330                 335

Met Ser Asp Ala Pro Gln Ala Gly Gln Trp Phe Gln Lys Tyr Phe Glu
            340                 345                 350

Met Leu Leu Thr Asn Ala Asn Pro Pro Leu
```

<210> SEQ ID NO 19
<211> LENGTH: 364
<212> TYPE: PRT
<213> ORGANISM: Chaetomium thermophilum

<400> SEQUENCE: 19

Ala Ser Tyr Asn Gly Asn Pro Phe Ser Gly Val Gln Leu Trp Ala Asn
1               5                   10                  15

Thr Tyr Tyr Ser Ser Glu Val His Thr Leu Ala Ile Pro Ser Leu Ser
            20                  25                  30

Pro Glu Leu Ala Ala Lys Ala Ala Lys Val Ala Glu Val Pro Ser Phe
        35                  40                  45

Gln Trp Leu Asp Arg Asn Val Thr Val Asp Thr Leu Phe Ser Gly Thr
    50                  55                  60

Leu Ala Glu Ile Arg Ala Ala Asn Gln Arg Gly Ala Asn Pro Pro Tyr
65                  70                  75                  80

Ala Gly Ile Phe Val Val Tyr Asp Leu Pro Asp Arg Asp Cys Ala Ala
                85                  90                  95

Ala Ala Ser Asn Gly Glu Trp Ser Ile Ala Asn Asn Gly Ala Asn Asn
            100                 105                 110

Tyr Lys Arg Tyr Ile Asp Arg Ile Arg Glu Leu Leu Ile Gln Tyr Ser
        115                 120                 125

Asp Ile Arg Thr Ile Leu Val Ile Glu Pro Asp Ser Leu Ala Asn Met
    130                 135                 140

Val Thr Asn Met Asn Val Gln Lys Cys Ser Asn Ala Ala Ser Thr Tyr
145                 150                 155                 160

Lys Glu Leu Thr Val Tyr Ala Leu Lys Gln Leu Asn Leu Pro His Val
                165                 170                 175

Ala Met Tyr Met Asp Ala Gly His Ala Gly Trp Leu Gly Trp Pro Ala
            180                 185                 190

Asn Ile Gln Pro Ala Ala Glu Leu Phe Ala Gln Ile Tyr Arg Asp Ala
        195                 200                 205

Gly Arg Pro Ala Ala Val Arg Gly Leu Ala Thr Asn Val Ala Asn Tyr
    210                 215                 220

Asn Ala Trp Ser Ile Ala Ser Pro Pro Ser Tyr Thr Ser Pro Asn Pro
225                 230                 235                 240

Asn Tyr Asp Glu Lys His Tyr Ile Glu Ala Phe Ala Pro Leu Leu Arg
                245                 250                 255

Asn Gln Gly Phe Asp Ala Lys Phe Ile Val Asp Thr Gly Arg Asn Gly
            260                 265                 270

Lys Gln Pro Thr Gly Gln Leu Glu Trp Gly His Trp Cys Asn Val Lys
        275                 280                 285

Gly Thr Gly Phe Gly Val Arg Pro Thr Ala Asn Thr Gly His Glu Leu
    290                 295                 300

Val Asp Ala Phe Val Trp Val Lys Pro Gly Gly Glu Ser Asp Gly Thr
305                 310                 315                 320

Ser Ala Asp Thr Ser Ala Ala Arg Tyr Asp Tyr His Cys Gly Leu Ser
                325                 330                 335

Asp Ala Leu Thr Pro Ala Pro Glu Ala Gly Gln Trp Phe Gln Ala Tyr
            340                 345                 350

Phe Glu Gln Leu Leu Ile Asn Ala Asn Pro Pro Leu
        355                 360

<210> SEQ ID NO 20
<211> LENGTH: 363
<212> TYPE: PRT
<213> ORGANISM: Chaetomium thermophilum CT2

<400> SEQUENCE: 20

Ala Ser Tyr Asn Gly Asn Pro Phe Ser Gly Val Gln Leu Trp Ala Asn
1               5                   10                  15

Thr Tyr Tyr Ser Ser Glu Val His Thr Leu Ala Ile Pro Ser Leu Ser
            20                  25                  30

Pro Glu Leu Ala Ala Lys Ala Ala Lys Val Ala Glu Val Pro Ser Phe
        35                  40                  45

Gln Trp Leu Asp Arg Asn Val Thr Val Asp Thr Leu Phe Ser Gly Thr
    50                  55                  60

Leu Ala Glu Ile Arg Ala Ala Asn Gln Arg Gly Ala Asn Pro Pro Tyr
65                  70                  75                  80

Ala Gly Ile Phe Val Val Tyr Asp Leu Pro Asp Arg Asp Cys Ala Ala
                85                  90                  95

Ala Ala Ser Asn Gly Glu Trp Ser Ile Ala Asn Asn Gly Ala Asn Asn
            100                 105                 110

Leu Gln Arg Tyr Ile Asp Arg Ile Arg Glu Leu Leu Ile Gln Tyr Ser
        115                 120                 125

Asp Ile Arg Thr Ile Leu Val Ile Glu Pro Asp Ser Leu Ala Asn Met
    130                 135                 140

Val Thr Asn Met Asn Val Gln Lys Cys Ser Asn Ala Ala Ser Thr Tyr
145                 150                 155                 160

Lys Glu Leu Thr Val Tyr Ala Leu Lys Gln Leu Asn Leu Pro His Val
                165                 170                 175

Ala Met Tyr Met Asp Ala Gly His Ala Gly Trp Leu Gly Trp Pro Ala
            180                 185                 190

Asn Ile Gln Pro Ala Ala Glu Leu Phe Ala Gln Ile Tyr Arg Asp Ala
        195                 200                 205

Gly Arg Pro Ala Ala Val Arg Gly Leu Ala Thr Asn Val Ala Asn Tyr
    210                 215                 220

Asn Ala Trp Ser Ile Ala Ser Pro Pro Ser Tyr Thr Ser Pro Asn Pro
225                 230                 235                 240

Asn Tyr Asp Glu Lys His Tyr Ile Glu Ala Phe Ala Pro Leu Leu Arg
                245                 250                 255

Asn Gln Gly Phe Asp Ala Lys Phe Ile Val Asp Thr Gly Arg Asn Gly
            260                 265                 270

Lys Gln Pro Thr Gly Gln Leu Glu Trp Gly His Trp Cys Asn Val Lys
        275                 280                 285

Gly Thr Gly Phe Gly Val Arg Pro Thr Ala Asn Thr Gly His Glu Leu
    290                 295                 300

Val Asp Ala Phe Val Trp Val Lys Pro Gly Gly Glu Ser Asp Gly Thr
305                 310                 315                 320

Ser Asp Thr Ser Ala Ala Arg Tyr Asp Tyr His Cys Gly Leu Ser Asp
                325                 330                 335

Ala Leu Thr Pro Ala Pro Glu Ala Gly Gln Trp Phe Gln Ala Tyr Phe
            340                 345                 350

Glu Gln Leu Leu Ile Asn Ala Asn Pro Pro Phe
        355                 360

<210> SEQ ID NO 21
<211> LENGTH: 360
<212> TYPE: PRT

<213> ORGANISM: Stilbella annulata

<400> SEQUENCE: 21

| | | | | | | | | | | | | | | | |
|---|---|---|---|---|---|---|---|---|---|---|---|---|---|---|---|
| Ala | Thr | Tyr | Thr | Gly | Asn | Pro | Phe | Leu | Gly | Val | Asn | Gln | Trp | Ala | Asn |
| 1 | | | | 5 | | | | | 10 | | | | | 15 | |
| Asn | Phe | Tyr | Arg | Ser | Glu | Ile | Met | Asn | Ile | Ala | Val | Pro | Ser | Leu | Ser |
| | | | 20 | | | | | 25 | | | | | 30 | | |
| Gly | Ala | Met | Ala | Thr | Ala | Ala | Lys | Val | Ala | Asp | Val | Pro | Thr | Phe | |
| | | 35 | | | | | 40 | | | | | 45 | | | |
| Gln | Trp | Ile | Asp | Lys | Met | Asp | Lys | Leu | Pro | Leu | Ile | Asp | Glu | Ala | Leu |
| | 50 | | | | | 55 | | | | | 60 | | | | |
| Ala | Asp | Val | Arg | Ala | Ala | Asn | Ala | Arg | Gly | Gly | Asn | Tyr | Ala | Ser | Ile |
| 65 | | | | | 70 | | | | | 75 | | | | | 80 |
| Leu | Val | Val | Tyr | Asn | Leu | Pro | Asp | Arg | Asp | Cys | Ala | Ala | Ala | Ser |
| | | | | 85 | | | | | 90 | | | | | 95 |
| Asn | Gly | Glu | Phe | Ala | Ile | Ala | Asp | Gly | Gly | Val | Ala | Lys | Tyr | Lys | Asn |
| | | | 100 | | | | | 105 | | | | | 110 | | |
| Tyr | Ile | Asp | Glu | Ile | Arg | Lys | Leu | Val | Ile | Lys | Tyr | Asn | Asp | Leu | Arg |
| | | 115 | | | | | 120 | | | | | 125 | | | |
| Ile | Ile | Leu | Val | Ile | Glu | Pro | Asp | Ser | Leu | Ala | Asn | Met | Val | Thr | Asn |
| 130 | | | | | 135 | | | | | 140 | | | | | |
| Met | Asn | Val | Ala | Lys | Cys | Gln | Asn | Ala | Ala | Ser | Ala | Tyr | Arg | Glu | Cys |
| 145 | | | | | 150 | | | | | 155 | | | | | 160 |
| Thr | Asn | Tyr | Ala | Leu | Thr | Asn | Leu | Asp | Leu | Pro | Asn | Val | Ala | Gln | Tyr |
| | | | | 165 | | | | | 170 | | | | | 175 | |
| Met | Asp | Ala | Gly | His | Ala | Gly | Trp | Leu | Gly | Trp | Pro | Ala | Asn | Ile | Thr |
| | | | 180 | | | | | 185 | | | | | 190 | | |
| Pro | Ala | Ala | Gln | Leu | Phe | Ala | Glu | Val | Tyr | Lys | Gln | Ala | Gly | Ser | Pro |
| | | 195 | | | | | 200 | | | | | 205 | | | |
| Lys | Ser | Val | Arg | Gly | Leu | Ala | Ile | Asn | Val | Ser | Asn | Tyr | Asn | Ala | Trp |
| 210 | | | | | 215 | | | | | 220 | | | | | |
| Ser | Val | Ser | Ser | Pro | Pro | Tyr | Thr | Ser | Pro | Asn | Pro | Asn | Tyr | Asp |
| 225 | | | | 230 | | | | | 235 | | | | | 240 |
| Glu | Arg | His | Phe | Val | Glu | Ala | Phe | Ala | Pro | Leu | Leu | Arg | Gln | Asn | Gly |
| | | | 245 | | | | | 250 | | | | | 255 | | |
| Trp | Asp | Ala | Lys | Phe | Ile | Val | Asp | Gln | Gly | Arg | Ser | Gly | Arg | Gln | Pro |
| | | | 260 | | | | | 265 | | | | | 270 | | |
| Thr | Gly | Gln | Gln | Glu | Trp | Gly | His | Trp | Cys | Asn | Ala | Ile | Gly | Thr | Gly |
| | | 275 | | | | | 280 | | | | | 285 | | | |
| Phe | Gly | Gln | Arg | Pro | Thr | Ser | Asn | Thr | Gly | His | Ala | Asp | Val | Asp | Ala |
| | 290 | | | | | 295 | | | | | 300 | | | | |
| Phe | Val | Trp | Ile | Lys | Pro | Gly | Gly | Glu | Cys | Asp | Gly | Thr | Ser | Asp | Thr |
| 305 | | | | | 310 | | | | | 315 | | | | | 320 |
| Ser | Ala | Ala | Arg | Tyr | Asp | His | Phe | Cys | Gly | Asn | Pro | Asp | Ala | Leu | Lys |
| | | | | 325 | | | | | 330 | | | | | 335 | |
| Pro | Ala | Pro | Glu | Ala | Gly | Glu | Trp | Phe | Gln | Ala | Tyr | Phe | Glu | Gln | Leu |
| | | | 340 | | | | | 345 | | | | | 350 | | |
| Leu | Arg | Asn | Ala | Asn | Pro | Ala | Phe |
| | | | 355 | | | | 360 |

<210> SEQ ID NO 22
<211> LENGTH: 453
<212> TYPE: PRT
<213> ORGANISM: Humicola insolens

<400> SEQUENCE: 22

-continued

```
Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
                35                  40                  45

Thr Ser Thr Ser Ser Ser Thr Thr Ser Arg Ala Thr Ser Thr Thr
    50                  55                  60

Arg Thr Gly Gly Val Thr Ser Ile Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
                115                 120                 125

Ala Ser Ala Val Ala Glu Val Pro Ser Phe Gln Trp Leu Asp Arg Asn
130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
                180                 185                 190

Trp Ala Ile Ala Asn Asn Gly Ala Asn Asn Tyr Lys Gly Tyr Ile Asn
            195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
                260                 265                 270

Gly His Ala Gly Trp Leu Gly Trp Pro Ala Asn Ile Gln Pro Ala Ala
            275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
            355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
```

```
                        420             425             430
Glu Ala Gly Gln Trp Phe Gln Ala Tyr Phe Glu Gln Leu Leu Arg Asn
                435                 440                 445

Ala Asn Pro Pro Phe
    450

<210> SEQ ID NO 23
<211> LENGTH: 360
<212> TYPE: PRT
<213> ORGANISM: Humicola insolens

<400> SEQUENCE: 23

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ala Ser Ala Val Ala Glu Val Pro Ser Phe Gln Trp Leu
            35                  40                  45

Asp Arg Asn Val Thr Val Asp Thr Leu Leu Val Gln Thr Leu Ser Glu
        50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
    130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
    210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Gln Phe Ile Val Asp Gln Gly Arg Ser Gly Lys Gln Pro
            260                 265                 270

Thr Gly Gln Lys Glu Trp Gly His Trp Cys Asn Ala Ile Gly Thr Gly
        275                 280                 285

Phe Gly Met Arg Pro Thr Ala Asn Thr Gly His Gln Tyr Val Asp Ala
    290                 295                 300

Phe Val Trp Val Lys Pro Gly Gly Glu Cys Asp Gly Thr Ser Asp Thr
305                 310                 315                 320

Thr Ala Ala Arg Tyr Asp Tyr His Cys Gly Leu Glu Asp Ala Leu Lys
                325                 330                 335

Pro Ala Pro Glu Ala Gly Gln Trp Phe Asn Glu Tyr Phe Ile Gln Leu
```

Leu Arg Asn Ala Asn Pro Pro Phe
            355                 360

<210> SEQ ID NO 24
<211> LENGTH: 362
<212> TYPE: PRT
<213> ORGANISM: Cochliobolus heterostrophus C4

<400> SEQUENCE: 24

Ala Ala Pro Ser Gly Asn Pro Phe Ala Gly Lys Asn Phe Tyr Ala Asn
1               5                   10                  15

Pro Tyr Tyr Ser Ser Glu Val His Thr Leu Ala Met Pro Ser Leu Pro
            20                  25                  30

Ala Ser Leu Lys Pro Ala Ala Thr Ala Val Ala Lys Val Gly Ser Phe
        35                  40                  45

Val Trp Met Asp Thr Met Ala Lys Val Pro Leu Met Asp Thr Tyr Leu
    50                  55                  60

Ala Asp Ile Lys Ala Lys Asn Ala Ala Gly Ala Asn Leu Met Gly Thr
65                  70                  75                  80

Phe Val Val Tyr Asp Leu Pro Asp Arg Asp Cys Ala Ala Leu Ala Ser
                85                  90                  95

Asn Gly Glu Leu Lys Ile Asp Glu Gly Gly Val Glu Lys Tyr Lys Thr
            100                 105                 110

Gln Tyr Ile Asp Lys Ile Ala Ala Ile Ile Lys Lys Tyr Pro Asp Val
        115                 120                 125

Lys Ile Asn Leu Ala Ile Glu Pro Asp Ser Leu Ala Asn Met Val Thr
130                 135                 140

Asn Met Gly Val Gln Lys Cys Ser Arg Ala Ala Pro Tyr Tyr Lys Glu
145                 150                 155                 160

Leu Thr Ala Tyr Ala Leu Lys Thr Leu Asn Phe Asn Asn Val Asp Met
                165                 170                 175

Tyr Met Asp Gly Gly His Ala Gly Trp Leu Gly Trp Asp Ala Asn Ile
            180                 185                 190

Gly Pro Thr Ala Lys Leu Phe Ala Glu Val Tyr Lys Ala Ala Gly Ser
        195                 200                 205

Pro Arg Gly Val Arg Gly Ile Val Thr Asn Val Ser Asn Tyr Asn Ala
    210                 215                 220

Leu Arg Val Ser Ser Cys Pro Ser Ile Thr Gln Gly Asn Lys Asn Cys
225                 230                 235                 240

Asp Glu Glu Arg Tyr Ile Asn Ala Leu Ala Pro Leu Leu Lys Asn Glu
                245                 250                 255

Gly Phe Pro Ala His Phe Ile Val Asp Gln Gly Arg Ser Gly Lys Val
            260                 265                 270

Pro Thr Asn Gln Gln Glu Trp Gly Asp Trp Cys Asn Val Ser Gly Ala
        275                 280                 285

Gly Phe Gly Thr Arg Pro Thr Thr Asn Thr Gly Asn Ala Leu Ile Asp
    290                 295                 300

Ala Ile Val Trp Val Lys Pro Gly Gly Glu Ser Asp Gly Thr Ser Asp
305                 310                 315                 320

Thr Ser Ala Ala Arg Tyr Asp Ala His Cys Gly Arg Asn Ser Ala Phe
                325                 330                 335

Lys Pro Ala Pro Glu Ala Gly Thr Trp Phe Gln Ala Tyr Phe Glu Met
            340                 345                 350

Leu Leu Lys Asn Ala Asn Pro Ala Leu Ala

<210> SEQ ID NO 25
<211> LENGTH: 351
<212> TYPE: PRT
<213> ORGANISM: Agaricus bisporus D649

<400> SEQUENCE: 25

Ala Gly Asn Pro Tyr Thr Gly Lys Thr Val Trp Leu Ser Pro Phe Tyr
1               5                   10                  15

Ala Asp Glu Val Ala Gln Ala Ala Asp Ile Ser Asn Pro Ser Leu
            20                  25                  30

Ala Thr Lys Ala Ala Ser Val Ala Lys Ile Pro Thr Phe Val Trp Phe
        35                  40                  45

Asp Thr Val Ala Lys Val Pro Asp Leu Gly Gly Tyr Leu Ala Asp Ala
50                  55                  60

Arg Ser Lys Asn Gln Leu Val Gln Ile Val Tyr Asp Leu Pro Asp
65                  70                  75                  80

Arg Asp Cys Ala Ala Leu Ala Ser Asn Gly Glu Phe Ser Leu Ala Asn
                85                  90                  95

Asp Gly Leu Asn Lys Tyr Lys Asn Tyr Val Asp Gln Ile Ala Ala Gln
            100                 105                 110

Ile Lys Gln Phe Pro Asp Val Ser Val Val Ala Val Ile Glu Pro Asp
        115                 120                 125

Ser Leu Ala Asn Leu Val Thr Asn Leu Asn Val Gln Lys Cys Ala Asn
130                 135                 140

Ala Gln Ser Ala Tyr Lys Glu Gly Val Ile Tyr Ala Val Gln Lys Leu
145                 150                 155                 160

Asn Ala Val Gly Val Thr Met Tyr Ile Asp Ala Gly His Ala Gly Trp
                165                 170                 175

Leu Gly Trp Pro Ala Asn Leu Ser Pro Ala Gln Leu Phe Ala Gln
            180                 185                 190

Ile Tyr Arg Asp Ala Gly Ser Pro Arg Asn Leu Arg Gly Ile Ala Thr
        195                 200                 205

Asn Val Ala Asn Phe Asn Ala Leu Arg Ala Ser Ser Pro Asp Pro Ile
210                 215                 220

Thr Gln Gly Asn Ser Asn Tyr Asp Glu Ile His Tyr Ile Glu Ala Leu
225                 230                 235                 240

Ala Pro Met Leu Ser Asn Ala Gly Phe Pro Ala His Phe Ile Val Asp
                245                 250                 255

Gln Gly Arg Ser Gly Val Gln Asn Ile Arg Asp Gln Trp Gly Asp Trp
            260                 265                 270

Cys Asn Val Lys Gly Ala Gly Phe Gly Gln Arg Pro Thr Thr Asn Thr
        275                 280                 285

Gly Ser Ser Leu Ile Asp Ala Ile Val Trp Val Lys Pro Gly Gly Glu
290                 295                 300

Cys Asp Gly Thr Ser Asp Asn Ser Ser Pro Arg Phe Asp Ser His Cys
305                 310                 315                 320

Ser Leu Ser Asp Ala His Gln Pro Ala Pro Glu Ala Gly Thr Trp Phe
                325                 330                 335

Gln Ala Tyr Phe Glu Thr Leu Val Ala Asn Ala Asn Pro Ala Leu
            340                 345                 350

<210> SEQ ID NO 26
<211> LENGTH: 360
<212> TYPE: PRT

<213> ORGANISM: Polyporus arcularius 69B-8

<400> SEQUENCE: 26

```
Thr Pro Ala Ala Gly Asn Pro Phe Val Gly Val Thr Pro Phe Leu Ser
1               5                   10                  15

Pro Tyr Tyr Ala Ala Glu Val Ala Ala Ala Asp Ala Ile Thr Asp
            20                  25                  30

Ser Thr Leu Lys Ala Lys Ala Ala Ser Val Ala Lys Ile Pro Thr Phe
            35                  40                  45

Thr Trp Leu Asp Ser Val Ala Lys Val Pro Asp Leu Gly Thr Tyr Leu
50                  55                  60

Ala Asp Ala Ser Ala Leu Gln Lys Ser Ser Gly Gln Pro Gln Val Val
65                  70                  75                  80

Gln Ile Val Val Tyr Asp Leu Pro Asp Arg Asp Cys Ala Ala Lys Ala
                85                  90                  95

Ser Asn Gly Glu Phe Ser Ile Ala Asp Gly Gly Gln Ala Lys Tyr Tyr
            100                 105                 110

Asp Tyr Ile Asp Gln Ile Val Ala Gln Ile Lys Lys Phe Pro Asp Val
            115                 120                 125

Arg Val Ile Ala Val Ile Glu Pro Asp Ser Leu Ala Asn Leu Val Thr
130                 135                 140

Asn Leu Asn Val Gln Lys Cys Ala Asn Ala Gln Thr Thr Tyr Lys Ala
145                 150                 155                 160

Cys Val Thr Tyr Ala Leu Asn Gln Leu Ala Ser Val Gly Val Tyr Gln
                165                 170                 175

Tyr Met Asp Ala Gly His Ala Gly Trp Leu Gly Trp Pro Ala Asn Ile
            180                 185                 190

Gln Pro Ala Ala Gln Leu Phe Ala Asp Met Phe Lys Ser Ala Asn Ser
            195                 200                 205

Ser Lys Phe Val Arg Gly Leu Ala Thr Asn Val Ala Asn Tyr Asn Ala
210                 215                 220

Leu Ser Ala Ala Ser Pro Asp Pro Ile Thr Gln Gly Asp Pro Asn Tyr
225                 230                 235                 240

Asp Glu Leu His Tyr Ile Asn Ala Leu Gly Pro Met Leu Ala Gln Gln
                245                 250                 255

Gly Phe Pro Ala Gln Phe Val Val Asp Gln Gly Arg Ser Gly Gln Gln
            260                 265                 270

Asn Leu Arg Gln Gln Trp Gly Asp Trp Cys Asn Ile Lys Gly Ala Gly
            275                 280                 285

Phe Gly Thr Arg Pro Thr Thr Asn Thr Gly Ser Ser Leu Ile Asp Ala
290                 295                 300

Ile Val Trp Val Lys Pro Gly Gly Glu Ser Asp Gly Thr Ser Asn Ser
305                 310                 315                 320

Ser Ser Pro Arg Phe Asp Ser Thr Cys Ser Leu Ser Asp Ala Thr Gln
                325                 330                 335

Pro Ala Pro Glu Ala Gly Thr Trp Phe Gln Thr Tyr Phe Glu Thr Leu
            340                 345                 350

Val Ser Lys Ala Asn Pro Pro Leu
355                 360
```

<210> SEQ ID NO 27
<211> LENGTH: 358
<212> TYPE: PRT
<213> ORGANISM: Lentinula edodes Stamets CS-2

<400> SEQUENCE: 27

Thr Pro Ala Ala Gly Asn Pro Phe Thr Gly Tyr Glu Ile Tyr Leu Ser
1               5                   10                  15

Pro Tyr Tyr Ala Asn Glu Ile Ala Ala Ala Val Thr Gln Ile Ser Asp
            20                  25                  30

Pro Thr Thr Ala Ala Ala Ala Lys Val Ala Asn Ile Pro Thr Phe
            35                  40                  45

Ile Trp Leu Asp Gln Val Ala Lys Val Pro Asp Leu Gly Thr Tyr Leu
50                  55                  60

Ala Asp Ala Ser Ala Lys Gln Lys Ser Glu Gly Lys Asn Tyr Leu Val
65                  70                  75                  80

Gln Ile Val Val Tyr Asp Leu Pro Asp Arg Asp Cys Ala Ala Leu Ala
                85                  90                  95

Ser Asn Gly Glu Phe Thr Ile Ala Asp Asn Gly Glu Ala Asn Tyr His
            100                 105                 110

Asp Tyr Ile Asp Gln Ile Val Ala Gln Ile Lys Gln Tyr Pro Asp Val
            115                 120                 125

His Val Val Ala Val Ile Glu Pro Asp Ser Leu Ala Asn Leu Val Thr
            130                 135                 140

Asn Leu Ser Val Ala Lys Cys Ala Asn Ala Gln Thr Thr Tyr Leu Glu
145                 150                 155                 160

Cys Val Thr Tyr Ala Met Gln Gln Leu Ser Ala Val Gly Val Thr Met
                165                 170                 175

Tyr Leu Asp Ala Gly His Ala Gly Trp Leu Gly Trp Pro Ala Asn Leu
            180                 185                 190

Ser Pro Ala Ala Gln Leu Phe Thr Ser Leu Tyr Ser Asn Ala Gly Ser
            195                 200                 205

Pro Ser Gly Val Arg Gly Leu Ala Thr Asn Val Ala Asn Tyr Asn Ala
            210                 215                 220

Leu Val Ala Thr Thr Pro Asp Pro Ile Thr Gln Gly Asp Pro Asn Tyr
225                 230                 235                 240

Asp Glu Met Leu Tyr Ile Glu Ala Leu Ala Pro Leu Leu Gly Ser Phe
                245                 250                 255

Pro Ala His Phe Ile Val Asp Gln Gly Arg Ser Gly Val Gln Asp Ile
            260                 265                 270

Arg Gln Gln Trp Gly Asp Trp Cys Asn Val Leu Gly Ala Gly Phe Gly
            275                 280                 285

Thr Gln Pro Thr Thr Asn Thr Gly Ser Ser Leu Ile Asp Ser Ile Val
            290                 295                 300

Trp Val Lys Pro Gly Gly Glu Cys Asp Gly Thr Ser Asn Thr Ser Ser
305                 310                 315                 320

Pro Arg Tyr Asp Ala His Cys Gly Leu Pro Asp Ala Thr Pro Asn Ala
                325                 330                 335

Pro Glu Ala Gly Thr Trp Phe Gln Ala Tyr Phe Glu Thr Leu Val Glu
            340                 345                 350

Lys Ala Asn Pro Pro Leu
            355

<210> SEQ ID NO 28
<211> LENGTH: 357
<212> TYPE: PRT
<213> ORGANISM: Lentinula edodes L54

<400> SEQUENCE: 28

Thr Pro Ala Ala Gly Asn Pro Phe Thr Glu Gln Ile Tyr Leu Ser Pro
1               5                   10                  15

Tyr Tyr Ala Asn Glu Ile Ala Ala Val Thr Gln Ile Ser Asp Pro
            20                  25                  30

Thr Thr Ala Ala Ala Ala Lys Val Ala Asn Ile Pro Thr Phe Ile
        35                  40                  45

Trp Leu Asp Gln Val Ala Lys Val Pro Asp Leu Gly Thr Tyr Leu Ala
50                  55                  60

Asp Ala Ser Ala Lys Gln Lys Ser Glu Gly Lys Asn Tyr Leu Val Gln
65                  70                  75                  80

Ile Val Val Tyr Asp Leu Pro Asp Arg Asp Cys Ala Ala Leu Ala Ser
                85                  90                  95

Asn Gly Glu Phe Thr Ile Ala Asp Asn Gly Glu Ala Asn Tyr His Asp
            100                 105                 110

Tyr Ile Asp Gln Ile Val Ala Gln Ile Lys Gln Tyr Pro Asp Val His
        115                 120                 125

Val Val Ala Val Ile Glu Pro Asp Ser Leu Ala Asn Leu Val Thr Asn
130                 135                 140

Leu Ser Val Ala Lys Cys Ala Asn Ala Gln Thr Thr Tyr Leu Glu Cys
145                 150                 155                 160

Val Thr Tyr Ala Met Gln Gln Leu Ser Ala Val Gly Val Thr Met Tyr
                165                 170                 175

Leu Asp Ala Gly His Ala Gly Trp Leu Gly Trp Pro Ala Asn Leu Ser
            180                 185                 190

Pro Ala Ala Gln Leu Phe Thr Ser Leu Tyr Ser Asn Ala Gly Ser Pro
        195                 200                 205

Ser Gly Val Arg Gly Leu Ala Thr Asn Val Ala Asn Tyr Asn Ala Leu
210                 215                 220

Val Ala Thr Thr Pro Asp Pro Ile Thr Gln Gly Asp Pro Asn Tyr Asp
225                 230                 235                 240

Glu Met Leu Tyr Ile Glu Ala Leu Ala Pro Leu Leu Gly Ser Phe Pro
                245                 250                 255

Ala His Phe Ile Val Asp Gln Gly Arg Ser Gly Val Gln Asp Ile Arg
            260                 265                 270

Gln Gln Trp Gly Asp Trp Cys Asn Val Leu Gly Ala Gly Phe Gly Thr
        275                 280                 285

Gln Pro Thr Thr Asn Thr Gly Ser Ser Leu Ile Asp Ser Ile Val Trp
290                 295                 300

Val Lys Pro Gly Gly Glu Cys Asp Gly Thr Ser Asn Thr Ser Ser Pro
305                 310                 315                 320

Arg Tyr Asp Ala His Cys Gly Leu Pro Asp Ala Thr Pro Asn Ala Pro
                325                 330                 335

Glu Ala Gly Thr Trp Phe Gln Ala Tyr Phe Glu Thr Leu Val Glu Lys
            340                 345                 350

Ala Asn Pro Pro Leu
        355

<210> SEQ ID NO 29
<211> LENGTH: 365
<212> TYPE: PRT
<213> ORGANISM: Malbranchea cinnamomea

<400> SEQUENCE: 29

Gln Ala Asn Ser Ser Asn Pro Phe Ala Gly His Thr Ile Tyr Pro Asn
1               5                   10                  15

Pro Tyr Tyr Ser Asn Glu Ile Asp Glu Phe Ala Ile Pro Ala Leu Gln
            20                  25                  30

Glu Thr Asp Pro Ala Leu Val Glu Lys Ala Leu Val Lys Glu Val
            35                  40                  45

Gly Thr Phe Phe Trp Ile Asp Val Ala Lys Val Pro Asp Ile Gly
 50                  55                  60

Pro Tyr Leu Gln Gly Ile Gln Glu Ala Asn Ala Gly Gln Asn Pro
 65                  70                  75                  80

Pro Tyr Ile Gly Ala Ile Val Val Tyr Asp Leu Pro Asn Arg Asp Cys
                 85                  90                  95

Ala Ala Ala Ala Ser Asn Gly Glu Phe Ser Leu Glu Asp Gly Gly Glu
                100                 105                 110

Glu Lys Tyr Arg Gly Tyr Ile Asp Gly Ile Arg Glu Gln Ile Glu Lys
            115                 120                 125

Tyr Pro Asp Val Arg Val Ala Leu Val Ile Glu Pro Asp Ser Leu Ala
        130                 135                 140

Asn Met Val Thr Asn Leu Asn Val Pro Lys Cys Ala Glu Ser Glu Gln
145                 150                 155                 160

Ala Tyr Arg Asp Gly Val Ala Tyr Ala Leu Lys Gln Leu Asp Leu Pro
                165                 170                 175

Asn Val Trp Thr Tyr Ile Asp Ala Gly His Ser Gly Trp Leu Gly Trp
            180                 185                 190

Pro Ala Asn Ile Glu Pro Ala Ala Glu Ile Phe Val Glu Val Trp Asn
        195                 200                 205

Ala Ala Gly Arg Pro Lys Ser Thr Arg Gly Phe Ala Thr Asn Val Ser
210                 215                 220

Asn Tyr Asn Gly Tyr Ser Leu Ser Thr Ala Pro Pro Tyr Thr Glu Pro
225                 230                 235                 240

Asn Pro Asn Phe Asp Glu Val Arg Tyr Ile Asn Ala Phe Arg Pro Leu
                245                 250                 255

Leu Glu Ala Arg Gly Phe Pro Ala Tyr Phe Ile Val Asp Gln Gly Arg
            260                 265                 270

Ser Gly Val Gln Pro Thr Ala Gln Ile Glu Gln Gly His Trp Cys Asn
        275                 280                 285

Val Ile Asp Thr Gly Phe Gly Thr Arg Pro Thr Thr Asp Thr Gly Asn
290                 295                 300

Glu Tyr Val Asp Ser Ile Val Trp Val Lys Pro Gly Gly Glu Ser Asp
305                 310                 315                 320

Gly Thr Ser Asp Thr Ser Ala Glu Arg Tyr Asp Tyr His Cys Gly Leu
                325                 330                 335

Glu Asp Ala Leu Lys Pro Ala Pro Glu Ala Gly Gln Trp Phe Gln Ala
            340                 345                 350

Tyr Phe Glu Gln Leu Leu Arg Asn Ala Asn Pro Pro Phe
        355                 360                 365

<210> SEQ ID NO 30
<211> LENGTH: 440
<212> TYPE: PRT
<213> ORGANISM: Phanerochaete chrysosporium

<400> SEQUENCE: 30

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Thr Ser Val Ile Thr
        35                  40                  45

```
Ser His Ser Ser Ser Val Ser Val Ser Ser His Ser Gly Ser Ser
     50                  55                  60

Thr Ser Thr Ser Ser Pro Thr Gly Pro Thr Gly Thr Asn Pro Pro
 65                  70                  75                  80

Pro Pro Ser Ala Asn Asn Pro Trp Thr Gly Phe Gln Ile Phe Leu Ser
                 85                  90                  95

Pro Tyr Tyr Ala Asn Glu Val Ala Ala Ala Lys Gln Ile Thr Asp
                100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
                180                 185                 190

Asn Tyr Ile Asp Gln Ile Val Ala Gln Ile Gln Gln Phe Pro Asp Val
            195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
        290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
        370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Leu
        435                 440

<210> SEQ ID NO 31
<211> LENGTH: 360
<212> TYPE: PRT
```

<213> ORGANISM: Volvariella volvacea

<400> SEQUENCE: 31

Val Pro Ala Ala Gly Asn Pro Tyr Thr Gly Tyr Glu Ile Tyr Leu Ser
1               5                   10                  15

Pro Tyr Tyr Ala Ala Glu Ala Gln Ala Ala Ala Gln Ile Ser Asp
                20                  25                  30

Ala Thr Gln Lys Ala Lys Ala Leu Lys Val Ala Gln Ile Pro Thr Phe
            35                  40                  45

Thr Trp Phe Asp Val Ile Ala Lys Thr Ser Thr Leu Gly Asp Tyr Leu
    50                  55                  60

Ala Glu Ala Ser Ala Leu Gly Lys Ser Ser Gly Lys Lys Tyr Leu Val
65                  70                  75                  80

Gln Ile Val Val Tyr Asp Leu Pro Asp Arg Asp Cys Ala Ala Leu Ala
                85                  90                  95

Ser Asn Gly Glu Phe Ser Ile Ala Asn Asn Gly Leu Asn Asn Tyr Lys
            100                 105                 110

Gly Tyr Ile Asp Gln Leu Val Ala Gln Ile Lys Lys Tyr Pro Asp Val
        115                 120                 125

Arg Val Val Ala Val Ile Glu Pro Asp Ser Leu Ala Asn Leu Val Thr
130                 135                 140

Asn Leu Asn Val Ser Lys Cys Ala Asn Ala Gln Thr Ala Tyr Lys Ala
145                 150                 155                 160

Gly Val Thr Tyr Ala Leu Gln Gln Leu Asn Ser Val Gly Val Tyr Met
                165                 170                 175

Tyr Leu Asp Ala Gly His Ala Gly Trp Leu Gly Trp Pro Ala Asn Leu
            180                 185                 190

Asn Pro Ala Ala Gln Leu Phe Ser Gln Leu Tyr Arg Asp Ala Gly Ser
        195                 200                 205

Pro Gln Tyr Val Arg Gly Leu Ala Thr Asn Val Ala Asn Tyr Asn Ala
210                 215                 220

Leu Ser Ala Ser Ser Pro Asp Pro Val Thr Gln Gly Asn Pro Asn Tyr
225                 230                 235                 240

Asp Glu Leu His Tyr Ile Asn Ala Leu Ala Pro Ala Leu Gln Ser Gly
                245                 250                 255

Gly Phe Pro Ala His Phe Ile Val Asp Gln Gly Arg Ser Gly Val Gln
            260                 265                 270

Asn Ile Arg Gln Gln Trp Gly Asp Trp Cys Asn Val Lys Gly Ala Gly
        275                 280                 285

Phe Gly Gln Arg Pro Thr Leu Ser Thr Gly Ser Ser Leu Ile Asp Ala
290                 295                 300

Ile Val Trp Ile Lys Pro Gly Gly Glu Cys Asp Gly Thr Thr Asn Thr
305                 310                 315                 320

Ser Ser Pro Arg Tyr Asp Ser His Cys Gly Leu Ser Asp Ala Thr Pro
                325                 330                 335

Asn Ala Pro Glu Ala Gly Gln Trp Phe Gln Ala Tyr Phe Glu Thr Leu
            340                 345                 350

Val Arg Asn Ala Ser Pro Pro Leu
        355                 360

<210> SEQ ID NO 32
<211> LENGTH: 356
<212> TYPE: PRT
<213> ORGANISM: Chrysosporium l

```
Leu Asp Ala Ser Thr Asn Val Phe Gln Gln Tyr Thr Leu His Pro Asn
1               5                   10                  15

Asn Phe Tyr Arg Ala Glu Val Glu Ala Ala Glu Ala Ile Ser Asp
            20                  25                  30

Ser Ala Leu Ala Glu Lys Ala Arg Lys Val Ala Asp Val Gly Thr Phe
        35                  40                  45

Leu Trp Leu Asp Thr Ile Glu Asn Ile Gly Arg Leu Glu Pro Ala Leu
50                  55                  60

Glu Asp Val Pro Cys Glu Asn Ile Val Gly Leu Val Ile Tyr Asp Leu
65                  70                  75                  80

Pro Gly Arg Asp Cys Ala Ala Lys Ala Ser Asn Gly Glu Leu Lys Val
                85                  90                  95

Gly Glu Leu Asp Arg Tyr Lys Thr Glu Tyr Ile Asp Lys Ile Ala Glu
            100                 105                 110

Ile Leu Lys Ala His Ser Asn Thr Ala Phe Ala Leu Val Ile Glu Pro
        115                 120                 125

Asp Ser Leu Pro Asn Leu Val Thr Asn Ser Asp Leu Gln Thr Cys Gln
    130                 135                 140

Gln Ser Ala Ser Gly Tyr Arg Glu Gly Val Ala Tyr Ala Leu Lys Gln
145                 150                 155                 160

Leu Asn Leu Pro Asn Val Val Met Tyr Ile Asp Ala Gly His Gly Gly
                165                 170                 175

Trp Leu Gly Trp Asp Ala Asn Leu Lys Pro Gly Ala Gln Glu Leu Ala
            180                 185                 190

Ser Val Tyr Lys Ser Ala Gly Ser Pro Ser Gln Val Arg Gly Ile Ser
        195                 200                 205

Thr Asn Val Ala Gly Trp Asn Ala Trp Asp Gln Glu Pro Gly Glu Phe
210                 215                 220

Ser Asp Ala Ser Asp Ala Gln Tyr Asn Lys Cys Gln Asn Glu Lys Ile
225                 230                 235                 240

Tyr Ile Asn Thr Phe Gly Ala Glu Leu Lys Ser Ala Gly Met Pro Asn
                245                 250                 255

His Ala Ile Ile Asp Thr Gly Arg Asn Gly Val Thr Gly Leu Arg Asp
            260                 265                 270

Glu Trp Gly Asp Trp Cys Asn Val Asn Gly Ala Gly Phe Gly Val Arg
        275                 280                 285

Pro Thr Ala Asn Thr Gly Asp Glu Leu Ala Asp Ala Phe Val Trp Val
    290                 295                 300

Lys Pro Gly Gly Glu Ser Asp Gly Thr Ser Asp Ser Ser Ala Ala Arg
305                 310                 315                 320

Tyr Asp Ser Phe Cys Gly Lys Pro Asp Ala Phe Lys Pro Ser Pro Glu
                325                 330                 335

Ala Gly Thr Trp Asn Gln Ala Tyr Phe Glu Met Leu Leu Lys Asn Ala
            340                 345                 350

Asn Pro Ser Phe
        355

<210> SEQ ID NO 33
<211> LENGTH: 409
<212> TYPE: PRT
<213> ORGANISM: Pleurotus sajor-caju

<400> SEQUENCE: 33

Thr Pro Asp Ala Gly Asn Pro Tyr Ile Gly Tyr Asp Val Ser His Val
1               5                   10                  15
```

Leu Trp Cys Gln Ile Tyr Leu Ser Pro Tyr Tyr Ala Asp Glu Val Ala
            20                  25                  30

Ala Ala Val Ser Ala Ile Ser Asn Pro Ala Leu Ala Ala Lys Ala Ala
        35                  40                  45

Ser Val Ala Asn Ile Pro Thr Phe Ile Trp Phe Asp Val Val Ala Lys
    50                  55                  60

Val Pro Thr Leu Gly Thr Tyr Leu Ala Asp Ala Leu Ser Ile Gln Gln
65                  70                  75                  80

Ser Thr Gly Arg Asn Gln Leu Val Gln Ile Val Val Tyr Asp Leu Pro
                85                  90                  95

Asp Arg Asp Cys Ala Ala Leu Ala Ser Asn Gly Glu Phe Ser Ile Ala
            100                 105                 110

Asn Asn Gly Leu Ala Asn Tyr Lys Asn Tyr Val Asp Gln Ile Val Ala
        115                 120                 125

Gln Ile Ala Arg Thr Cys Cys Pro Leu Val Thr Ser Ala Ile Thr Asp
130                 135                 140

Leu Ala Cys Leu Ser Glu Tyr Pro Gln Ile Arg Val Val Ala Val Val
145                 150                 155                 160

Glu Pro Asp Ser Leu Ala Asn Met Val Thr Asn Leu Asn Val Pro Lys
                165                 170                 175

Cys Ala Gly Ala Gln Ala Ala Tyr Thr Glu Gly Val Thr Tyr Ala Leu
            180                 185                 190

Gln Lys Leu Asn Thr Val Gly Val Tyr Ser Tyr Val Asp Ala Gly His
        195                 200                 205

Ala Gly Trp Leu Gly Trp Pro Ala Asn Leu Gly Pro Ala Ala Gln Leu
210                 215                 220

Phe Ala Asn Leu Tyr Thr Asn Ala Gly Ser Pro Ser Phe Phe Arg Gly
225                 230                 235                 240

Leu Ala Thr Asn Val Ala Asn Tyr Asn Leu Leu Asn Ala Pro Ser Pro
                245                 250                 255

Asp Pro Val Thr Ser Pro Asn Ala Asn Tyr Asp Glu Ile His Tyr Ile
            260                 265                 270

Asn Val Ser Asp Cys Phe Val Leu Ile Trp Thr Ser Leu Thr Ile Cys
        275                 280                 285

Ile Ile Ala Leu Ala Pro Glu Leu Ser Ser Arg Gly Phe Pro Ala His
290                 295                 300

Phe Ile Val Asp Gln Gly Arg Ser Ala Val Gln Gly Ile Arg Gly Ala
305                 310                 315                 320

Trp Gly Asp Trp Cys Asn Val Asp Asn Ala Gly Phe Gly Thr Arg Pro
                325                 330                 335

Thr Thr Ser Thr Gly Ser Ser Leu Ile Asp Ala Ile Val Trp Val Lys
            340                 345                 350

Pro Gly Gly Glu Ser Asp Gly Thr Ser Asp Thr Ser Ala Val Arg Tyr
        355                 360                 365

Asp Gly His Cys Gly Leu Ala Ser Ala Lys Lys Pro Ala Pro Glu Ala
370                 375                 380

Met Ala Ser Val Tyr Ser His Ser Ser Phe Gln Ala Tyr Phe Glu Met
385                 390                 395                 400

Leu Val Ala Asn Ala Val Pro Ala Leu
                405

<210> SEQ ID NO 34
<211> LENGTH: 359
<212> TYPE: PRT

<213> ORGANISM: Trametes versicolor

<400> SEQUENCE: 34

| | | | | | | | | | | | | | | |
|---|---|---|---|---|---|---|---|---|---|---|---|---|---|---|
| Thr | Pro | Ala | Ala | Gly | Asn | Pro | Phe | Thr | Gly | Phe | Gln | Val | Tyr | Leu | Ser |
| 1 | | | | 5 | | | | | 10 | | | | | 15 | |
| Pro | Tyr | Tyr | Ser | Ala | Glu | Ile | Ala | Ser | Ala | Ala | Ala | Val | Thr | Asp | |
| | | | 20 | | | | | 25 | | | | | 30 | | |
| Ser | Ser | Leu | Lys | Ala | Lys | Ala | Ala | Ser | Val | Ala | Asn | Ile | Pro | Thr | Phe |
| | | 35 | | | | | 40 | | | | | 45 | | | |
| Thr | Trp | Leu | Asp | Ser | Val | Ala | Lys | Val | Pro | Asp | Leu | Gly | Thr | Tyr | Leu |
| | 50 | | | | | 55 | | | | | 60 | | | | |
| Ala | Asp | Ala | Ser | Ser | Ile | Gln | Thr | Lys | Thr | Gly | Gln | Lys | Gln | Leu | Val |
| 65 | | | | | 70 | | | | | 75 | | | | | 80 |
| Pro | Ile | Val | Val | Tyr | Glu | Leu | Pro | Asp | Arg | Asp | Cys | Ala | Ala | Lys | Ala |
| | | | | 85 | | | | | 90 | | | | | 95 | |
| Ser | Asn | Gly | Glu | Phe | Ser | Ile | Ala | Asp | Ala | Gly | Ala | Glu | Asn | Tyr | Lys |
| | | | 100 | | | | | 105 | | | | | 110 | | |
| Asp | Tyr | Ile | Asp | Gln | Ile | Val | Pro | Gln | Ile | Lys | Gln | Phe | Pro | Asp | Val |
| | | 115 | | | | | 120 | | | | | 125 | | | |
| Arg | Val | Val | Ala | Val | Ile | Glu | Pro | Asp | Ser | Leu | Ala | Asn | Leu | Val | Thr |
| | 130 | | | | | 135 | | | | | 140 | | | | |
| Asn | Leu | Asn | Val | Gln | Lys | Cys | Ala | Asn | Gly | Gly | Thr | Tyr | Lys | Ala | Ser |
| 145 | | | | | 150 | | | | | 155 | | | | | 160 |
| Val | Thr | Tyr | Ala | Leu | Gln | Gln | Leu | Ser | Ser | Val | Gly | Val | Thr | Met | Tyr |
| | | | | 165 | | | | | 170 | | | | | 175 | |
| Met | Asp | Ala | Gly | His | Ala | Gly | Trp | Leu | Gly | Trp | Pro | Ala | Asn | Ile | Gln |
| | | | 180 | | | | | 185 | | | | | 190 | | |
| Pro | Gly | Ser | Glu | Val | Phe | Ala | Glu | Met | Phe | Lys | Ser | Ala | Asp | Phe | Val |
| | | 195 | | | | | 200 | | | | | 205 | | | |
| Ala | Phe | Val | Arg | Ala | Phe | Ala | Thr | Asn | Val | Arg | Glu | Tyr | Asn | Ala | Leu |
| | 210 | | | | | 215 | | | | | 220 | | | | |
| Thr | Ala | Ala | Phe | Pro | Arg | Pro | Ile | Thr | Gln | Gly | Asn | Pro | Asn | Tyr | Asp |
| 225 | | | | | 230 | | | | | 235 | | | | | 240 |
| Glu | Phe | Pro | Tyr | Ile | Gln | Arg | Val | Arg | Pro | Met | Leu | Lys | Ser | Pro | Gly |
| | | | | 245 | | | | | 250 | | | | | 255 | |
| Phe | Pro | Ala | Gln | Phe | Val | Val | Asp | Gln | Gly | Arg | Ala | Gly | Gln | Gln | Asn |
| | | | 260 | | | | | 265 | | | | | 270 | | |
| Phe | Arg | Gln | Gln | Trp | Gly | Asp | Trp | Cys | Asn | Ile | Lys | Gly | Ala | Gly | Phe |
| | | 275 | | | | | 280 | | | | | 285 | | | |
| Gly | Thr | Arg | Pro | Thr | Thr | Ser | Thr | Gly | Asn | Pro | Leu | Ile | Asp | Ala | Ile |
| | 290 | | | | | 295 | | | | | 300 | | | | |
| Ile | Trp | Val | Lys | Pro | Gly | Gly | Glu | Ser | Asp | Gly | Thr | Ser | Asn | Ser | Ser |
| 305 | | | | | 310 | | | | | 315 | | | | | 320 |
| Ser | Pro | Arg | Tyr | Asp | Ser | Thr | Leu | Leu | Ser | Val | Arg | Arg | Asp | Pro | |
| | | | | 325 | | | | | 330 | | | | | 335 | |
| Ala | Pro | Glu | Ala | Gly | Thr | Trp | Phe | Gln | Ala | Tyr | Phe | Glu | Thr | Leu | Val |
| | | | 340 | | | | | 345 | | | | | 350 | | |
| Ser | Lys | Pro | Thr | Arg | Pro | Leu | | | | | | | | | |
| | | | | 355 | | | | | | | | | | | |

<210> SEQ ID NO 35
<211> LENGTH: 356
<212> TYPE: PRT
<213> ORGANISM: Neurospora crassa OR74A

<400> SEQUENCE: 35

Leu Asp Ala Ser Thr Asn Val Trp Lys Lys Tyr Thr Leu His Ala Asn
1               5                   10                  15

Lys Phe Tyr Arg Thr Glu Val Glu Ala Ala Val Ala Ala Ile Ser Asp
            20                  25                  30

Ser Ser Leu Ala Ala Lys Ala Ala Lys Val Ala Asn Val Gly Ser Phe
        35                  40                  45

Leu Trp Leu Asp Ser Ile Glu Asn Ile Gly Lys Leu Glu Pro Ala Leu
50                  55                  60

Glu Asp Val Pro Cys Asp His Ile Leu Gly Leu Val Ile Tyr Asp Leu
65                  70                  75                  80

Pro Gly Arg Asp Cys Ala Ala Lys Ala Ser Asn Gly Glu Leu Ala Val
                85                  90                  95

Gly Glu Leu Ser Arg Tyr Lys Thr Glu Tyr Ile Asp Ala Ile Val Lys
            100                 105                 110

Ile Leu Lys Ala His Pro Lys Thr Ala Phe Ala Leu Val Ile Glu Pro
        115                 120                 125

Asp Ser Leu Pro Asn Leu Val Thr Asn Ser Asp Leu Gln Thr Cys Lys
130                 135                 140

Asp Ser Ala Ser Gly Tyr Arg Asp Gly Val Ala Tyr Ala Leu Arg Asn
145                 150                 155                 160

Leu Asn Leu Pro Asn Val Val Met Tyr Ile Asp Ala Gly His Gly Gly
                165                 170                 175

Trp Leu Gly Trp Asp Ala Asn Leu Lys Pro Gly Ala Gln Glu Leu Ala
            180                 185                 190

Lys Ala Tyr Lys Ala Ala Gly Ser Pro Lys Gln Val Arg Gly Ile Ala
        195                 200                 205

Thr Asn Val Ala Gly Trp Asn Gln Trp Asp Leu Thr Pro Gly Glu Phe
210                 215                 220

Ser Lys Ala Ser Asp Ala Lys Tyr Asn Lys Cys Gln Asn Glu Lys Leu
225                 230                 235                 240

Tyr Leu Asp Asn Phe Gly Pro Ala Leu Lys Ser Ala Gly Met Pro Asn
                245                 250                 255

His Ala Ile Val Asp Thr Gly Arg Asn Gly Val Ser Gly Leu Arg Gln
            260                 265                 270

Glu Trp Gly Asn Trp Cys Asn Val Asn Gly Ala Gly Phe Gly Val Arg
        275                 280                 285

Pro Thr Ser Ser Thr Gly His Asp Leu Ala Asp Ala Phe Val Trp Val
290                 295                 300

Lys Pro Gly Gly Glu Ser Asp Gly Thr Ser Asp Ser Ser Ala Thr Arg
305                 310                 315                 320

Tyr Asp Ser Phe Cys Gly Lys Ser Asp Ala Tyr Gln Pro Ser Pro Glu
                325                 330                 335

Ala Gly Ser Trp Asn Gln Asp Tyr Phe Glu Met Leu Val Lys Asn Ala
            340                 345                 350

Lys Pro Ser Phe
        355

<210> SEQ ID NO 36
<211> LENGTH: 356
<212> TYPE: PRT
<213> ORGANISM: Magnaporthe grisea 70-15

<400> SEQUENCE: 36

Leu Asp Ala Ser Thr Asn Val Phe Ser Lys Tyr Thr Leu His Pro Asn
1               5                   10                  15

Ser Phe Tyr Arg Ala Glu Val Glu Ala Ala Glu Ala Ile Ser Asp
            20                  25                  30

Ser Thr Leu Lys Ala Gln Ala Leu Lys Val Ala Asp Val Gly Ser Phe
        35                  40                  45

Leu Trp Ile Asp Thr Ile Ser Ala Ile Ser Arg Ile Glu Pro Gly Val
    50                  55                  60

Ser Asp Gln Pro Cys Asp His Ile Leu Gly Leu Val Ile Tyr Asp Leu
65                  70                  75                  80

Pro Gly Arg Asp Cys Ala Ala Lys Ala Ser Asn Gly Glu Leu Lys Val
                85                  90                  95

Gly Glu Leu Ala Lys Tyr Lys Ser Gln Tyr Ile Asp Pro Ile Ala Ala
            100                 105                 110

Leu Leu Lys Lys Tyr Asn Asn His Ala Phe Ala Leu Leu Ile Glu Pro
        115                 120                 125

Asp Ser Leu Pro Asn Leu Val Thr Asn Ser Asp Leu Ser Ala Cys Gln
130                 135                 140

Gln Ser Ala Ala Gly Tyr Arg Asp Gly Val Ala Tyr Ala Leu Lys Thr
145                 150                 155                 160

Leu Asn Leu Pro Asn Val Val Met Tyr Ile Asp Ala Gly His Gly Gly
                165                 170                 175

Trp Leu Gly Trp Asn Asp Asn Leu Lys Pro Gly Ala Glu Glu Leu Ala
            180                 185                 190

Lys Ala Tyr Lys Ala Ala Gly Ser Pro Lys Gln Phe Arg Gly Phe Ala
        195                 200                 205

Thr Asn Val Ala Gly Trp Asn Ala Trp Asp Leu Thr Pro Gly Glu Phe
    210                 215                 220

Ser Ser Ala Ser Asp Ala Gln Trp Asn Lys Cys Gln Asn Glu Lys Ile
225                 230                 235                 240

Tyr Val Glu Thr Phe Gly Pro Leu Leu Lys Asn Ala Gly Met Pro Asn
                245                 250                 255

His Ala Ile Val Asp Val Gly Arg Asn Ala Val Gln Gly Leu Arg Glu
            260                 265                 270

Glu Trp Gly His Trp Cys Asn Val Asn Gly Ala Gly Phe Gly Val Arg
        275                 280                 285

Pro Thr Thr Ser Thr Gly Ser Ser Leu Thr Asp Ala Leu Leu Trp Val
    290                 295                 300

Lys Pro Gly Gly Glu Ser Asp Gly Thr Ser Asp Thr Ser Ala Thr Arg
305                 310                 315                 320

Tyr Asp Ser Phe Cys Gly Met Ser Asp Ala Tyr Lys Pro Ser Pro Glu
                325                 330                 335

Ala Gly Gln Trp Asn Gln Asp Tyr Phe Glu Met Leu Leu Arg Asn Ala
            340                 345                 350

Lys Pro Gln Phe
        355

<210> SEQ ID NO 37
<211> LENGTH: 447
<212> TYPE: PRT
<213> ORGANISM: Trichoderma reesei

<400> SEQUENCE: 37

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

```
Tyr Tyr Ser Gln Cys Leu Pro Gly Ala Ala Ser Ser Ser Ser Thr
        35                  40                  45

Arg Ala Ala Ser Thr Thr Ser Arg Val Ser Pro Thr Thr Ser Arg Ser
 50                      55                  60

Ser Ser Ala Thr Pro Pro Gly Ser Thr Thr Arg Val Pro Pro
 65              70                  75                  80

Val Gly Ser Gly Thr Ala Thr Tyr Ser Gly Asn Pro Phe Val Gly Val
                 85                  90                  95

Thr Pro Trp Ala Asn Ala Ala Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445
```

```
<210> SEQ ID NO 38
<211> LENGTH: 447
<212> TYPE: PRT
<213> ORGANISM: Trichoderma reesei

<400> SEQUENCE: 38

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala His Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
```

```
              385                 390                 395                 400
Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 39
<211> LENGTH: 447
<212> TYPE: PRT
<213> ORGANISM: Trichoderma reesei

<400> SEQUENCE: 39

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Lys Tyr Ala Ser Glu Val Ser Ser Leu Ala
            100                 105                 110

Ile Pro Ser Leu Thr Gly Ala Met Ala Thr Ala Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
```

```
           325                 330                 335
Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 40
<211> LENGTH: 447
<212> TYPE: PRT
<213> ORGANISM: Trichoderma reesei

<400> SEQUENCE: 40

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
```

```
                260                 265                 270
Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 41
<211> LENGTH: 447
<212> TYPE: PRT
<213> ORGANISM: Trichoderma reesei

<400> SEQUENCE: 41

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Met Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
```

-continued

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 42
<211> LENGTH: 447
<212> TYPE: PRT
<213> ORGANISM: Trichoderma reesei

<400> SEQUENCE: 42

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Pro Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu

|   |   |   |   |   | 130 |   |   |   |   | 135 |   |   |   |   | 140 |   |

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 43
<211> LENGTH: 447
<212> TYPE: PRT
<213> ORGANISM: Trichoderma reesei

<400> SEQUENCE: 43

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro

```
                65                  70                  75                  80
            Val Gly Ser Gly Thr Ala Thr Tyr Ser Gly Asn Pro Phe Val Gly Val
                                85                  90                  95
            Thr Pro Trp Ala Asn Ala Arg Tyr Ala Ser Glu Val Ser Ser Leu Ala
                            100                 105                 110
            Ile Pro Ser Leu Thr Gly Ala Met Ala Thr Ala Ala Ala Val Ala
                        115                 120                 125
            Lys Val Pro Ser Phe Met Trp Leu Asp Thr Leu Asp Lys Thr Pro Leu
            130                 135                 140
            Met Glu Gln Thr Leu Ala Asp Ile Arg Thr Ala Asn Lys Asn Gly Gly
            145                 150                 155                 160
            Asn Tyr Ala Gly Gln Phe Val Val Tyr Asp Leu Pro Asp Arg Asp Cys
                            165                 170                 175
            Ala Ala Leu Ala Ser Asn Gly Glu Tyr Ser Ile Ala Asp Gly Gly Val
                        180                 185                 190
            Ala Lys Tyr Lys Asn Tyr Ile Asp Thr Ile Arg Gln Ile Val Val Glu
                    195                 200                 205
            Tyr Ser Asp Ile Arg Thr Leu Leu Val Ile Glu Pro Asp Ser Leu Ala
            210                 215                 220
            Asn Leu Val Thr Asn Leu Gly Thr Pro Lys Cys Ala Asn Ala Gln Ser
            225                 230                 235                 240
            Ala Tyr Leu Glu Cys Ile Asn Tyr Ala Val Thr Gln Leu Asn Leu Pro
                            245                 250                 255
            Asn Val Ala Met Tyr Leu Asp Ala Gly His Ala Gly Trp Leu Gly Trp
                        260                 265                 270
            Pro Ala Asn Gln Asp Pro Ala Ala Gln Leu Phe Ala Asn Val Tyr Lys
                    275                 280                 285
            Asn Ala Ser Ser Pro Arg Ala Leu Arg Gly Leu Ala Thr Asn Val Ala
                290                 295                 300
            Asn Tyr Asn Gly Trp Asn Ile Thr Ser Pro Pro Ser Tyr Thr Gln Gly
            305                 310                 315                 320
            Asn Ala Val Tyr Asn Glu Lys Leu Tyr Ile His Ala Ile Gly Pro Leu
                            325                 330                 335
            Leu Ala Asn His Gly Trp Ser Asn Ala Phe Phe Ile Thr Asp Gln Gly
                        340                 345                 350
            Arg Ser Gly Lys Gln Pro Thr Gly Gln Gln Trp Gly Asp Trp Cys
                    355                 360                 365
            Asn Val Ile Gly Thr Gly Phe Gly Ile Arg Pro Ser Ala Asn Thr Gly
                370                 375                 380
            Asp Ser Leu Leu Asp Ser Phe Val Trp Val Lys Pro Gly Gly Glu Cys
            385                 390                 395                 400
            Asp Gly Thr Ser Asp Ser Ser Ala Pro Arg Phe Asp Pro His Cys Ala
                            405                 410                 415
            Leu Pro Asp Ala Leu Gln Pro Ala Pro Gln Ala Gly Ala Trp Phe Gln
                        420                 425                 430
            Ala Tyr Phe Val Gln Leu Leu Thr Asn Ala Asn Pro Ser Phe Leu
                    435                 440                 445

<210> SEQ ID NO 44
<211> LENGTH: 447
<212> TYPE: PRT
<213> ORGANISM: Trichoderma reesei

<400> SEQUENCE: 44

Gln Ala Cys Ser Ser Val Trp Gly Gln Cys Gly Gly Gln Asn Trp Ser
```

-continued

```
1               5                   10                  15
Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
                35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                    85                  90                  95

Thr Pro Trp Ala Asn Ala Val Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
            210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430
```

```
Ala Tyr Phe Val Gln Leu Leu Thr Asn Ala Asn Pro Ser Phe Leu
        435                 440                 445
```

<210> SEQ ID NO 45
<211> LENGTH: 447
<212> TYPE: PRT
<213> ORGANISM: Trichoderma reesei

<400> SEQUENCE: 45

```
Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Ile Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365
```

```
Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 46
<211> LENGTH: 447
<212> TYPE: PRT
<213> ORGANISM: Trichoderma reesei

<400> SEQUENCE: 46

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Val Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300
```

```
Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 47
<211> LENGTH: 447
<212> TYPE: PRT
<213> ORGANISM: Trichoderma reesei

<400> SEQUENCE: 47

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Lys Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240
```

```
Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 48
<211> LENGTH: 447
<212> TYPE: PRT
<213> ORGANISM: Trichoderma reesei

<400> SEQUENCE: 48

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175
```

Ala Ala Leu Ala Ser Asn Gly Glu Tyr Tyr Ile Ala Asp Gly Val
            180                 185                 190

Ala Lys Tyr Lys Asn Tyr Ile Asp Thr Ile Arg Gln Ile Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 49
<211> LENGTH: 447
<212> TYPE: PRT
<213> ORGANISM: Trichoderma reesei

<400> SEQUENCE: 49

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

```
Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Asp Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 50
<211> LENGTH: 447
<212> TYPE: PRT
<213> ORGANISM: Trichoderma reesei

<400> SEQUENCE: 50

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45
```

```
Arg Ala Ala Ser Thr Thr Ser Arg Val Ser Pro Thr Thr Ser Arg Ser
 50                  55                  60

Ser Ser Ala Thr Pro Pro Gly Ser Thr Thr Arg Val Pro Pro
 65                  70                  75                  80

Val Gly Ser Gly Thr Ala Thr Tyr Ser Gly Asn Pro Phe Val Gly Val
                     85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                    165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Glu Asp Trp Cys
                355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 51
<211> LENGTH: 447
<212> TYPE: PRT
<213> ORGANISM: Trichoderma reesei
```

```
<400> SEQUENCE: 51

Gln Ala Cys Ser Ser Val Trp Gly Gln Cys Gly Gly Gln Asn Trp Ser
  1               5                  10                  15
Gly Pro Thr Cys Cys Ala Ser Gly Ser Thr Cys Val Tyr Ser Asn Asp
             20                  25                  30
Tyr Tyr Ser Gln Cys Leu Pro Gly Ala Ser Ser Ser Ser Thr
         35                  40                  45
Arg Ala Ala Ser Thr Thr Ser Arg Val Ser Pro Thr Thr Ser Arg Ser
 50                  55                  60
Ser Ser Ala Thr Pro Pro Pro Gly Ser Thr Thr Thr Arg Val Pro Pro
 65                  70                  75                  80
Val Gly Ser Gly Thr Ala Thr Tyr Ser Gly Asn Pro Phe Val Gly Val
                 85                  90                  95
Thr Pro Trp Ala Asn Ala Tyr Tyr Ala Ser Glu Val Ser Ser Leu Ala
            100                 105                 110
Ile Pro Ser Leu Thr Gly Ala Met Ala Thr Ala Ala Ala Val Ala
            115                 120                 125
Lys Val Pro Ser Phe Met Trp Leu Asp Thr Leu Asp Lys Thr Pro Leu
130                 135                 140
Met Glu Gln Thr Leu Ala Asp Ile Arg Thr Ala Asn Lys Asn Gly Gly
145                 150                 155                 160
Asn Tyr Ala Gly Gln Phe Val Val Tyr Asp Leu Pro Asp Arg Asp Cys
                165                 170                 175
Ala Ala Leu Ala Ser Asn Gly Glu Tyr Ser Ile Ala Asp Gly Gly Val
            180                 185                 190
Ala Lys Tyr Lys Asn Tyr Ile Asp Thr Ile Arg Gln Ile Val Val Glu
        195                 200                 205
Tyr Ser Asp Ile Arg Thr Leu Leu Val Ile Glu Pro Asp Ser Leu Ala
210                 215                 220
Asn Leu Val Thr Asn Leu Gly Thr Pro Lys Cys Ala Asn Ala Gln Ser
225                 230                 235                 240
Ala Tyr Leu Glu Cys Ile Asn Tyr Ala Val Thr Gln Leu Asn Leu Pro
                245                 250                 255
Asn Val Ala Met Tyr Leu Asp Ala Gly His Ala Gly Trp Leu Gly Trp
            260                 265                 270
Pro Ala Asn Gln Asp Pro Ala Ala Gln Leu Phe Ala Asn Val Tyr Lys
        275                 280                 285
Asn Ala Ser Ser Pro Arg Ala Leu Arg Gly Leu Ala Thr Asn Val Ala
290                 295                 300
Asn Tyr Asn Gly Trp Asn Ile Thr Ser Pro Pro Ser Tyr Thr Gln Gly
305                 310                 315                 320
Asn Ala Val Tyr Asn Glu Lys Leu Tyr Ile His Ala Ile Gly Pro Leu
                325                 330                 335
Leu Ala Asn His Gly Trp Ser Asn Ala Phe Phe Ile Thr Asp Gln Gly
            340                 345                 350
Arg Ser Gly Lys Gln Pro Thr Gly Gln Gln Trp Gln Asp Trp Cys
        355                 360                 365
Asn Val Ile Gly Thr Gly Phe Gly Ile Arg Pro Ser Ala Asn Thr Gly
        370                 375                 380
Asp Ser Leu Leu Asp Ser Phe Val Trp Val Lys Pro Gly Gly Glu Cys
385                 390                 395                 400
Asp Gly Thr Ser Asp Ser Ser Ala Pro Arg Phe Asp Pro His Cys Ala
                405                 410                 415
```

```
Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 52
<211> LENGTH: 447
<212> TYPE: PRT
<213> ORGANISM: Trichoderma reesei

<400> SEQUENCE: 52

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350
```

```
Arg Ser Gly Lys Gln Pro Thr Gly Gln Gln Trp Ser Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 53
<211> LENGTH: 447
<212> TYPE: PRT
<213> ORGANISM: Trichoderma reesei

<400> SEQUENCE: 53

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285
```

```
Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Ala Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 54
<211> LENGTH: 447
<212> TYPE: PRT
<213> ORGANISM: Trichoderma reesei

<400> SEQUENCE: 54

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220
```

-continued

```
Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Phe Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 55
<211> LENGTH: 447
<212> TYPE: PRT
<213> ORGANISM: Trichoderma reesei

<400> SEQUENCE: 55

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160
```

```
Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Leu Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 56
<211> LENGTH: 447
<212> TYPE: PRT
<213> ORGANISM: Trichoderma reesei

<400> SEQUENCE: 56

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95
```

```
Thr Pro Trp Ala Asn Ala Tyr Tyr Ala Ser Glu Val Ser Ser Leu Ala
         100                 105                 110

Ile Pro Ser Leu Thr Gly Ala Met Ala Thr Ala Ala Ala Val Ala
    115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 57
<211> LENGTH: 447
<212> TYPE: PRT
<213> ORGANISM: Trichoderma reesei

<400> SEQUENCE: 57

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

```
Tyr Tyr Ser Gln Cys Leu Pro Gly Ala Ala Ser Ser Ser Ser Thr
        35                  40                  45

Arg Ala Ala Ser Thr Thr Ser Arg Val Ser Pro Thr Thr Ser Arg Ser
 50                  55                  60

Ser Ser Ala Thr Pro Pro Gly Ser Thr Thr Arg Val Pro Pro
 65              70                  75                  80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Ser Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445
```

-continued

```
<210> SEQ ID NO 58
<211> LENGTH: 447
<212> TYPE: PRT
<213> ORGANISM: Trichoderma reesei

<400> SEQUENCE: 58

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Ile Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
```

```
            385                 390                 395                 400
Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 59
<211> LENGTH: 447
<212> TYPE: PRT
<213> ORGANISM: Trichoderma reesei

<400> SEQUENCE: 59

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
                100                 105                 110

Ile Pro Ser Leu Thr Gly Ala Met Ala Thr Ala Ala Ala Ala Val Ala
                115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
                290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
```

```
                      325                 330                 335
Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 60
<211> LENGTH: 447
<212> TYPE: PRT
<213> ORGANISM: Trichoderma reesei

<400> SEQUENCE: 60

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Ala Val Ala
            115                 120                 125

Lys Val Pro Ser Phe Met Trp Leu Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
            210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
```

```
              260                 265                 270
Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gln Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 61
<211> LENGTH: 447
<212> TYPE: PRT
<213> ORGANISM: Trichoderma reesei

<400> SEQUENCE: 61

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
```

```
                195                 200                 205
Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 62
<211> LENGTH: 447
<212> TYPE: PRT
<213> ORGANISM: Trichoderma reesei

<400> SEQUENCE: 62

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Val Trp Ile Asp Thr Leu Asp Lys Thr Pro Leu
```

```
                  130                 135                 140
Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 63
<211> LENGTH: 447
<212> TYPE: PRT
<213> ORGANISM: Trichoderma reesei

<400> SEQUENCE: 63

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
                35                  40                  45

Arg Ala Ala Ser Thr Thr Ser Arg Val Ser Pro Thr Thr Ser Arg Ser
                50                  55                  60

Ser Ser Ala Thr Pro Pro Pro Gly Ser Thr Thr Thr Arg Val Pro Pro
```

65                  70                  75                  80
Val Gly Ser Gly Thr Ala Thr Tyr Ser Gly Asn Pro Phe Val Gly Val
                        85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Ile Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Ile Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 64
<211> LENGTH: 447
<212> TYPE: PRT
<213> ORGANISM: Trichoderma reesei

<400> SEQUENCE: 64

Gln Ala Cys Ser Ser Val Trp Gly Gln Cys Gly Gly Gln Asn Trp Ser

-continued

```
1               5                   10                  15
Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Ile Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430
```

```
Ala Tyr Phe Val Gln Leu Leu Thr Asn Ala Asn Pro Ser Phe Leu
        435                 440                 445
```

<210> SEQ ID NO 65
<211> LENGTH: 447
<212> TYPE: PRT
<213> ORGANISM: Trichoderma reesei

<400> SEQUENCE: 65

```
Gln Ala Cys Ser Ser Val Trp Gly Gln Cys Gly Gly Gln Asn Trp Ser
  1               5                  10                  15

Gly Pro Thr Cys Cys Ala Ser Gly Ser Thr Cys Val Tyr Ser Asn Asp
             20                  25                  30

Tyr Tyr Ser Gln Cys Leu Pro Gly Ala Ala Ser Ser Ser Ser Ser Thr
         35                  40                  45

Arg Ala Ala Ser Thr Thr Ser Arg Val Ser Pro Thr Thr Ser Arg Ser
     50                  55                  60

Ser Ser Ala Thr Pro Pro Pro Gly Ser Thr Thr Thr Arg Val Pro Pro
 65                  70                  75                  80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Ile Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gln Asp Trp Cys
        355                 360                 365
```

```
Asn Val Ile Gly Thr Gly Phe Gly Ile Arg Pro Ser Ala Asn Thr Gly
        370             375             380

Asp Ser Leu Leu Asp Ser Phe Val Trp Val Lys Pro Gly Gly Glu Cys
385             390             395             400

Asp Gly Thr Ser Asp Ser Ser Ala Pro Arg Phe Asp Pro His Cys Ala
            405             410             415

Leu Pro Asp Ala Leu Gln Pro Ala Pro Gln Ala Gly Ala Trp Phe Gln
        420             425             430

Ala Tyr Phe Val Gln Leu Leu Thr Asn Ala Asn Pro Ser Phe Leu
            435             440             445

<210> SEQ ID NO 66
<211> LENGTH: 447
<212> TYPE: PRT
<213> ORGANISM: Trichoderma reesei

<400> SEQUENCE: 66

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Ile Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300
```

```
Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445
```

<210> SEQ ID NO 67
<211> LENGTH: 447
<212> TYPE: PRT
<213> ORGANISM: Trichoderma reesei

<400> SEQUENCE: 67

```
Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240
```

```
Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gln Asp Trp Cys
            355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 68
<211> LENGTH: 447
<212> TYPE: PRT
<213> ORGANISM: Trichoderma reesei

<400> SEQUENCE: 68

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175
```

-continued

```
Ala Ala Leu Ala Ser Asn Gly Glu Tyr Tyr Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 69
<211> LENGTH: 447
<212> TYPE: PRT
<213> ORGANISM: Trichoderma reesei

<400> SEQUENCE: 69

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110
```

```
Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gln Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Ala Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 70
<211> LENGTH: 447
<212> TYPE: PRT
<213> ORGANISM: Trichoderma reesei

<400> SEQUENCE: 70

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Thr
            35                  40                  45
```

```
Arg Ala Ala Ser Thr Thr Ser Arg Val Ser Pro Thr Thr Ser Arg Ser
 50                  55                  60

Ser Ser Ala Thr Pro Pro Gly Ser Thr Thr Arg Val Pro Pro
 65                  70                  75                  80

Val Gly Ser Gly Thr Ala Thr Tyr Ser Gly Asn Pro Phe Val Gly Val
                 85                  90                  95

Thr Pro Trp Ala Asn Ala Leu Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gln Asp Trp Cys
                355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 71
<211> LENGTH: 447
<212> TYPE: PRT
<213> ORGANISM: Trichoderma reesei
```

```
<400> SEQUENCE: 71

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
            115                 120                 125

Lys Val Pro Ser Phe Val Trp Ile Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Ile Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415
```

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 72
<211> LENGTH: 447
<212> TYPE: PRT
<213> ORGANISM: Trichoderma reesei

<400> SEQUENCE: 72

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Ile Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

```
Arg Ser Gly Lys Gln Pro Thr Gly Gln Gln Trp Gln Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
        435                 440                 445

<210> SEQ ID NO 73
<211> LENGTH: 447
<212> TYPE: PRT
<213> ORGANISM: Trichoderma reesei

<400> SEQUENCE: 73

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Ile Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285
```

```
Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 74
<211> LENGTH: 447
<212> TYPE: PRT
<213> ORGANISM: Trichoderma reesei

<400> SEQUENCE: 74

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
                100                 105                 110

Ile Pro Ser Leu Thr Gly Ala Met Ala Thr Ala Ala Ala Ala Val Ala
            115                 120                 125

Lys Val Pro Ser Phe Met Trp Ile Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220
```

```
Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gln Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
            435                 440                 445

<210> SEQ ID NO 75
<211> LENGTH: 447
<212> TYPE: PRT
<213> ORGANISM: Trichoderma reesei

<400> SEQUENCE: 75

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160
```

```
Asn Tyr Ala Gly Gln Phe Val Val Tyr Asp Leu Pro Asp Arg Asp Cys
                165                 170                 175
Ala Ala Leu Ala Ser Asn Gly Glu Tyr Tyr Ile Ala Asp Gly Gly Val
            180                 185                 190
Ala Lys Tyr Lys Asn Tyr Ile Asp Thr Ile Arg Gln Ile Val Val Glu
        195                 200                 205
Tyr Ser Asp Ile Arg Thr Leu Leu Val Ile Glu Pro Asp Ser Leu Ala
    210                 215                 220
Asn Leu Val Thr Asn Leu Gly Thr Pro Lys Cys Ala Asn Ala Gln Ser
225                 230                 235                 240
Ala Tyr Leu Glu Cys Ile Asn Tyr Ala Val Thr Gln Leu Asn Leu Pro
                245                 250                 255
Asn Val Ala Met Tyr Leu Asp Ala Gly His Ala Gly Trp Leu Gly Trp
            260                 265                 270
Pro Ala Asn Gln Asp Pro Ala Ala Gln Leu Phe Ala Asn Val Tyr Lys
        275                 280                 285
Asn Ala Ser Ser Pro Arg Ala Leu Arg Gly Leu Ala Thr Asn Val Ala
    290                 295                 300
Asn Tyr Asn Gly Trp Asn Ile Thr Ser Pro Pro Ser Tyr Thr Gln Gly
305                 310                 315                 320
Asn Ala Val Tyr Asn Glu Lys Leu Tyr Ile His Ala Ile Gly Pro Leu
                325                 330                 335
Leu Ala Asn His Gly Trp Ser Asn Ala Phe Phe Ile Thr Asp Gln Gly
            340                 345                 350
Arg Ser Gly Lys Gln Pro Thr Gly Gln Gln Gln Trp Gln Asp Trp Cys
        355                 360                 365
Asn Val Ile Gly Thr Gly Phe Gly Ile Arg Pro Ser Ala Asn Thr Gly
    370                 375                 380
Asp Ser Leu Leu Asp Ser Phe Val Trp Val Lys Pro Gly Gly Glu Cys
385                 390                 395                 400
Asp Gly Thr Ser Asp Ser Ser Ala Pro Gln Phe Asp Pro His Cys Ala
                405                 410                 415
Leu Pro Asp Ala Leu Gln Pro Ala Pro Gln Ala Gly Ala Trp Phe Gln
            420                 425                 430
Ala Tyr Phe Val Gln Leu Leu Thr Asn Ala Asn Pro Ser Phe Leu
        435                 440                 445

<210> SEQ ID NO 76
<211> LENGTH: 447
<212> TYPE: PRT
<213> ORGANISM: Trichoderma reesei

<400> SEQUENCE: 76

Gln Ala Cys Ser Ser Val Trp Gly Gln Cys Gly Gly Gln Asn Trp Ser
1               5                   10                  15
Gly Pro Thr Cys Cys Ala Ser Gly Ser Thr Cys Val Tyr Ser Asn Asp
            20                  25                  30
Tyr Tyr Ser Gln Cys Leu Pro Gly Ala Ala Ser Ser Ser Ser Ser Thr
        35                  40                  45
Arg Ala Ala Ser Thr Thr Ser Arg Val Ser Pro Thr Thr Ser Arg Ser
    50                  55                  60
Ser Ser Ala Thr Pro Pro Pro Gly Ser Thr Thr Thr Arg Val Pro Pro
65                  70                  75                  80
Val Gly Ser Gly Thr Ala Thr Tyr Ser Gly Asn Pro Phe Val Gly Val
                85                  90                  95
```

```
Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Ile Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
                290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gln Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 77
<211> LENGTH: 447
<212> TYPE: PRT
<213> ORGANISM: Trichoderma reesei

<400> SEQUENCE: 77

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

```
Tyr Tyr Ser Gln Cys Leu Pro Gly Ala Ala Ser Ser Ser Ser Thr
        35                  40                  45

Arg Ala Ala Ser Thr Thr Ser Arg Val Ser Pro Thr Thr Ser Arg Ser
 50                  55                  60

Ser Ser Ala Thr Pro Pro Gly Ser Thr Thr Arg Val Pro Pro
 65              70                  75                  80

Val Gly Ser Gly Thr Ala Thr Tyr Ser Gly Asn Pro Phe Val Gly Val
                 85                  90                  95

Thr Pro Trp Ala Asn Ala Leu Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Ile Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Tyr Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
                210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
                290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gln Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445
```

<210> SEQ ID NO 78
<211> LENGTH: 453
<212> TYPE: PRT
<213> ORGANISM: Humicola insolens

<400> SEQUENCE: 78

```
Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Ser Arg Ala Thr Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Ala Ser Tyr Asn Gly Asn Pro
                85                  90                  95

Phe Glu Gly Val Gln Leu Trp Ala Asn Asn Lys Tyr Arg Ser Glu Val
                100                 105                 110

His Thr Leu Ala Ile Pro Gln Ile Thr Asp Pro Ala Leu Arg Ala Ala
            115                 120                 125

Ala Ser Ala Val Ala Glu Val Pro Ser Phe Gln Trp Leu Asp Arg Asn
130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
                195                 200                 205

Arg Ile Arg Glu Ile Leu Ile Ser Phe Ser Asp Val Arg Thr Ile Leu
            210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
```

```
            385                 390                 395                 400
Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
        450

<210> SEQ ID NO 79
<211> LENGTH: 453
<212> TYPE: PRT
<213> ORGANISM: Humicola insolens

<400> SEQUENCE: 79

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Ser Thr Thr
        35                  40                  45

Thr Ser Thr Ser Ser Ser Thr Thr Ser Arg Ala Thr Ser Thr Thr
    50                  55                  60

Arg Thr Gly Gly Val Thr Ser Ile Thr Ala Pro Thr Arg Thr Val
65                  70                  75                  80

Thr Ile Pro Gly Gly Ala Thr Thr Ala Ser Tyr Asn Gly Asn Pro
            85                  90                  95

Phe Glu Gly Val Gln Leu Trp Ala Asn Asn Leu Tyr Arg Ser Glu Val
        100                 105                 110

His Thr Leu Ala Ile Pro Gln Ile Thr Asp Pro Ala Leu Arg Ala Ala
            115                 120                 125

Ala Ser Ala Val Ala Glu Val Pro Ser Phe Gln Trp Leu Asp Arg Asn
        130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
            165                 170                 175

Tyr Asp Leu Pro Asp Arg Asp Cys Ala Ala Ala Ala Ser Asn Gly Glu
        180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
            245                 250                 255

Ala Leu Lys Gln Leu Asp Leu Pro His Val Ala Met Tyr Met Asp Ala
        260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
        290                 295                 300

Arg Gly Leu Ala Thr Asn Val Ala Asn Tyr Asn Ala Trp Ser Ile Ser
```

```
                 305                 310                 315                 320

Ser Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
                355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
                435                 440                 445

Ala Asn Pro Pro Phe
    450

<210> SEQ ID NO 80
<211> LENGTH: 453
<212> TYPE: PRT
<213> ORGANISM: Humicola insolens

<400> SEQUENCE: 80

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
                20                  25                  30

Trp Tyr Ser Gln Cys Leu Pro Gly Ser Gln Val Thr Thr Thr Ser Thr
            35                  40                  45

Thr Ser Thr Ser Ser Ser Ser Thr Thr Ser Arg Ala Thr Ser Thr Thr
        50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
                100                 105                 110

His Thr Leu Ala Ile Pro Gln Ile Thr Asp Pro Ala Leu Arg Ala Ala
            115                 120                 125

Ala Ser Ala Val Ala Glu Val Pro Ser Phe Thr Trp Leu Asp Arg Asn
        130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
                180                 185                 190

Trp Ala Ile Ala Asn Asn Gly Ala Asn Tyr Lys Gly Tyr Ile Asn
            195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
```

```
                225                 230                 235                 240
Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
                260                 265                 270

Gly His Ala Gly Trp Leu Gly Trp Pro Ala Asn Ile Gln Pro Ala Ala
                275                 280                 285

Glu Leu Phe Ala Lys Ile Tyr Glu Asp Ala Gly Lys Pro Arg Ala Val
                290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
                355                 360                 365

Lys Glu Trp Gly His Trp Cys Asn Ala Ile Gly Thr Gly Phe Gly Met
                370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
                435                 440                 445

Ala Asn Pro Pro Phe
                450

<210> SEQ ID NO 81
<211> LENGTH: 453
<212> TYPE: PRT
<213> ORGANISM: Humicola insolens

<400> SEQUENCE: 81

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
                20                  25                  30

Trp Tyr Ser Gln Cys Leu Pro Gly Ser Gln Val Thr Thr Ser Thr Thr
                35                  40                  45

Thr Ser Thr Ser Ser Ser Ser Thr Ser Arg Ala Thr Ser Thr Thr
            50                  55                  60

Arg Thr Gly Gly Val Thr Ser Ile Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
                100                 105                 110

His Thr Leu Ala Ile Pro Gln Ile Thr Asp Pro Ala Leu Arg Ala Ala
                115                 120                 125

Ala Ser Ala Val Ala Glu Val Pro Ser Phe Gln Trp Val Asp Arg Asn
                130                 135                 140

Val Thr Val Asp Thr Leu Leu Val Glu Thr Leu Ser Glu Ile Arg Ala
```

```
            145                 150                 155                 160
Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
            195                 200                 205

Arg Ile Arg Glu Ile Leu Ile Ser Phe Ser Asp Val Arg Thr Ile Leu
        210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
                260                 265                 270

Gly His Ala Gly Trp Leu Gly Trp Pro Ala Asn Ile Gln Pro Ala Ala
                275                 280                 285

Glu Leu Phe Ala Lys Ile Tyr Glu Asp Ala Gly Lys Pro Arg Ala Val
        290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
                355                 360                 365

Lys Glu Trp Gly His Trp Cys Asn Ala Ile Gly Thr Gly Phe Gly Met
        370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
                435                 440                 445

Ala Asn Pro Pro Phe
        450

<210> SEQ ID NO 82
<211> LENGTH: 453
<212> TYPE: PRT
<213> ORGANISM: Humicola insolens

<400> SEQUENCE: 82

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
                20                  25                  30

Trp Tyr Ser Gln Cys Leu Pro Gly Ser Gln Val Thr Thr Thr Ser Thr
            35                  40                  45

Thr Ser Thr Ser Ser Ser Thr Ser Arg Ala Thr Ser Thr
        50                  55                  60

Arg Thr Gly Gly Val Thr Ser Ile Thr Thr Ala Pro Thr Arg Thr Val
```

```
            65                  70                  75                  80
Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Tyr Ile Ala Asn Asn Gly Ala Asn Tyr Lys Gly Tyr Ile Asn
                195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
    450

<210> SEQ ID NO 83
<211> LENGTH: 440
<212> TYPE: PRT
<213> ORGANISM: Phanerochaete chrysosporium
```

<400> SEQUENCE: 83

| Ala | Ser | Ser | Glu | Trp | Gly | Gln | Cys | Gly | Ile | Gly | Trp | Thr | Gly | Pro |
|---|---|---|---|---|---|---|---|---|---|---|---|---|---|---|
| 1 | | | | 5 | | | | | 10 | | | | | 15 |

| Thr | Thr | Cys | Val | Ser | Gly | Thr | Thr | Cys | Thr | Val | Leu | Asn | Pro | Tyr | Tyr |
|---|---|---|---|---|---|---|---|---|---|---|---|---|---|---|---|
| | | | 20 | | | | | 25 | | | | | 30 | | |

| Ser | Gln | Cys | Leu | Pro | Gly | Ser | Ala | Val | Thr | Thr | Ser | Val | Ile | Thr |
|---|---|---|---|---|---|---|---|---|---|---|---|---|---|---|
| | | | 35 | | | | | 40 | | | | | 45 | |

| Ser | His | Ser | Ser | Ser | Val | Ser | Ser | Val | Ser | Ser | His | Ser | Gly | Ser | Ser |
|---|---|---|---|---|---|---|---|---|---|---|---|---|---|---|---|
| | 50 | | | | | 55 | | | | | 60 | | | | |

| Thr | Ser | Thr | Ser | Ser | Pro | Thr | Gly | Pro | Thr | Gly | Thr | Asn | Pro | Pro |
|---|---|---|---|---|---|---|---|---|---|---|---|---|---|---|
| 65 | | | | | 70 | | | | 75 | | | | | 80 |

| Pro | Pro | Ser | Ala | Asn | Asn | Pro | Trp | Thr | Gly | Phe | Gln | Ile | Phe | Leu | Ser |
|---|---|---|---|---|---|---|---|---|---|---|---|---|---|---|---|
| | | | | 85 | | | | | 90 | | | | | 95 | |

| Pro | Lys | Tyr | Ala | Asn | Glu | Val | Ala | Ala | Ala | Lys | Gln | Ile | Thr | Asp |
|---|---|---|---|---|---|---|---|---|---|---|---|---|---|---|
| | | | 100 | | | | | 105 | | | | | 110 | |

| Pro | Thr | Leu | Ser | Ser | Lys | Ala | Ala | Ser | Val | Ala | Asn | Ile | Pro | Thr | Phe |
|---|---|---|---|---|---|---|---|---|---|---|---|---|---|---|---|
| | | | 115 | | | | | 120 | | | | | 125 | | |

| Thr | Trp | Leu | Asp | Ser | Val | Ala | Lys | Ile | Pro | Asp | Leu | Gly | Thr | Tyr | Leu |
|---|---|---|---|---|---|---|---|---|---|---|---|---|---|---|---|
| | 130 | | | | | 135 | | | | | 140 | | | | |

| Ala | Ser | Ala | Ser | Ala | Leu | Gly | Lys | Ser | Thr | Gly | Thr | Lys | Gln | Leu | Val |
|---|---|---|---|---|---|---|---|---|---|---|---|---|---|---|---|
| 145 | | | | | 150 | | | | | 155 | | | | | 160 |

| Gln | Ile | Val | Ile | Tyr | Asp | Leu | Pro | Asp | Arg | Asp | Cys | Ala | Ala | Lys | Ala |
|---|---|---|---|---|---|---|---|---|---|---|---|---|---|---|---|
| | | | | 165 | | | | | 170 | | | | | 175 | |

| Ser | Asn | Gly | Glu | Phe | Ser | Ile | Ala | Asn | Asn | Gly | Gln | Ala | Asn | Tyr | Glu |
|---|---|---|---|---|---|---|---|---|---|---|---|---|---|---|---|
| | | | 180 | | | | | 185 | | | | | 190 | | |

| Asn | Tyr | Ile | Asp | Gln | Ile | Val | Ala | Gln | Ile | Gln | Gln | Phe | Pro | Asp | Val |
|---|---|---|---|---|---|---|---|---|---|---|---|---|---|---|---|
| | | 195 | | | | | 200 | | | | | 205 | | | |

| Arg | Val | Val | Ala | Val | Ile | Glu | Pro | Asp | Ser | Leu | Ala | Asn | Leu | Val | Thr |
|---|---|---|---|---|---|---|---|---|---|---|---|---|---|---|---|
| | 210 | | | | | 215 | | | | | 220 | | | | |

| Asn | Leu | Asn | Val | Gln | Lys | Cys | Ala | Asn | Ala | Lys | Thr | Thr | Tyr | Leu | Ala |
|---|---|---|---|---|---|---|---|---|---|---|---|---|---|---|---|
| 225 | | | | | 230 | | | | | 235 | | | | | 240 |

| Cys | Val | Asn | Tyr | Ala | Leu | Thr | Asn | Leu | Ala | Lys | Val | Gly | Val | Tyr | Met |
|---|---|---|---|---|---|---|---|---|---|---|---|---|---|---|---|
| | | | | 245 | | | | | 250 | | | | | 255 | |

| Tyr | Met | Asp | Ala | Gly | His | Ala | Gly | Trp | Leu | Gly | Trp | Pro | Ala | Asn | Leu |
|---|---|---|---|---|---|---|---|---|---|---|---|---|---|---|---|
| | | | 260 | | | | | 265 | | | | | 270 | | |

| Ser | Pro | Ala | Ala | Gln | Leu | Phe | Thr | Gln | Val | Trp | Gln | Asn | Ala | Gly | Lys |
|---|---|---|---|---|---|---|---|---|---|---|---|---|---|---|---|
| | | 275 | | | | | 280 | | | | | 285 | | | |

| Ser | Pro | Phe | Ile | Lys | Gly | Leu | Ala | Thr | Asn | Val | Ala | Asn | Tyr | Asn | Ala |
|---|---|---|---|---|---|---|---|---|---|---|---|---|---|---|---|
| | 290 | | | | | 295 | | | | | 300 | | | | |

| Leu | Gln | Ala | Ala | Ser | Pro | Asp | Pro | Ile | Thr | Gln | Gly | Asn | Pro | Asn | Tyr |
|---|---|---|---|---|---|---|---|---|---|---|---|---|---|---|---|
| 305 | | | | | 310 | | | | | 315 | | | | | 320 |

| Asp | Glu | Ile | His | Tyr | Ile | Asn | Ala | Leu | Ala | Pro | Leu | Leu | Gln | Gln | Ala |
|---|---|---|---|---|---|---|---|---|---|---|---|---|---|---|---|
| | | | | 325 | | | | | 330 | | | | | 335 | |

| Gly | Trp | Asp | Ala | Thr | Phe | Ile | Val | Asp | Gln | Gly | Arg | Ser | Gly | Val | Gln |
|---|---|---|---|---|---|---|---|---|---|---|---|---|---|---|---|
| | | | 340 | | | | | 345 | | | | | 350 | | |

| Asn | Ile | Arg | Gln | Gln | Trp | Gly | Asp | Trp | Cys | Asn | Ile | Lys | Gly | Ala | Gly |
|---|---|---|---|---|---|---|---|---|---|---|---|---|---|---|---|
| | | 355 | | | | | 360 | | | | | 365 | | | |

| Phe | Gly | Thr | Arg | Pro | Thr | Thr | Asn | Thr | Gly | Ser | Gln | Phe | Ile | Asp | Ser |
|---|---|---|---|---|---|---|---|---|---|---|---|---|---|---|---|
| | 370 | | | | | 375 | | | | | 380 | | | | |

| Ile | Val | Trp | Val | Lys | Pro | Gly | Gly | Glu | Cys | Asp | Gly | Thr | Ser | Asn | Ser |
|---|---|---|---|---|---|---|---|---|---|---|---|---|---|---|---|
| 385 | | | | | 390 | | | | | 395 | | | | | 400 |

| Ser | Ser | Pro | Arg | Tyr | Asp | Ser | Thr | Cys | Ser | Leu | Pro | Asp | Ala | Ala | Gln |
|---|---|---|---|---|---|---|---|---|---|---|---|---|---|---|---|
| | | | 405 | | | | | 410 | | | | | 415 | | |

Pro Ala Pro Glu Ala Gly Thr Trp Phe Gln Ala Tyr Phe Gln Thr Leu
            420                 425                 430

Val Ser Ala Ala Asn Pro Pro Leu
            435                 440

<210> SEQ ID NO 84
<211> LENGTH: 440
<212> TYPE: PRT
<213> ORGANISM: Phanerochaete chrysosporium

<400> SEQUENCE: 84

Ala Ser Ser Glu Trp Gly Gln Cys Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Ser Val Ile Thr
            35                  40                  45

Ser His Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Leu Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
            130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
            195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
            290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

```
Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
            405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
            435                 440

<210> SEQ ID NO 85
<211> LENGTH: 440
<212> TYPE: PRT
<213> ORGANISM: Phanerochaete chrysosporium

<400> SEQUENCE: 85

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Thr Ser Val Ile Thr
        35                  40                  45

Ser His Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
            85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Ile Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285
```

```
Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
    370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
    435                 440

<210> SEQ ID NO 86
<211> LENGTH: 440
<212> TYPE: PRT
<213> ORGANISM: Phanerochaete chrysosporium

<400> SEQUENCE: 86

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Thr Ser Val Ile Thr
            35                  40                  45

Ser His Ser Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Val Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
    210                 215                 220
```

```
Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
            245                 250                 255

Tyr Met Asp Ala Gly His Ala Gly Trp Leu Gly Trp Pro Ala Asn Leu
        260                 265                 270

Ser Pro Ala Ala Gln Leu Phe Thr Gln Val Trp Gln Asn Ala Gly Lys
    275                 280                 285

Ser Pro Phe Ile Lys Gly Leu Ala Thr Asn Val Ala Asn Tyr Asn Ala
    290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
            405                 410                 415

Pro Ala Pro Glu Ala Gly Thr Trp Phe Gln Ala Tyr Phe Gln Thr Leu
        420                 425                 430

Val Ser Ala Ala Asn Pro Pro Leu
        435                 440

<210> SEQ ID NO 87
<211> LENGTH: 440
<212> TYPE: PRT
<213> ORGANISM: Phanerochaete chrysosporium

<400> SEQUENCE: 87

Ala Ser Ser Glu Trp Gly Gln Cys Gly Gly Ile Gly Trp Thr Gly Pro
1               5                   10                  15

Thr Thr Cys Val Ser Gly Thr Cys Thr Val Leu Asn Pro Tyr Tyr
            20                  25                  30

Ser Gln Cys Leu Pro Gly Ser Ala Val Thr Thr Thr Ser Val Ile Thr
        35                  40                  45

Ser His Ser Ser Ser Val Ser Ser Val Ser Ser His Ser Gly Ser Ser
    50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
    130                 135                 140

Ala Ser Ala Ser Ala Leu Gly Lys Ser Thr Gly Thr Lys Gln Leu Val
145                 150                 155                 160
```

```
Gln Ile Val Ile Tyr Asp Leu Pro Asp Arg Asp Cys Ala Ala Lys Ala
                165                 170                 175

Ser Asn Gly Glu Phe Lys Ile Ala Asn Gly Gln Ala Asn Tyr Glu
            180                 185                 190

Asn Tyr Ile Asp Gln Ile Val Ala Gln Ile Gln Gln Phe Pro Asp Val
                195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
                260                 265                 270

Ser Pro Ala Ala Gln Leu Phe Thr Gln Val Trp Gln Asn Ala Gly Lys
            275                 280                 285

Ser Pro Phe Ile Lys Gly Leu Ala Thr Asn Val Ala Asn Tyr Asn Ala
            290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
            355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
            435                 440

<210> SEQ ID NO 88
<211> LENGTH: 440
<212> TYPE: PRT
<213> ORGANISM: Phanerochaete chrysosporium

<400> SEQUENCE: 88

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Ser Val Ile Thr
            35                  40                  45

Ser His Ser Ser Ser Val Ser Ser Val Ser Ser His Ser Gly Ser Ser
            50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95
```

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
        115                 120                 125

Thr Trp Leu Asp Ser Val Ala Lys Ile Pro Asp Leu Gly Thr Tyr Leu
130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Tyr Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 89
<211> LENGTH: 440
<212> TYPE: PRT
<213> ORGANISM: Phanerochaete chrysosporium

<400> SEQUENCE: 89

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
            20                  25                  30

Ser Gln Cys Leu Pro Gly Ser Ala Val Thr Thr Ser Val Ile Thr
 35                  40                  45

Ser His Ser Ser Ser Val Ser Ser Val Ser His Ser Gly Ser Ser
 50                  55                  60

Thr Ser Thr Ser Ser Pro Thr Gly Pro Thr Gly Thr Asn Pro Pro Pro
 65                  70                  75                  80

Pro Pro Ser Ala Asn Asn Pro Trp Thr Gly Phe Gln Ile Phe Leu Ser
                 85                  90                  95

Pro Tyr Tyr Ala Asn Glu Val Ala Ala Ala Lys Gln Ile Thr Asp
             100                 105                 110

Pro Thr Leu Ser Ser Lys Ala Ala Ser Val Ala Asn Ile Pro Thr Phe
             115                 120                 125

Thr Trp Leu Asp Ser Val Ala Lys Ile Pro Asp Leu Gly Thr Tyr Leu
 130                 135                 140

Ala Ser Ala Ser Ala Leu Gly Lys Ser Thr Gly Thr Lys Gln Leu Val
 145                 150                 155                 160

Gln Ile Val Ile Tyr Asp Leu Pro Asp Arg Asp Cys Ala Ala Lys Ala
                 165                 170                 175

Ser Asn Gly Glu Phe Ser Ile Ala Asn Asn Gly Gln Ala Asn Tyr Glu
             180                 185                 190

Asn Tyr Ile Asp Gln Ile Val Ala Gln Ile Gln Gln Phe Pro Asp Val
             195                 200                 205

Arg Val Val Ala Val Ile Glu Pro Asp Ser Leu Ala Asn Leu Val Thr
 210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                 245                 250                 255

Tyr Met Asp Ala Gly His Ala Gly Trp Leu Gly Trp Pro Ala Asn Leu
             260                 265                 270

Ser Pro Ala Ala Gln Leu Phe Thr Gln Val Trp Gln Asn Ala Gly Lys
             275                 280                 285

Ser Pro Phe Ile Lys Gly Leu Ala Thr Asn Val Ala Asn Tyr Asn Ala
 290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                 325                 330                 335

Gly Trp Asp Ala Thr Phe Ile Val Asp Gln Gly Arg Ser Gly Val Gln
             340                 345                 350

Asn Ile Arg Gln Gln Trp Gln Asp Trp Cys Asn Ile Lys Gly Ala Gly
             355                 360                 365

Phe Gly Thr Arg Pro Thr Thr Asn Thr Gly Ser Gln Phe Ile Asp Ser
 370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                 405                 410                 415

Pro Ala Pro Glu Ala Gly Thr Trp Phe Gln Ala Tyr Phe Gln Thr Leu
             420                 425                 430

Val Ser Ala Ala Asn Pro Pro Leu
 435                 440

<210> SEQ ID NO 90

```
<211> LENGTH: 440
<212> TYPE: PRT
<213> ORGANISM: Phanerochaete chrysosporium

<400> SEQUENCE: 90
```

| | | | | | | | | | | | | | | |
|---|---|---|---|---|---|---|---|---|---|---|---|---|---|---|
| Ala | Ser | Ser | Glu | Trp | Gly | Gln | Cys | Gly | Ile | Gly | Trp | Thr | Gly | Pro |
| 1 | | | | 5 | | | | | 10 | | | | | 15 |
| Thr | Thr | Cys | Val | Ser | Gly | Thr | Thr | Cys | Thr | Val | Leu | Asn | Pro | Tyr | Tyr |
| | | | 20 | | | | | 25 | | | | | 30 | | |
| Ser | Gln | Cys | Leu | Pro | Gly | Ser | Ala | Val | Thr | Thr | Ser | Val | Ile | Thr |
| | | 35 | | | | | 40 | | | | | 45 | | |
| Ser | His | Ser | Ser | Ser | Val | Ser | Val | Ser | Ser | His | Ser | Gly | Ser | Ser |
| | 50 | | | | | 55 | | | | | 60 | | | |
| Thr | Ser | Thr | Ser | Ser | Pro | Thr | Gly | Pro | Thr | Gly | Thr | Asn | Pro | Pro |
| 65 | | | | | 70 | | | | | 75 | | | | 80 |
| Pro | Pro | Ser | Ala | Asn | Asn | Pro | Trp | Thr | Gly | Phe | Gln | Ile | Phe | Leu | Ser |
| | | | | 85 | | | | | 90 | | | | | 95 | |
| Pro | Tyr | Tyr | Ala | Asn | Glu | Val | Ala | Ala | Ala | Lys | Gln | Ile | Thr | Asp |
| | | | 100 | | | | | 105 | | | | | 110 | |
| Pro | Thr | Leu | Ser | Ser | Lys | Ala | Ala | Ser | Val | Ala | Asn | Ile | Pro | Thr | Phe |
| | | | 115 | | | | | 120 | | | | | 125 | | |
| Thr | Trp | Leu | Asp | Ser | Val | Ala | Lys | Ile | Pro | Asp | Leu | Gly | Thr | Tyr | Leu |
| | 130 | | | | | 135 | | | | | 140 | | | | |
| Ala | Ser | Ala | Ser | Ala | Leu | Gly | Lys | Ser | Thr | Gly | Thr | Lys | Gln | Leu | Val |
| 145 | | | | | 150 | | | | | 155 | | | | | 160 |
| Gln | Ile | Val | Ile | Tyr | Asp | Leu | Pro | Asp | Arg | Asp | Cys | Ala | Ala | Lys | Ala |
| | | | | 165 | | | | | 170 | | | | | 175 | |
| Ser | Asn | Gly | Glu | Phe | Ser | Ile | Ala | Asn | Asn | Gly | Gln | Ala | Asn | Tyr | Glu |
| | | | 180 | | | | | 185 | | | | | 190 | | |
| Asn | Tyr | Ile | Asp | Gln | Ile | Val | Ala | Gln | Ile | Gln | Gln | Phe | Pro | Asp | Val |
| | | | 195 | | | | | 200 | | | | | 205 | | |
| Arg | Val | Val | Ala | Val | Ile | Glu | Pro | Asp | Ser | Leu | Ala | Asn | Leu | Val | Thr |
| | 210 | | | | | 215 | | | | | 220 | | | | |
| Asn | Leu | Asn | Val | Gln | Lys | Cys | Ala | Asn | Ala | Lys | Thr | Thr | Tyr | Leu | Ala |
| 225 | | | | | 230 | | | | | 235 | | | | | 240 |
| Cys | Val | Asn | Tyr | Ala | Leu | Thr | Asn | Leu | Ala | Lys | Val | Gly | Val | Tyr | Met |
| | | | | 245 | | | | | 250 | | | | | 255 | |
| Tyr | Met | Asp | Ala | Gly | His | Ala | Gly | Trp | Leu | Gly | Trp | Pro | Ala | Asn | Leu |
| | | | 260 | | | | | 265 | | | | | 270 | | |
| Ser | Pro | Ala | Ala | Gln | Leu | Phe | Thr | Gln | Val | Trp | Gln | Asn | Ala | Gly | Lys |
| | | | 275 | | | | | 280 | | | | | 285 | | |
| Ser | Pro | Phe | Ile | Lys | Gly | Leu | Ala | Thr | Asn | Val | Ala | Asn | Tyr | Asn | Ala |
| | 290 | | | | | 295 | | | | | 300 | | | | |
| Leu | Gln | Ala | Ala | Ser | Pro | Asp | Pro | Ile | Thr | Gln | Gly | Asn | Pro | Asn | Tyr |
| 305 | | | | | 310 | | | | | 315 | | | | | 320 |
| Asp | Glu | Ile | His | Tyr | Ile | Asn | Ala | Leu | Ala | Pro | Leu | Leu | Gln | Gln | Ala |
| | | | | 325 | | | | | 330 | | | | | 335 | |
| Gly | Trp | Asp | Ala | Thr | Phe | Ile | Val | Asp | Gln | Gly | Arg | Ser | Gly | Val | Gln |
| | | | 340 | | | | | 345 | | | | | 350 | | |
| Asn | Ile | Arg | Gln | Gln | Trp | Gly | Asp | Trp | Cys | Asn | Ile | Lys | Gly | Ala | Gly |
| | | | 355 | | | | | 360 | | | | | 365 | | |
| Phe | Gly | Thr | Arg | Pro | Thr | Thr | Asn | Thr | Gly | Ser | Gln | Phe | Ile | Asp | Ser |
| | 370 | | | | | 375 | | | | | 380 | | | | |
| Ile | Val | Trp | Val | Lys | Pro | Gly | Gly | Glu | Cys | Asp | Gly | Thr | Ser | Asn | Ser |
| 385 | | | | | 390 | | | | | 395 | | | | | 400 |

```
Ser Ser Pro Gln Tyr Asp Ser Thr Cys Ser Leu Pro Asp Ala Ala Gln
            405                 410                 415
Pro Ala Pro Glu Ala Gly Thr Trp Phe Gln Ala Tyr Phe Gln Thr Leu
            420                 425                 430
Val Ser Ala Ala Asn Pro Pro Leu
        435                 440
```

<210> SEQ ID NO 91
<211> LENGTH: 30
<212> TYPE: DNA
<213> ORGANISM: Artificial
<220> FEATURE:
<223> OTHER INFORMATION: Primer sequence

<400> SEQUENCE: 91
accaaaagat ctatgagatt tccttcaatt                              30

<210> SEQ ID NO 92
<211> LENGTH: 30
<212> TYPE: DNA
<213> ORGANISM: Artificial
<220> FEATURE:
<223> OTHER INFORMATION: Primer sequence

<400> SEQUENCE: 92
tgagcagcta gccctttat ccaaagatac                               30

<210> SEQ ID NO 93
<211> LENGTH: 30
<212> TYPE: DNA
<213> ORGANISM: Artificial
<220> FEATURE:
<223> OTHER INFORMATION: Primer sequence

<400> SEQUENCE: 93
aaaagggcta gctgctcaag cgtctggggc                              30

<210> SEQ ID NO 94
<211> LENGTH: 36
<212> TYPE: DNA
<213> ORGANISM: Artificial
<220> FEATURE:
<223> OTHER INFORMATION: Primer sequence

<400> SEQUENCE: 94
gagctcagat ctggtacctt acaggaacga tgggtt                       36

<210> SEQ ID NO 95
<211> LENGTH: 21
<212> TYPE: DNA
<213> ORGANISM: Artificial
<220> FEATURE:
<223> OTHER INFORMATION: Primer sequence

<400> SEQUENCE: 95
agcacaaata acgggttatt g                                       21

<210> SEQ ID NO 96
<211> LENGTH: 23
<212> TYPE: DNA
<213> ORGANISM: Artificial
<220> FEATURE:
<223> OTHER INFORMATION: Primer sequence

<400> SEQUENCE: 96

```
gcaacacctg gcaattcctt acc                                          23
```

<210> SEQ ID NO 97
<211> LENGTH: 28
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (15)..(16)
<223> OTHER INFORMATION: n is a, c, g, or t

<400> SEQUENCE: 97

```
gagtatctag ccasnnaaaa gagggaac                                     28
```

<210> SEQ ID NO 98
<211> LENGTH: 29
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (17)..(18)
<223> OTHER INFORMATION: n is a, c, g, or t

<400> SEQUENCE: 98

```
cttgtcaaga gtatcsnncc acataaaag                                    29
```

<210> SEQ ID NO 99
<211> LENGTH: 28
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (15)..(16)
<223> OTHER INFORMATION: n is a, c, g, or t

<400> SEQUENCE: 99

```
gctcaataac cagsnnggtc cggatatc                                     28
```

<210> SEQ ID NO 100
<211> LENGTH: 27
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (15)..(16)
<223> OTHER INFORMATION: n is a, c, g, or t

<400> SEQUENCE: 100

```
cttcagaggc gtasnntgca ttggccc                                      27
```

<210> SEQ ID NO 101
<211> LENGTH: 29
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (15)..(16)
<223> OTHER INFORMATION: n is a, c, g, or t

<400> SEQUENCE: 101
caccatcggc aatsnngtat tcgccattc                                    29

<210> SEQ ID NO 102
<211> LENGTH: 28
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (13)..(14)
<223> OTHER INFORMATION: n is a, c, g, or t

<400> SEQUENCE: 102
cagcaacagt ggnnsgactg gtgcaatg                                     28

<210> SEQ ID NO 103
<211> LENGTH: 35
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (16)..(17)
<223> OTHER INFORMATION: n is a, c, g, or t

<400> SEQUENCE: 103
gacagcagtg cgccannstt tgaccccac tgtgc                              35

<210> SEQ ID NO 104
<211> LENGTH: 33
<212> TYPE: DNA
<213> ORGANISM: Artificial
<220> FEATURE:
<223> OTHER INFORMATION: Primer sequence

<400> SEQUENCE: 104
gttccctctt ttgtgtggat agatactctt gac                               33

<210> SEQ ID NO 105
<211> LENGTH: 27
<212> TYPE: DNA
<213> ORGANISM: Artificial
<220> FEATURE:
<223> OTHER INFORMATION: Primer sequence

<400> SEQUENCE: 105
gttccctctt ttgtgtggct agatact                                      27

<210> SEQ ID NO 106
<211> LENGTH: 46
<212> TYPE: DNA
<213> ORGANISM: Artificial
<220> FEATURE:
<223> OTHER INFORMATION: Primer sequence

<400> SEQUENCE: 106
ctagtcatca ccatcaccat cacgctagct gatcactgag gtaccg                 46

<210> SEQ ID NO 107
<211> LENGTH: 46
<212> TYPE: DNA
<213> ORGANISM: Artificial
<220> FEATURE:
<223> OTHER INFORMATION: Primer sequence

<400> SEQUENCE: 107

-continued

```
aattcggtac ctcagtgatc agctagcgtg atggtgatgg tgatga                    46

<210> SEQ ID NO 108
<211> LENGTH: 35
<212> TYPE: DNA
<213> ORGANISM: Artificial
<220> FEATURE:
<223> OTHER INFORMATION: Primer sequence

<400> SEQUENCE: 108
ctattgctag ctgtgccccg acttggggcc agtgc                                35

<210> SEQ ID NO 109
<211> LENGTH: 44
<212> TYPE: DNA
<213> ORGANISM: Artificial
<220> FEATURE:
<223> OTHER INFORMATION: Primer sequence

<400> SEQUENCE: 109
ctattgaatt cggtacctca gaacggcgga ttggcattac gaag                      44

<210> SEQ ID NO 110
<211> LENGTH: 35
<212> TYPE: DNA
<213> ORGANISM: Artificial
<220> FEATURE:
<223> OTHER INFORMATION: Primer sequence

<400> SEQUENCE: 110
ctattgctag ctcggagtgg ggacagtgcg gtggc                                35

<210> SEQ ID NO 111
<211> LENGTH: 44
<212> TYPE: DNA
<213> ORGANISM: Artificial
<220> FEATURE:
<223> OTHER INFORMATION: Primer sequence

<400> SEQUENCE: 111
ctattgaatt cggtacccta cagcggcggg ttggcagcag aaac                      44

<210> SEQ ID NO 112
<211> LENGTH: 33
<212> TYPE: DNA
<213> ORGANISM: Artificial
<220> FEATURE:
<223> OTHER INFORMATION: Primer sequence

<400> SEQUENCE: 112
ctctgggcca acaacctgta ccgctctgag gtc                                  33

<210> SEQ ID NO 113
<211> LENGTH: 33
<212> TYPE: DNA
<213> ORGANISM: Artificial
<220> FEATURE:
<223> OTHER INFORMATION: Primer sequence

<400> SEQUENCE: 113
gacctcagag cggtacaggt tgttggccca gag                                  33

<210> SEQ ID NO 114
<211> LENGTH: 33
<212> TYPE: DNA
<213> ORGANISM: Artificial
<220> FEATURE:
```

<223> OTHER INFORMATION: Primer sequence

<400> SEQUENCE: 114
ctctgggcca acaacaagta ccgctctgag gtc                                   33

<210> SEQ ID NO 115
<211> LENGTH: 33
<212> TYPE: DNA
<213> ORGANISM: Artificial
<220> FEATURE:
<223> OTHER INFORMATION: Primer sequence

<400> SEQUENCE: 115
gacctcagag cggtacttgt tgttggccca gag                                   33

<210> SEQ ID NO 116
<211> LENGTH: 33
<212> TYPE: DNA
<213> ORGANISM: Artificial
<220> FEATURE:
<223> OTHER INFORMATION: Primer sequence

<400> SEQUENCE: 116
gaggtcccga gcttcatctg gctcgaccgc aac                                   33

<210> SEQ ID NO 117
<211> LENGTH: 33
<212> TYPE: DNA
<213> ORGANISM: Artificial
<220> FEATURE:
<223> OTHER INFORMATION: Primer sequence

<400> SEQUENCE: 117
gttgcggtcg agccagatga agctcgggac ctc                                   33

<210> SEQ ID NO 118
<211> LENGTH: 33
<212> TYPE: DNA
<213> ORGANISM: Artificial
<220> FEATURE:
<223> OTHER INFORMATION: Primer sequence

<400> SEQUENCE: 118
gaggtcccga gcttcacctg gctcgaccgc aac                                   33

<210> SEQ ID NO 119
<211> LENGTH: 33
<212> TYPE: DNA
<213> ORGANISM: Artificial
<220> FEATURE:
<223> OTHER INFORMATION: Primer sequence

<400> SEQUENCE: 119
gttgcggtcg agccaggtga agctcgggac ctc                                   33

<210> SEQ ID NO 120
<211> LENGTH: 33
<212> TYPE: DNA
<213> ORGANISM: Artificial
<220> FEATURE:
<223> OTHER INFORMATION: Primer sequence

<400> SEQUENCE: 120
ccgagcttcc agtggatcga ccgcaacgtc acg                                   33

<210> SEQ ID NO 121

```
<211> LENGTH: 33
<212> TYPE: DNA
<213> ORGANISM: Artificial
<220> FEATURE:
<223> OTHER INFORMATION: Primer sequence

<400> SEQUENCE: 121
cgtgacgttg cggtcgatcc actggaagct cgg                                    33

<210> SEQ ID NO 122
<211> LENGTH: 33
<212> TYPE: DNA
<213> ORGANISM: Artificial
<220> FEATURE:
<223> OTHER INFORMATION: Primer sequence

<400> SEQUENCE: 122
ccgagcttcc agtgggtcga ccgcaacgtc acg                                    33

<210> SEQ ID NO 123
<211> LENGTH: 33
<212> TYPE: DNA
<213> ORGANISM: Artificial
<220> FEATURE:
<223> OTHER INFORMATION: Primer sequence

<400> SEQUENCE: 123
cgtgacgttg cggtcgaccc actggaagct cgg                                    33

<210> SEQ ID NO 124
<211> LENGTH: 33
<212> TYPE: DNA
<213> ORGANISM: Artificial
<220> FEATURE:
<223> OTHER INFORMATION: Primer sequence

<400> SEQUENCE: 124
tcgaacggcg agtggtacat cgccaacaac ggc                                    33

<210> SEQ ID NO 125
<211> LENGTH: 33
<212> TYPE: DNA
<213> ORGANISM: Artificial
<220> FEATURE:
<223> OTHER INFORMATION: Primer sequence

<400> SEQUENCE: 125
gccgttgttg gcgatgtacc actcgccgtt cga                                    33

<210> SEQ ID NO 126
<211> LENGTH: 33
<212> TYPE: DNA
<213> ORGANISM: Artificial
<220> FEATURE:
<223> OTHER INFORMATION: Primer sequence

<400> SEQUENCE: 126
tcgaacggcg agtggaagat cgccaacaac ggc                                    33

<210> SEQ ID NO 127
<211> LENGTH: 33
<212> TYPE: DNA
<213> ORGANISM: Artificial
<220> FEATURE:
<223> OTHER INFORMATION: Primer sequence

<400> SEQUENCE: 127
```
gccgttgttg gcgatcttcc actcgccgtt cga                33

<210> SEQ ID NO 128
<211> LENGTH: 33
<212> TYPE: DNA
<213> ORGANISM: Artificial
<220> FEATURE:
<223> OTHER INFORMATION: Primer sequence

<400> SEQUENCE: 128
ggccagaagg aatggcagca ctggtgcaat gcc                33

<210> SEQ ID NO 129
<211> LENGTH: 33
<212> TYPE: DNA
<213> ORGANISM: Artificial
<220> FEATURE:
<223> OTHER INFORMATION: Primer sequence

<400> SEQUENCE: 129
ggcattgcac cagtgctgcc attccttctg gcc                33

<210> SEQ ID NO 130
<211> LENGTH: 33
<212> TYPE: DNA
<213> ORGANISM: Artificial
<220> FEATURE:
<223> OTHER INFORMATION: Primer sequence

<400> SEQUENCE: 130
gacacgaccg ctgcccagta cgactaccac tgc                33

<210> SEQ ID NO 131
<211> LENGTH: 33
<212> TYPE: DNA
<213> ORGANISM: Artificial
<220> FEATURE:
<223> OTHER INFORMATION: Primer sequence

<400> SEQUENCE: 131
gcagtggtag tcgtactggg cagcggtcgt gtc                33

<210> SEQ ID NO 132
<211> LENGTH: 33
<212> TYPE: DNA
<213> ORGANISM: Artificial
<220> FEATURE:
<223> OTHER INFORMATION: Primer sequence

<400> SEQUENCE: 132
gacacgaccg ctgccttcta cgactaccac tgc                33

<210> SEQ ID NO 133
<211> LENGTH: 33
<212> TYPE: DNA
<213> ORGANISM: Artificial
<220> FEATURE:
<223> OTHER INFORMATION: Primer sequence

<400> SEQUENCE: 133
gcagtggtag tcgtagaagg cagcggtcgt gtc                33

<210> SEQ ID NO 134
<211> LENGTH: 34
<212> TYPE: DNA
<213> ORGANISM: Artificial
<220> FEATURE:

```
<223> OTHER INFORMATION: Primer sequence

<400> SEQUENCE: 134
gatcttcctc agccctctgt acgcgaacga ggtc                              34

<210> SEQ ID NO 135
<211> LENGTH: 34
<212> TYPE: DNA
<213> ORGANISM: Artificial
<220> FEATURE:
<223> OTHER INFORMATION: Primer sequence

<400> SEQUENCE: 135
gacctcgttc gcgtacagag ggctgaggaa gatc                              34

<210> SEQ ID NO 136
<211> LENGTH: 34
<212> TYPE: DNA
<213> ORGANISM: Artificial
<220> FEATURE:
<223> OTHER INFORMATION: Primer sequence

<400> SEQUENCE: 136
gatcttcctc agccctaagt acgcgaacga ggtc                              34

<210> SEQ ID NO 137
<211> LENGTH: 34
<212> TYPE: DNA
<213> ORGANISM: Artificial
<220> FEATURE:
<223> OTHER INFORMATION: Primer sequence

<400> SEQUENCE: 137
gacctcgttc gcgtacttag ggctgaggaa gatc                              34

<210> SEQ ID NO 138
<211> LENGTH: 36
<212> TYPE: DNA
<213> ORGANISM: Artificial
<220> FEATURE:
<223> OTHER INFORMATION: Primer sequence

<400> SEQUENCE: 138
gcaaatatcc ccactttcat ctggctggac tctgtc                            36

<210> SEQ ID NO 139
<211> LENGTH: 36
<212> TYPE: DNA
<213> ORGANISM: Artificial
<220> FEATURE:
<223> OTHER INFORMATION: Primer sequence

<400> SEQUENCE: 139
gacagagtcc agccagatga aagtggggat atttgc                            36

<210> SEQ ID NO 140
<211> LENGTH: 36
<212> TYPE: DNA
<213> ORGANISM: Artificial
<220> FEATURE:
<223> OTHER INFORMATION: Primer sequence

<400> SEQUENCE: 140
gcaaatatcc ccactttcca gtggctggac tctgtc                            36

<210> SEQ ID NO 141
```

```
<211> LENGTH: 36
<212> TYPE: DNA
<213> ORGANISM: Artificial
<220> FEATURE:
<223> OTHER INFORMATION: Primer sequence

<400> SEQUENCE: 141
gacagagtcc agccactgga aagtggggat atttgc                              36

<210> SEQ ID NO 142
<211> LENGTH: 33
<212> TYPE: DNA
<213> ORGANISM: Artificial
<220> FEATURE:
<223> OTHER INFORMATION: Primer sequence

<400> SEQUENCE: 142
cccactttca cgtggatcga ctctgtcgcg aag                                 33

<210> SEQ ID NO 143
<211> LENGTH: 33
<212> TYPE: DNA
<213> ORGANISM: Artificial
<220> FEATURE:
<223> OTHER INFORMATION: Primer sequence

<400> SEQUENCE: 143
cttcgcgaca gagtcgatcc acgtgaaagt ggg                                 33

<210> SEQ ID NO 144
<211> LENGTH: 33
<212> TYPE: DNA
<213> ORGANISM: Artificial
<220> FEATURE:
<223> OTHER INFORMATION: Primer sequence

<400> SEQUENCE: 144
cccactttca cgtgggtcga ctctgtcgcg aag                                 33

<210> SEQ ID NO 145
<211> LENGTH: 33
<212> TYPE: DNA
<213> ORGANISM: Artificial
<220> FEATURE:
<223> OTHER INFORMATION: Primer sequence

<400> SEQUENCE: 145
cttcgcgaca gagtcgaccc acgtgaaagt ggg                                 33

<210> SEQ ID NO 146
<211> LENGTH: 33
<212> TYPE: DNA
<213> ORGANISM: Artificial
<220> FEATURE:
<223> OTHER INFORMATION: Primer sequence

<400> SEQUENCE: 146
tccaacggag agttctacat tgccaacaac gga                                 33

<210> SEQ ID NO 147
<211> LENGTH: 33
<212> TYPE: DNA
<213> ORGANISM: Artificial
<220> FEATURE:
<223> OTHER INFORMATION: Primer sequence

<400> SEQUENCE: 147
```

```
tccgttgttg gcaatgtaga actctccgtt gga                              33
```

<210> SEQ ID NO 148
<211> LENGTH: 33
<212> TYPE: DNA
<213> ORGANISM: Artificial
<220> FEATURE:
<223> OTHER INFORMATION: Primer sequence

<400> SEQUENCE: 148

```
tccaacggag agttcaagat tgccaacaac gga                              33
```

<210> SEQ ID NO 149
<211> LENGTH: 33
<212> TYPE: DNA
<213> ORGANISM: Artificial
<220> FEATURE:
<223> OTHER INFORMATION: Primer sequence

<400> SEQUENCE: 149

```
tccgttgttg gcaatcttga actctccgtt gga                              33
```

<210> SEQ ID NO 150
<211> LENGTH: 34
<212> TYPE: DNA
<213> ORGANISM: Artificial
<220> FEATURE:
<223> OTHER INFORMATION: Primer sequence

<400> SEQUENCE: 150

```
catccgccaa cagtggcagg actggtgcaa catc                             34
```

<210> SEQ ID NO 151
<211> LENGTH: 34
<212> TYPE: DNA
<213> ORGANISM: Artificial
<220> FEATURE:
<223> OTHER INFORMATION: Primer sequence

<400> SEQUENCE: 151

```
gatgttgcac cagtcctgcc actgttggcg gatg                             34
```

<210> SEQ ID NO 152
<211> LENGTH: 37
<212> TYPE: DNA
<213> ORGANISM: Artificial
<220> FEATURE:
<223> OTHER INFORMATION: Primer sequence

<400> SEQUENCE: 152

```
ccaacagctc ctcgccccag tacgactcga cttgttc                          37
```

<210> SEQ ID NO 153
<211> LENGTH: 37
<212> TYPE: DNA
<213> ORGANISM: Artificial
<220> FEATURE:
<223> OTHER INFORMATION: Primer sequence

<400> SEQUENCE: 153

```
gaacaagtcg agtcgtactg gggcgaggag ctgttgg                          37
```

<210> SEQ ID NO 154
<211> LENGTH: 37
<212> TYPE: DNA
<213> ORGANISM: Artificial
<220> FEATURE:

-continued

<223> OTHER INFORMATION: Primer sequence

<400> SEQUENCE: 154
ccaacagctc ctcgcccttc tacgactcga cttgttc        37

<210> SEQ ID NO 155
<211> LENGTH: 37
<212> TYPE: DNA
<213> ORGANISM: Artificial
<220> FEATURE:
<223> OTHER INFORMATION: Primer sequence

<400> SEQUENCE: 155
gaacaagtcg agtcgtagaa gggcgaggag ctgttgg        37

<210> SEQ ID NO 156
<211> LENGTH: 447
<212> TYPE: PRT
<213> ORGANISM: Trichoderma reesei

<400> SEQUENCE: 156

```
Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285
```

```
Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 157
<211> LENGTH: 447
<212> TYPE: PRT
<213> ORGANISM: Trichoderma reesei

<400> SEQUENCE: 157

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro Val
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Ile Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220
```

-continued

```
Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Gln Trp Gly Asp Trp Cys
    355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
    435                 440                 445

<210> SEQ ID NO 158
<211> LENGTH: 447
<212> TYPE: PRT
<213> ORGANISM: Trichoderma reesei

<400> SEQUENCE: 158

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
        100                 105                 110

Ile Pro Ser Leu Thr Gly Ala Met Ala Thr Ala Ala Ala Val Ala
    115                 120                 125

Lys Val Pro Ser Phe Gln Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160
```

```
Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 159
<211> LENGTH: 447
<212> TYPE: PRT
<213> ORGANISM: Trichoderma reesei

<400> SEQUENCE: 159

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95
```

```
Thr Pro Trp Ala Asn Ala Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Thr Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 160
<211> LENGTH: 447
<212> TYPE: PRT
<213> ORGANISM: Trichoderma reesei

<400> SEQUENCE: 160

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

-continued

Tyr Tyr Ser Gln Cys Leu Pro Gly Ala Ala Ser Ser Ser Ser Thr
        35              40                  45

Arg Ala Ala Ser Thr Thr Ser Arg Val Ser Pro Thr Thr Ser Arg Ser
 50                  55                  60

Ser Ser Ala Thr Pro Pro Pro Gly Ser Thr Thr Thr Arg Val Pro Pro
 65              70                  75                  80

Val Gly Ser Gly Thr Ala Thr Tyr Ser Gly Asn Pro Phe Val Gly Val
             85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Val Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
                275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 161

```
<211> LENGTH: 447
<212> TYPE: PRT
<213> ORGANISM: Trichoderma reesei

<400> SEQUENCE: 161

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Tyr Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400
```

```
Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445
```